US012709771B2

(12) United States Patent
Schnall-Levin

(10) Patent No.: US 12,709,771 B2
(45) Date of Patent: Aug. 18, 2026

(54) METHODS AND COMPOSITIONS FOR MULTIPLEX CELL ANALYSIS

(71) Applicant: 10x Genomics, Inc., Pleasanton, CA (US)

(72) Inventor: Michael Schnall-Levin, San Francisco, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 582 days.

(21) Appl. No.: 18/131,800

(22) Filed: Apr. 6, 2023

(65) Prior Publication Data

US 2023/0323427 A1 Oct. 12, 2023

Related U.S. Application Data

(60) Provisional application No. 63/328,188, filed on Apr. 6, 2022.

(51) Int. Cl.
*C12Q 1/6806* (2018.01)
*C12Q 1/6874* (2018.01)
*C12Q 1/6876* (2018.01)

(52) U.S. Cl.
CPC ......... *C12Q 1/6806* (2013.01); *C12Q 1/6874* (2013.01); *C12Q 1/6876* (2013.01)

(58) Field of Classification Search
CPC .. C12Q 1/6806; C12Q 1/6874; C12Q 1/6876; C12Q 1/6804; C12Q 1/6841; G01N 33/56966; G01N 33/58; G01N 2458/10
See application file for complete search history.

(56) References Cited

U.S. PATENT DOCUMENTS 4,683,195 A 7/1987 Mullis et al.
4,683,202 A 7/1987 Mullis
4,800,159 A 1/1989 Mullis et al.
4,965,188 A 10/1990 Mullis et al.
5,512,462 A 4/1996 Cheng
5,599,675 A 2/1997 Brenner
5,635,352 A 6/1997 Urdea et al.
5,695,940 A 12/1997 Drmanac et al.
5,750,341 A 5/1998 Macevicz
6,054,274 A 4/2000 Sampson et al.
6,172,218 B1 1/2001 Brenner
6,265,552 B1 7/2001 Schatz
6,291,187 B1 9/2001 Kingsmore et al.
6,306,597 B1 10/2001 Macevicz
6,323,009 B1 11/2001 Lasken et al.
6,344,329 B1 2/2002 Lizardi et al.
6,368,801 B1 4/2002 Faruqi
6,391,937 B1 5/2002 Beuhler et al.
6,534,266 B1 3/2003 Singer
6,828,109 B2 12/2004 Kaplan
6,969,488 B2 11/2005 Bridgham et al.
7,057,026 B2 6/2006 Barnes et al.
7,255,994 B2 8/2007 Lao
7,264,929 B2 9/2007 Rothberg et al.
7,345,159 B2 3/2008 Ju et al.
7,473,767 B2 1/2009 Dimitrov
7,534,991 B2 5/2009 Miller et al.
7,544,794 B1 6/2009 Benner
7,555,155 B2 6/2009 Levenson et al.
7,566,537 B2 7/2009 Balasubramanian et al.
7,632,641 B2 12/2009 Dirks et al.
7,655,898 B2 2/2010 Miller
7,709,198 B2 5/2010 Luo et al.
7,721,721 B1 5/2010 Kronengold et al.
7,893,227 B2 2/2011 Wu et al.
7,910,304 B2 3/2011 Drmanac
7,941,279 B2 5/2011 Hwang et al.
7,989,166 B2 8/2011 Koch et al.
8,124,751 B2 2/2012 Pierce et al.
8,199,999 B2 6/2012 Hoyt et al.
8,268,554 B2 9/2012 Schallmeiner
8,330,087 B2 12/2012 Domenicali
8,415,102 B2 4/2013 Geiss et al.
8,431,691 B2 4/2013 Mckernan et al.
8,460,865 B2 6/2013 Chee et al.
8,462,981 B2 6/2013 Determan et al.
8,481,258 B2 7/2013 Church et al.
8,519,115 B2 8/2013 Webster et al.
8,551,710 B2 10/2013 Bernitz et al.
8,604,182 B2 12/2013 Luo et al.
8,632,975 B2 1/2014 Vander Horn et al.
8,658,361 B2 2/2014 Wu et al.
8,771,950 B2 7/2014 Church et al.
8,951,726 B2 2/2015 Luo et al.
8,986,926 B2 3/2015 Ferree et al.
9,201,063 B2 12/2015 Sood et al.
9,273,349 B2 3/2016 Nguyen et al.
(Continued)

FOREIGN PATENT DOCUMENTS

WO WO 2005/065814 7/2005
WO WO 2006/064199 6/2006
(Continued)

OTHER PUBLICATIONS

Cheng et al., "Multiplexing Methods for Simultaneous Large-Scale Transcriptomic Profiling of Samples at Single-Cell Resolution," Adv Sci (Weinh). (2021) 8(17):e2101229.
(Continued)

*Primary Examiner* — Cynthia B Wilder
(74) *Attorney, Agent, or Firm* — WILSON SONSINI GOODRICH & ROSATI

(57) ABSTRACT

Provided herein in some aspects are methods, compositions, kits, and systems for performing multiplexed single-cell analysis on an in situ platform, providing alternatives which have a higher cell throughput and/or lower cost per cell compared to current single-cell analysis techniques. In some embodiments, the methods disclosed herein comprise using labeling agents that comprise sample-specific barcodes and/or cell feature specific barcodes (e.g., analyte specific barcodes) to label single-cell populations, immobilizing the labeled cells, and performing in situ detection of the labeling agents and/or other features including cellular analytes of the labeled cells.

20 Claims, 4 Drawing Sheets

(56) References Cited

U.S. PATENT DOCUMENTS 9,371,563 B2 6/2016 Geiss et al.
9,371,598 B2 6/2016 Chee
9,376,717 B2 6/2016 Gao et al.
9,512,422 B2 12/2016 Barnard et al.
9,541,504 B2 1/2017 Hoyt
9,551,032 B2 1/2017 Landegren et al.
9,624,538 B2 4/2017 Church et al.
9,650,406 B2 5/2017 Zhou et al.
9,714,446 B2 7/2017 Webster et al.
9,714,937 B2 7/2017 Dunaway
9,727,810 B2 8/2017 Fodor et al.
9,778,155 B2 10/2017 Gradinaru et al.
9,783,841 B2 10/2017 Nolan et al.
9,889,422 B2 2/2018 Smith et al.
9,909,167 B2 3/2018 Samusik et al.
10,032,064 B2 7/2018 Hoyt
10,059,990 B2 8/2018 Boyden et al.
10,126,242 B2 11/2018 Miller et al.
10,138,509 B2 11/2018 Church et al.
10,179,932 B2 1/2019 Church et al.
10,227,639 B2 3/2019 Levner et al.
10,246,700 B2 4/2019 Dunaway et al.
10,266,888 B2 4/2019 Daugharthy et al.
10,267,808 B2 4/2019 Cai
10,309,879 B2 6/2019 Chen et al.
10,317,321 B2 6/2019 Tillberg et al.
10,364,457 B2 7/2019 Wassie et al.
10,370,698 B2 8/2019 Nolan et al.
10,415,080 B2 9/2019 Dunaway et al.
10,450,599 B2 10/2019 Pierce et al.
10,457,980 B2 10/2019 Cai et al.
10,465,235 B2 11/2019 Gullberg et al.
10,494,662 B2 12/2019 Church et al.
10,495,554 B2 12/2019 Deisseroth et al.
10,501,777 B2 12/2019 Beechem et al.
10,501,791 B2 12/2019 Church et al.
10,510,435 B2 12/2019 Cai et al.
10,526,649 B2 1/2020 Chen et al.
10,545,075 B2 1/2020 Deisseroth et al.
10,550,429 B2 2/2020 Harada et al.
10,580,128 B2 3/2020 Miller
10,640,816 B2 5/2020 Beechem et al.
10,640,826 B2 5/2020 Church et al.
10,669,569 B2 6/2020 Gullberg et al.
10,746,981 B2 8/2020 Tomer et al.
10,774,372 B2 9/2020 Chee et al.
10,774,374 B2 9/2020 Frisén et al.
10,794,802 B2 10/2020 Gradinaru et al.
10,802,262 B2 10/2020 Tomer et al.
10,815,519 B2 10/2020 Husain et al.
10,829,814 B2 11/2020 Fan et al.
10,844,426 B2 11/2020 Daugharthy et al.
10,858,698 B2 12/2020 Church et al.
10,872,679 B2 12/2020 Cai et al.
10,964,001 B2 3/2021 Miller
11,174,281 B1 11/2021 Graham et al.
11,287,422 B2 3/2022 Previte et al.
11,434,525 B2 9/2022 Glezer
11,459,603 B2 10/2022 Tyagi et al.
11,499,185 B2 11/2022 Vijayan et al.
11,643,679 B2 5/2023 Glezer et al.
11,999,999 B2 6/2024 Ju et al.
12,139,751 B2 11/2024 Qian et al.
2005/0100900 A1 5/2005 Kawashima et al.
2006/0188901 A1 8/2006 Barnes et al.
2006/0234261 A1 10/2006 Pierce et al.
2006/0240439 A1 10/2006 Smith et al.
2006/0281109 A1 12/2006 Barr et al.
2007/0166705 A1 7/2007 Milton et al.
2010/0055733 A1 3/2010 Lutolf et al.
2011/0223585 A1 9/2011 Gullberg et al.
2012/0270305 A1 10/2012 Reed et al.
2013/0079232 A1 3/2013 Kain et al.
2013/0260372 A1 10/2013 Buermann et al.
2013/0288249 A1 10/2013 Gullbert
2013/0323729 A1 12/2013 Landegren et al.
2014/0194311 A1 7/2014 Gullberg et al.
2016/0024555 A1 1/2016 Church et al.
2016/0108458 A1 4/2016 Frei et al.
2016/0305856 A1 10/2016 Boyden et al.
2016/0369329 A1 12/2016 Cai et al.
2016/0376642 A1 12/2016 Landegren et al.
2017/0009278 A1 1/2017 Söderberg et al.
2017/0081489 A1 3/2017 Rodriques et al.
2017/0101672 A1 4/2017 Luo et al.
2017/0220733 A1 8/2017 Zhuang et al.
2017/0253918 A1 9/2017 Kohman
2018/0052081 A1 2/2018 Kohman
2018/0080876 A1 3/2018 Rockel et al.
2018/0208967 A1 7/2018 Larman et al.
2018/0237864 A1 8/2018 Imler et al.
2018/0251833 A1 9/2018 Daugharthy et al.
2018/0320226 A1 11/2018 Church et al.
2019/0017106 A1 1/2019 Frisen et al.
2019/0032121 A1 1/2019 Daugharthy et al.
2019/0032128 A1 1/2019 Chen et al.
2019/0055594 A1 2/2019 Samusik et al.
2019/0106733 A1 4/2019 Kishi et al.
2019/0112599 A1 4/2019 Church et al.
2019/0119735 A1 4/2019 Deisseroth et al.
2019/0155835 A1 5/2019 Daugharthy et al.
2019/0161796 A1 5/2019 Hauling et al.
2019/0177718 A1 6/2019 Church et al.
2019/0177800 A1 6/2019 Boutet et al.
2019/0194709 A1 6/2019 Church et al.
2019/0218608 A1 7/2019 Daugharthy et al.
2019/0249248 A1 8/2019 Beechem et al.
2019/0264270 A1 8/2019 Zhuang et al.
2019/0271028 A1 9/2019 Khafizov et al.
2019/0276881 A1 9/2019 Zhuang et al.
2019/0330617 A1 10/2019 Church et al.
2019/0339203 A1 11/2019 Miller et al.
2019/0367969 A1 12/2019 Belhocine
2019/0376956 A1 12/2019 Bobrow et al.
2020/0010891 A1 1/2020 Beechem et al.
2020/0071751 A1 3/2020 Daugharthy et al.
2020/0123597 A1 4/2020 Daniel
2020/0140920 A1 5/2020 Pierce et al.
2020/0224243 A1 7/2020 Desai et al.
2020/0224244 A1 7/2020 Nilsson et al.
2020/0239946 A1 7/2020 Dewal
2020/0354774 A1 11/2020 Church et al.
2020/0354782 A1 11/2020 Dewal
2020/0362398 A1 11/2020 Kishi et al.
2020/0393343 A1 12/2020 Kennedy-Darling et al.
2020/0399689 A1 12/2020 Luo et al.
2021/0017587 A1 1/2021 Cai et al.
2021/0115504 A1 4/2021 Cai et al.
2021/0164039 A1 6/2021 Wang et al.
2021/0222234 A1 7/2021 Carlson
2021/0238662 A1 8/2021 Bava
2021/0238674 A1 8/2021 Bava
2021/0254140 A1 8/2021 Stahl et al.
2021/0262018 A1 8/2021 Bava et al.
2021/0277460 A1 9/2021 Bava
2021/0332425 A1 10/2021 Pfeiffer et al.
2021/0340618 A1 11/2021 Kuhnemund et al.
2021/0340621 A1 11/2021 Daugharthy et al.
2021/0388423 A1 12/2021 Bava et al.
2021/0388424 A1 12/2021 Bava
2022/0010358 A1 1/2022 Kuhnemund et al.
2022/0026433 A1 1/2022 Guo et al.
2022/0049302 A1 2/2022 Daugharthy et al.
2022/0049303 A1 2/2022 Busby et al.
2022/0064697 A1 3/2022 Zhuang et al.
2022/0083832 A1 3/2022 Shah
2022/0084628 A1 3/2022 Shah
2022/0084629 A1 3/2022 Shah
2022/0128565 A1 4/2022 Miller et al.
2022/0136049 A1 5/2022 Bava et al.
2022/0186300 A1 6/2022 Bava
2022/0195498 A1 6/2022 Kuhnemund et al.
2022/0213529 A1 7/2022 Kuhnemund et al.
2022/0228200 A1 7/2022 Bava

(56) References Cited

U.S. PATENT DOCUMENTS

2022/0235403 A1 7/2022 Costa
2022/0236258 A1 7/2022 McDermott et al.
2022/0282306 A1 9/2022 Bava
2022/0282316 A1 9/2022 Bava
2022/0282319 A1 9/2022 Verheyen
2022/0372570 A1 11/2022 Costa
2022/0380838 A1 12/2022 Qian
2022/0403458 A1 12/2022 Bava
2023/0002808 A1 1/2023 Mignardi
2023/0012607 A1 1/2023 Kühnemund et al.
2023/0013775 A1 1/2023 Chen et al.
2023/0015226 A1 1/2023 Chen et al.
2023/0026886 A1 1/2023 Chen
2023/0031305 A1 2/2023 Verheyen
2023/0031996 A1 2/2023 Qian et al.
2023/0035685 A1 2/2023 Qian et al.
2023/0037182 A1 2/2023 Bava et al.
2023/0039148 A1 2/2023 Verheyen
2023/0039899 A1 2/2023 Larman et al.
2023/0041485 A1 2/2023 Marks
2023/0044650 A1 2/2023 Dockter
2023/0057571 A1 2/2023 Costa et al.
2023/0061542 A1 3/2023 Kühnemund
2023/0084407 A1 3/2023 Hernández Neuta et al.
2023/0115903 A1 4/2023 Hernández Neuta et al.
2023/0159997 A1 5/2023 Belhocine et al.
2023/0160794 A1 5/2023 Dockter et al.
2023/0183787 A1 6/2023 Bava et al.
2023/0242974 A1 8/2023 Costa et al.
2023/0279465 A1 9/2023 He et al.
2023/0279475 A1 9/2023 Kuhnemund et al.
2023/0279480 A1 9/2023 Kühnemund
2023/0287478 A1 9/2023 Bava
2023/0314327 A1 10/2023 Hoffman
2023/0314328 A1 10/2023 Costa
2023/0323430 A1 10/2023 Shastry
2023/0323437 A1 10/2023 Chen et al.
2023/0374573 A1 11/2023 Qian et al.
2023/0374580 A1 11/2023 Costa
2023/0416821 A1 12/2023 Bava et al.
2024/0002902 A1 1/2024 Jakobsen et al.
2024/0026426 A1 1/2024 Bava
2024/0026427 A1 1/2024 Kuhnemund
2024/0026439 A1 1/2024 Sasaki
2024/0026448 A1 1/2024 Costa
2024/0035070 A1 2/2024 Christopherson
2024/0035071 A1 2/2024 Delaney et al.
2024/0035072 A1 2/2024 Christopherson
2024/0043910 A1 2/2024 Shastry
2024/0043914 A1 2/2024 Chen et al.
2024/0060119 A1 2/2024 Bava
2024/0084373 A1 3/2024 Shastry
2024/0084378 A1 3/2024 Marks et al.
2024/0101978 A1 3/2024 Boghospor et al.
2024/0132938 A1 4/2024 Kühnemund
2024/0141418 A1 5/2024 Mielinis
2024/0150816 A1 5/2024 Feng et al.
2024/0158852 A1 5/2024 Belhocine et al.
2024/0167081 A1 5/2024 Bava et al.
2024/0175082 A1 5/2024 Costa
2024/0175083 A1 5/2024 Bava et al.
2024/0191297 A1 6/2024 Christopherson et al.
2024/0209330 A1 6/2024 Shastry et al.
2024/0218424 A1 7/2024 Costa et al.
2024/0218437 A1 7/2024 Belhocine et al.
2024/0263219 A1 8/2024 Kuhnemund
2024/0263220 A1 8/2024 Olofsson
2024/0264155 A1 8/2024 Costa
2024/0301475 A1 9/2024 Mielinis
2024/0305314 A1 9/2024 Hoffman et al.
2024/0331348 A1 10/2024 Bava et al.
2024/0351041 A1 10/2024 Christopherson et al.
2024/0368677 A1 11/2024 Mignardi
2024/0368678 A1 11/2024 Bloju
2024/0369471 A1 11/2024 Hoffman et al.
2024/0376521 A1 11/2024 Costa et al.
2024/0384330 A1 11/2024 Mignardi et al.
2024/0428880 A1 12/2024 Marks et al.
2025/0043339 A1 2/2025 Wang et al.
2025/0075263 A1 3/2025 Bent et al.
2025/0075267 A1 3/2025 Hayes et al.
2025/0092443 A1 3/2025 Oh
2025/0129411 A1 4/2025 Sasaki et al.
2025/0163502 A1 5/2025 Costa et al.
2025/0179571 A1 6/2025 Sasaki
2025/0188519 A1 6/2025 Mignardi et al.
2025/0207189 A1 6/2025 Chitnis et al.
2025/0207203 A1 6/2025 Schnall-Levin
2025/0236906 A1 7/2025 Bloju
2025/0257391 A1 8/2025 Mignardi
2025/0257394 A1 8/2025 Chitnis et al.
2025/0263783 A1 8/2025 Sasaki et al.
2025/0270636 A1 8/2025 Bell et al.
2025/0277262 A1 9/2025 Chitnis et al.
2025/0327114 A1 10/2025 Marks et al.

FOREIGN PATENT DOCUMENTS

WO WO 2007/010251 1/2007
WO WO 2014/025392 2/2014
WO WO 2014/163886 10/2014
WO WO 2017/079406 5/2017
WO WO-2017075294 A1 5/2017
WO WO 2017/143155 8/2017
WO WO 2018/026873 2/2018
WO WO 2019/113533 6/2019
WO WO 2019/199579 10/2019
WO WO 2019/222284 11/2019
WO WO 2019/226631 11/2019
WO WO 2019/236841 12/2019
WO WO 2020/076976 4/2020
WO WO 2020/076979 4/2020
WO WO 2020/096687 5/2020
WO WO 2020/099640 5/2020
WO WO 2020/102094 5/2020
WO WO 2020/117914 6/2020
WO WO 2020/123316 6/2020
WO WO 2020/123742 6/2020
WO WO 2020/142490 7/2020
WO WO 2020/163397 8/2020
WO WO 2020/240025 12/2020
WO WO 2020/254519 12/2020
WO WO-2021046475 A1 3/2021
WO WO 2021/067475 4/2021
WO WO 2021/123282 6/2021
WO WO 2021/123286 6/2021
WO WO 2021/138676 7/2021
WO WO 2021/155063 8/2021
WO WO 2021/167526 8/2021
WO WO 2021/168287 8/2021
WO WO 2021/168326 8/2021
WO WO-2021168287 A1 * 8/2021 ........... C12Q 1/6841
WO WO-2021174051 A1 * 9/2021 ........... C12Q 1/6806
WO WO 2021/249816 12/2021
WO WO 2022/197801 9/2022
WO WO-2023108139 A2 6/2023
WO WO-2023141476 A1 7/2023
WO WO-2023172915 A1 9/2023
WO WO-2023192302 A1 10/2023
WO WO-2023196526 A1 10/2023
WO WO-2024148300 A1 7/2024

OTHER PUBLICATIONS

He et al., "High-plex Multiomic Analysis in FFPE at Subcellular Level by Spatial Molecular Imaging," bioRxiv (2022) doi:10.1101/2021.11.03.467020.

Baner et al., "Signal amplification of padlock probes by rolling circle replication," Nucleic Acids Res. (1998) 26(22):5073-5078.

Bechara et al., "Cell-penetrating peptides: 20 years later, where do we stand?," FEBS Lett. (2013) 587(12):1693-702.

(56) References Cited

OTHER PUBLICATIONS

Bibikova et al., "Quantitative gene expression profiling in formalin-fixed, paraffin-embedded tissues using universal bead arrays," Am J Pathol. Nov. 2004;165(5):1799-807.
Bolognesi et al., "Multiplex Staining by Sequential Immunostaining and Antibody Removal on Routine Tissue Sections," J. Histochem. Cytochem. (2017); 65(8): 431-444.
Capodieci et al., "Gene expression profiling in single cells within tissue," Nat Methods. (2005) 2(9): 663-5.
Chemeris et al., "Real-time hybridization chain reaction," Dokl Biochem Biophys. (2008) 419: 53-55.
Chen et al., "Efficient in situ barcode sequencing using padlock probe-based BaristaSeq," Nucleic Acids Res. (2018) 46(4): e22.
Chen et al., "RNA imaging. Spatially resolved, highly multiplexed RNA profiling in single cells," Science. (2015) 348(6233): aaa6090. 16 pgs.
Chen et al., "Expansion Microscopy," Science (2015) 347(6221):543-548.
Cheung et al., "Chitosan: An Update on Potential Biomedical and Pharmaceutical Applications," Mar Drugs. (2015) 13(8):5156-86.
Choi et al., "Programmable in situ amplification for multiplexed imaging of mRNA expression," Nat Biotechnol. (2010) 28(11): 1208-1212.
Choi et al., "Third-generation in situ hybridization chain reaction: multiplexed, quantitative, sensitive, versatile, robust," Development. (2018) 6;145(12): dev165753.
Conze et al., "Single molecule analysis of combinatorial splicing," Nucleic Acids Res. (2010) 38(16): e163.
Dean et al., "Rapid Amplification Of Plasmid And Phage DNA Using Phi29 DNA Polymerase And Multiply-Primed Rolling Circle Amplification," Genome Research (2001) 11:1095-1099.
Dirks et al., "Triggered amplification by hybridization chain reaction," Proc Natl Acad Sci USA. (2004) 101(43): 15275-15278.
Eng et al., "Transcriptome-scale super-resolved imaging in tissues by RNA seqFISH," Nature. (2019) 568(7751): 235-239.
Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.
Faruqi et al., "High-throughput genotyping of single nucleotide polymorphisms with rolling circle amplification," BMC Genomics. (2001) 2:4.
Feldman et al., Optical Pooled Screens in Human Cells, Cell. (2019) 179(3):787-799.e17.
Femino et al., "Visualization of single RNA transcripts in situ," Science. (1998) 280(5363): 585-90.
Forcucci et al., "All-plastic miniature fluorescence microscope for point-of-care readout of bead-based bioassays," J Biomed Opt. (2015) 20(10): 105010.
Frei et al., "Highly multiplexed simultaneous detection of RNAs and proteins in single cells," Nat Methods. (2016) 13(3): 269-275.
Gavrilovic et al., "Automated classification of multicolored rolling circle products in dual-channel wide-field fluorescence microscopy," Cytometry A. (2011) 79(7): 518-27.
Geiss et al., "Direct multiplexed measurement of gene expression with color-coded probe pairs," Nat Biotechnol. (2008) 26(3): 317-25.
Glass et al., "SIMPLE: a sequential immunoperoxidase labeling and erasing method," J Histochem Cytochem. (2009) 57(10); 899-905.
Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.
Goransson et al., "A single molecule array for digital targeted molecular analyses," Nucleic Acids Res. 2009 37(1):e7. doi: 10.1093/nar/gkn921.
Gunderson et al. "Decoding randomly ordered DNA arrays." Genome research 14.5 (2004): 870-877.
Han et al., "Quantum-dot-tagged microbeads for multiplexed optical coding of biomolecules," Nat Biotechnol. (2001) 19(7): 631-5.
Hein et al., "Click chemistry, a powerful tool for pharmaceutical sciences," Pharm Res. (2008) 25(10):2216-30.
Hughes et al., "Choose your label wisely: water-soluble fluorophores often interact with lipid bilayers," PLoS One. (2014) 9(2):e87649.
Itzkovitz et al., "Single-molecule transcript counting of stem-cell markers in the mouse intestine," Nat Cell Biol. (2011) 14(1): 106-14.
Itzkovitz et al., "Validating Transcripts with Probes and Imaging Technology," Nat Methods. (2011) 8(4 Suppl): S12-S19.
Jamur et al., "Permeabilization of cell membranes," Method Mol. Biol. (2010) 588: 63-66 (abstract only).
Juliano, R., "The delivery of therapeutic oligonucleotides," Nucleic Acids Res. (2016) 44(14):6518-48.
Kolb et al., "Click Chemistry: Diverse Chemical Function from a Few Good Reactions," Angew Chem Int Ed Engl. (2001) 40(11):2004-2021.
Korlach et al. "Selective aluminum passivation for targeted immobilization of single DNA polymerase molecules in zero-mode waveguide nanostructures." *Proceedings of the National Academy of Sciences* 105.4 (2008): 1176-1181.
Lagunavicius et al., "Novel application of Phi29 DNA polymerase: RNA detection and analysis in vitro and in situ by target RNA-primed RCA," RNA. (2009) 15(5):765-71.
Larsson et al. "In situ detection and genotyping of individual mRNA molecules," Nat Methods. (2010) 7(5):395-397.
Lee et al. "Highly Multiplexed Subcellular RNA Sequencing In Situ", Science (2014) 343(6177):1360-1363.
Levene et al. "Zero-mode waveguides for single-molecule analysis at high concentrations." science 299.5607 (2003): 682-686.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Lin et al., "Highly multiplexed imaging of single cells using a high-throughput cyclic immunofluorescence method," Nat Commun. (2015) 6:8390.
Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.
Lizardi et al., "Mutation detection and single-molecule counting using isothermal rolling-circle amplification," Nat Genet. (1998) 19(3): 225-232.
Lundquist et al. "Parallel confocal detection of single molecules in real time." Optics letters 33.9 (2008): 1026-1028.
Maierhorfer et al., "Multicolor deconvolution microscopy of thick biological specimens," Am J Pathol. (2003) 162(2): 373-9.
McGinn et al., "New technologies for DNA analysis—a review of the READNA Project," N Biotechnol. (2016) 33(3): 311-30. doi: 10.1016/j.nbt.2015.10.003.
Meade et al. "Multiplexed DNA detection using spectrally encoded porous SiO2 photonic crystal particles," Anal Chem. (2009) 81(7): 2618-25.
Mitra et al., "Fluorescent in situ sequencing on polymerase colonies," Anal. Biochem. (2003) 320, 55-65.
Moffitt et al., "RNA Imaging with Multiplexed Error-Robust Fluorescence In Situ Hybridization (MERFISH)," Methods in Enzymology, (2016) 572; 1-49.
Mohsen et al., "The Discovery of Rolling Circle Amplification and Rolling Circle Transcription," Acc Chem Res. (2016) 49(11): 2540-2550.
Nagendran et al., "Automated cell-type classification in intact tissues by single-cell molecular profiling," Elife. (2018) 7:e30510.
Nallur et al., "Signal amplification by rolling circle amplification on DNA microarrays," Nucleic Acids Res. (2001) 29(23): e118.
Niu et al., "Fluorescence detection for DNA using hybridization chain reaction with enzyme-amplification," Chem C+A277ommun (Camb). (2010) 46(18): 3089-91.
Payne et al. "In situ genome sequencing resolves DNA sequence and structure in intact biological samples," Science. (2021) 371(6532): eaay3446. doi: 10.1126/science.aay3446. Epub Dec. 31, 2020.

(56) References Cited

OTHER PUBLICATIONS

Pirici et al., "Antibody elution method for multiple immunohistochemistry on primary antibodies raised in the same species and of the same subtype," J Histochem Cytochem. (2009) 57(6); 567-75.
Przybyla et al., "A new era in functional genomics screens," Nat Rev Genet. (2022) 23(2):89-103.
Raj et al., "Imaging individual mRNA molecules using multiple singly labeled probes," Nat Methods. (2008) 5(10): 877-879.
Rajeswari et al., "Multiple pathogen biomarker detection using an encoded bead array in droplet PCR," J Microbiol Methods. (2017) 139: 22-28.
Raouane et al., "Lipid conjugated oligonucleotides: a useful strategy for delivery," Bioconjug Chem. (2012) 23(6):1091-104.
Rideau et al., "Liposomes and polymersomes: a comparative review towards cell mimicking," Chem Soc Rev. (2018) 47(23):8572-8610.
Rouhanifard et al. "ClampFISH detects individual nucleic acid molecules using click chemistry-based amplification," Nat Biotechnol. (2018) 17 pages. doi: 10.1038/nbt.4286.
Schweitzer et al. "Immunoassays with rolling circle DNA amplification: A versatile platform for ultrasensitive antigen detection," Proc. Natl Acad. Sci. USA (2000) 97:10113-119.
Schweitzer et al., "Multiplexed protein profiling on microarrays by rolling-circle amplification," Nature Biotech. (2002) 20:359-365.
Shelbourne et al., "Fast copper-free click DNA ligation by the ring-strain promoted alkyne-azide cycloaddition reaction," Chem Commun (Camb). (2011) 47(22):6257-6259.
Shendure et al, "Accurate multiplex polony sequencing of an evolved bacterial genome," Science (2005) 309(5741); 1728-1732.
Song et al., "Hybridization chain reaction-based aptameric system for the highly selective and sensitive detection of protein," Analyst. (2012) 137(6):1396-1401.
Spitale et al., "Structural imprints in vivo decode RNA regulatory mechanisms," Nature. (2015) 519(7544):486-90.
Sun et al., "Composite organic-inorganic nanoparticles as Raman labels for tissue analysis," Nano Lett. (2007) 7(2): 351-6.
Takayama et al., "Click Chemistry as a Tool for Cell Engineering and Drug Delivery," Molecules, (2019) 24(1):172.
Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.
Tripathi et al., "Z Probe, An Efficient Tool for Characterizing Long Non-Coding RNA in FFPE Tissues," Noncoding RNA. (2018) 4(3):20.
Tsuneoka et al., "Modified in situ Hybridization Chain Reaction Using Short Hairpin DNAs," Front Mol Neurosci. (2020) 13:75.
Wählby et al., "Sequential immunofluorescence staining and image analysis for detection of large numbers of antigens in individual cell nuclei," Cytometry. (2002) 47(1): 32-41.
Wang et al., "Three-dimensional intact-tissue sequencing of single-cell transcriptional states," Science. (2018) 361(6400): eaat5691.
Wang et al., "Imaging plasma membranes without cellular internalization: multisite membrane anchoring reagents based on glycol chitosan derivatives," J. Mater. Chem. B., (2015) 30:6165.
Weibrecht et al., "Simultaneous visualization of both signaling cascade activity and end-point gene expression in single cells," PLoS One. (2011) 6(5): e20148.
Wilson et al., "Encoded microcarriers for high-throughput multiplexed detection," Angew Chem Int Ed Engl. (2006) 18;45(37): 6104-17.
Wu, C. et al. "RollFISh Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.
Xia et al. "Multiplexed detection of RNA using MERFISH and branched DNA amplification." Scientific reports 9.1 (2019): 1-13.
Xiong et al., "Stepwise "Click" Chemistry for the Template Independent Construction of a Broad Variety of Cross-Linked Oligonucleotides: Influence of Linker Length, Position, and Linking Number on DNA Duplex Stability," J. Org. Chem. (2011) 76(14): 5584-5597.
Zhao et al., "Advances of multiplex and high throughput biomolecular detection technologies based on encoding microparticles," Sci China Chem. (2011) 54(8):1185.
Chen, Xiaoyin et al. Efficient in situ barcode sequencing using padlock probe-based BaristaSeq. Nucleic acids research 46(4):e22, 1-10 (2018).
Lovatt, Ditte et al. Transcriptome in vivo analysis (TIVA) of spatially defined single cells in live tissue. Nature methods 11(2):190-196 (2014).
PCT/US2023/017773 International Search Report and Written Opinion dated Jul. 14, 2023.
Sun, Yu-Chi. et al. Integrating barcoded neuroanatomy with spatial transcriptional profiling enables identification of gene correlates of projections. Nat Neurosci 24(6):873-885 (2021).

* cited by examiner

METHODS AND COMPOSITIONS FOR MULTIPLEX CELL ANALYSIS

CROSS-REFERENCE TO RELATED APPLICATION

This application claims priority to U.S. Provisional Patent Application No. 63/328,188, filed Apr. 6, 2022, entitled "METHODS AND COMPOSITIONS FOR MULTIPLEX CELL ANALYSIS," which is herein incorporated by reference in its entirety for all purposes.

FIELD

The present disclosure relates in some aspects to methods and compositions for multiplexing dissociated single cell samples on an in situ platform.

BACKGROUND

Profiling biological targets in a sample on the single cell level, such as genomic, transcriptomic, or proteomic profiling of single cells, are essential for many purposes, such as understanding the molecular basis of cell identity and developing treatment for diseases. Current single cell-based approaches can suffer from high costs and low throughput, but the potential value of such analysis could be enormous. Therefore, there is a need for new and improved methods. The present disclosure addresses this and other needs.

BRIEF SUMMARY

Microscopy imaging, which can resolve multiple analytes in a sample, can provide valuable information such as analyte abundance and spatial information of analytes in situ, for instance, in a cell or tissue sample. Moreover, an in situ analytical platform can be used to analyze a plurality of cells in the sample. The present disclosure in one aspect combines the powers of single-cell based assays and in situ based assays by utilizing an in situ analytical platform to pool labeled cells and/or nuclei from multiple samples and perform analysis that allows single-cell resolution. This multiplexed approach allows for a high-throughput analysis (e.g., 100,000 cells in a 1 $cm^2$ substrate area) with large cost benefits compared to single-cell sequencing of individual samples.

In preferred embodiments, provided herein is a method for analysis, comprising (a) providing a population of cells comprising a labeled cell, wherein the labeled cell is a cell labeled with a labeling agent comprising a binding moiety and a reporter oligonucleotide, wherein the reporter oligonucleotide comprises a sample-specific barcode sequence corresponding to a sample from which the labeled cell is derived, and wherein the binding moiety is bound to the cell; (b) depositing the population of cells comprising the labeled cell on a substrate to provide a deposited labeled cell; (c) contacting the deposited labeled cell with: (i) a first probe that directly or indirectly binds to the sample-specific barcode sequence, and (ii) a second probe that directly or indirectly binds to an analyte in and/or on the deposited labeled cell; and (d) detecting, in the deposited labeled cell, a first signal associated with the first probe or a product thereof and a second signal associated with the second probe or a product thereof.

In any one or more of the preceding embodiments, the population of cells can comprise dissociated cells and/or nuclei. In any one or more of the preceding embodiments, the population of cells can be a population of cell nuclei. In any one or more of the preceding embodiments, the population of cells can comprise immune cells, such as neutrophils, eosinophils, basophils, mast cells, monocytes, granulocytes, macrophages, dendritic cells, natural killer cells, and/or lymphocytes (B cells and/or T cells). In any one or more of the preceding embodiments, the population of cells can comprise neuronal cells, such as glial cells, oligodendrocytes, astrocytes, intermediate progenitors, immature neurons, mature neurons, glutamatergic neurons, GABAergic neurons, dopaminergic neurons, cholinergic neurons, and/or motor neurons.

In any one or more of the preceding embodiments, the population of cells can be generated from a sample such as a tissue sample.

In any one or more of the preceding embodiments, the binding moiety can covalently bind to one or more molecules in and/or on the cell. In any one or more of the preceding embodiments, the binding moiety can bind to one or more molecules in and/or on the cell via a linker.

In any one or more of the preceding embodiments, the binding moiety can noncovalently bind to one or more molecules in and/or on the cell. In any one or more of the preceding embodiments, the binding moiety can bind to one or more molecules in and/or on the cell via a linker.

In any one or more of the preceding embodiments, the binding moiety can bind to a surface of the cell. In any one or more of the preceding embodiments, the binding moiety can comprise a polynucleotide or analog thereof, a polypeptide or analog thereof, a lipid or analog thereof, a carbohydrate or analog thereof, or a combination thereof. In any one or more of the preceding embodiments, the binding moiety can be selected from the group consisting of: an antibody or an epitope binding fragment thereof; a lipophilic moiety which is optionally cholesterol; a receptor; a receptor ligand; a small molecule; an aptamer; a monobody; an affimer; a darpin; and a protein scaffold.

In any one or more of the preceding embodiments, the labeling agent can further comprise a target-specific barcode sequence that identifies the labelling agent bound to the labeled cell. In any one or more of the preceding embodiments, the reporter oligonucleotide can further comprise the target-specific barcode sequence. In any one or more of the preceding embodiments, the target-specific barcode sequence and the sample-specific barcode sequence can at least partially overlap in sequence.

In any one or more of the preceding embodiments, the labeled cell may but does not need to be in a partition prior to, during, and/or after providing the population of cells comprising the labeled cell. In any one or more of the preceding embodiments, the labeled cell may but does not need to be in a partition during depositing the population of cells. In any one or more of the preceding embodiments, the partition can be an emulsion droplet or a microwell of a microwell array.

In any one or more of the preceding embodiments, the labeled cell may but does not need to be lysed prior to and/or during depositing the population of cells.

In any one or more of the preceding embodiments, a nucleic acid of the labeled cell may but does not need to be extended and/or reverse transcribed by a polymerase, ligated to another nucleic acid, amplified, and/or sequenced between providing the population of cells and depositing the population of cells. In any one or more of the preceding embodiments, the nucleic acid can be the reporter oligonucleotide or a cellular DNA or RNA molecule of the cell.

In any one or more of the preceding embodiments, a nucleic acid of the labeled cell may but does not need to be released from the cell between providing the population of cells and depositing the population of cells. In any one or more of the preceding embodiments, the nucleic acid can be the reporter oligonucleotide or a cellular DNA or RNA molecule of the cell.

In any one or more of the preceding embodiments, the first probe can hybridize to the sample-specific barcode sequence. In any one or more of the preceding embodiments, the first probe can comprise a detectable label, and detecting the first signal associated with the first probe can comprise detecting the detectable label. In any one or more of the preceding embodiments, the detectable label can be an optical label. In any one or more of the preceding embodiments, detecting the first signal associated with the first probe can comprise using imaging to detect the optical label.

In any one or more of the preceding embodiments, the first probe can be selected from the group consisting of: a probe comprising a 3' or 5' overhang upon hybridization to the sample-specific barcode sequence, optionally wherein the 3' or 5' overhang comprises one or more additional barcode sequences that identify the sample-specific barcode sequence; a probe comprising a 3' overhang and a 5' overhang upon hybridization to the sample-specific barcode sequence, optionally wherein the 3' overhang and the 5' overhang each independently comprises one or more additional barcode sequences that identify the sample-specific barcode sequence; a circular probe, optionally wherein the circular probe comprises one or more additional barcode sequences that identify the sample-specific barcode sequence; a circularizable probe or probe set, optionally wherein the circularizable probe or probe set comprises one or more additional barcode sequences that identify the sample-specific barcode sequence; a probe or probe set comprising a split hybridization region configured to hybridize to a splint, optionally wherein the split hybridization region comprises one or more additional barcode sequences; and a combination thereof, and optionally wherein detecting the first signal associated with the first probe comprises detecting at least a portion of the one or more additional barcode sequences.

In any one or more of the preceding embodiments, the method can further comprise hybridizing a first detectable probe to the first probe and/or generating a first product of the first probe and/or the first detectable probe. In any one or more of the preceding embodiments, the first product can be a hybridization product, a ligation product, an amplification product, or a combination thereof. In any one or more of the preceding embodiments, the first product can comprise a branched structure, a hybridization chain reaction (HCR) product, a linear-oligo hybridization chain reaction (LO-HCR), and/or a rolling circle amplification (RCA) product.

In any one or more of the preceding embodiments, the analyte can be or comprise a nucleic acid analyte. In any one or more of the preceding embodiments, the analyte can be or comprise a cellular RNA molecule. In any one or more of the preceding embodiments, the analyte can be or comprise a polypeptide.

In any one or more of the preceding embodiments, the binding moiety of the labeling agent may but does not need to bind to the analyte.

In any one or more of the preceding embodiments, the second probe can hybridize to a sequence in the analyte or in a probe targeting the analyte, optionally wherein the probe targeting the analyte is configured to directly or indirectly bind to the analyte, and optionally wherein the second probe comprises a detectable label, and optionally wherein detecting the second signal associated with the second probe comprises detecting the detectable label, optionally wherein the detectable label is an optical label, and optionally wherein detecting the second signal associated with the second probe comprises using imaging to detect the optical label.

In any one or more of the preceding embodiments, the second probe can be selected from the group consisting of: a probe comprising a 3' or 5' overhang upon hybridization to the sequence in the analyte or in the probe targeting the analyte, optionally wherein the 3' or 5' overhang comprises one or more additional barcode sequences that identify the analyte; a probe comprising a 3' overhang and a 5' overhang upon hybridization to the sequence in the analyte or in the probe targeting the analyte, optionally wherein the 3' overhang and the 5' overhang each independently comprises one or more additional barcode sequences that collectively identify the analyte; a circular probe, optionally wherein the circular probe comprises one or more additional barcode sequences that identify the analyte; a circularizable probe or probe set, optionally wherein the circularizable probe or probe set comprises one or more additional barcode sequences that identify the analyte; a probe or probe set comprising a split hybridization region configured to hybridize to a splint, optionally wherein the split hybridization region comprises one or more additional barcode sequences that identify the analyte; and a combination thereof, and optionally wherein detecting the second signal associated with the second probe comprises detecting at least a portion of the one or more additional barcode sequences.

In any one or more of the preceding embodiments, the method can further comprise hybridizing a second detectable probe to the second probe and/or generating a second product of the second probe and/or the second detectable probe.

In any one or more of the preceding embodiments, the second product can be a hybridization product, a ligation product, an amplification product, or a combination thereof, optionally wherein the second product comprises a branched structure, a hybridization chain reaction (HCR) product, a linear-oligo hybridization chain reaction (LO-HCR), and/or a rolling circle amplification (RCA) product.

In any one or more of the preceding embodiments, the method can further comprise comparing signals detected in the deposited labeled cell with signal(s) detected in one or more other cells in the population.

In any one or more of the preceding embodiments, the population can comprise at least about 100, at least about 1,000, at least about 10,000, at least about 50,000, at least about 100,000, or at least about 500,000 cells. In any one or more of the preceding embodiments, the, optionally wherein the cells are immobilized on the substrate within an area of about 0.1 $cm^2$, about 0.5 $cm^2$, about 1 $cm^2$, about 2 $cm^2$, about 5 $cm^2$, or about 10 $cm^2$, and optionally wherein at least about 100,000 cells are immobilized on the substrate within about 1 $cm^2$.

In any one or more of the preceding embodiments, the method can further comprise imaging the deposited labeled cell prior to, during, and/or after the detecting, optionally wherein the imaging comprises imaging a shape, a size, a morphological feature, and/or a marker of the deposited labeled cell or a portion thereof, optionally wherein the marker is a fluorescent marker.

In any one or more of the preceding embodiments, the deposited labeled cell can be fixed prior to the detecting.

In any one or more of the preceding embodiments, the method can but does not need to comprise introducing an exogenous polynucleotide into the cell in the population of cells prior to labeling the cell with the labeling agent comprising the sample-specific barcode sequence, or which does not comprise introducing an exogenous polynucleotide comprising a barcode sequence into the cell in the population of cells prior to labeling the cell with the labeling agent comprising the sample-specific barcode sequence.

In any one or more of the preceding embodiments, the exogenous polynucleotide can comprise or encode a gene, a modified/damaged/non-natural nucleotide or nucleotide analog, an overexpressed gene, an RNAi based system, a regulatory RNA, a non-coding RNA, an mRNA, a zinc finger nuclease, a transcription activator-like effector nuclease (TALEN), a meganuclease, a computationally designed protein, a computationally designed RNA, and/or a CRISPR-Cas system.

In any one or more of the preceding embodiments, the population of cells can be or comprise dissociated cells, a cell suspension, or nuclei.

In any one or more of the preceding embodiments, the method can be for cell analysis, comprising: (a) providing a population of cells comprising a labeled cell, wherein the labeled cell is labeled with a labeling agent comprising (i) a binding moiety and (ii) a reporter oligonucleotide comprising a first barcode region, and wherein the binding moiety is bound to the cell; (b) immobilizing the population of cells comprising the labeled cell on a substrate; (c) contacting the immobilized cells with: (i) a first probe that hybridizes to the first barcode region, and (ii) a second probe that directly or indirectly binds to an analyte in and/or on one or more of the immobilized cells, wherein the second probe comprises a second barcode region; and (d) detecting a first signal associated with the first probe or a product thereof and a second signal associated with the second probe or a product thereof on the substrate, thereby detecting the presence or absence of the analyte in the immobilized labeled cell.

In any one or more of the preceding embodiments, cells in the population may but do not need to be partitioned into partitions prior to, during, and/or after the providing of the population of cells or during the immobilizing of the population of cells. In any one or more of the preceding embodiments, the partitions can be or comprise emulsion droplets and/or microwells.

In any one or more of the preceding embodiments, the first barcode region can comprise a sample-specific barcode sequence corresponding to a sample from which the labeled cell is derived. In any one or more of the preceding embodiments, the first barcode region can comprise a target-specific barcode sequence corresponding to the binding moiety or target thereof. In any one or more of the preceding embodiments, the first barcode region can comprise a barcode sequence corresponding to a cell feature.

In any one or more of the preceding embodiments, the second barcode region can comprise a binding site for a detectable probe. In any one or more of the preceding embodiments, the detectable probe can comprise a fluorescently labeled probe. In any one or more of the preceding embodiments, the detectable probe can comprise an intermediate probe comprising a binding site for another detectable probe. In any one or more of the preceding embodiments, the binding site can be or comprise a barcode sequence. In any one or more of the preceding embodiments, the detectable probe can comprise a circular probe or circularizable probe or probe set, of which a rolling circle amplification (RCA) product comprises a plurality of binding sites for yet another detectable probe.

In any one or more of the preceding embodiments, the method can be for sample analysis, comprising: (a) contacting a first sample and a second sample with a first labeling agent and a second labeling agent, respectively, to provide labeled cells in each sample, wherein the first labeling agent and the second labeling agent each comprises (i) a binding moiety and (ii) a reporter oligonucleotide comprising a first barcode region comprising a sample-specific barcode sequence corresponding to the respective sample, wherein the binding moiety of each labeling agent binds to one or more dissociated cells in the respective sample; (b) combining labeled cells from the first and second samples; (c) immobilizing a population of cells comprising labeled cells from the first and second samples on a substrate; (d) contacting the immobilized cells with: (i) a first probe that hybridizes to the sample-specific barcode sequence corresponding to the first or second sample, and (ii) a second probe that directly or indirectly binds to an analyte in and/or on one or more of the immobilized cells, wherein the second probe comprises a second barcode region; and (e) detecting a first signal associated with the first probe or a product thereof and a second signal associated with the second probe or a product thereof on the substrate, thereby detecting the presence or absence of the analyte in one or more cells from the first sample and/or from the second sample.

In any one or more of the preceding embodiments, the first sample and/or the second sample can comprise dissociated cells.

In any one or more of the preceding embodiments, the method can be for sample analysis, comprising: (a) contacting a first sample and a second sample with a first labeling agent and a second labeling agent, respectively, to provide labeled cells in each sample, wherein the first labeling agent and the second labeling agent each comprises (i) a binding moiety and (ii) a reporter oligonucleotide comprising a first barcode region comprising a sample-specific barcode sequence corresponding to the respective sample, wherein the binding moiety of each labeling agent binds to one or more cells in the respective sample; (b) combining the first and second samples; (c) immobilizing a population of dissociated cells comprising labeled cells from the first and second samples on a substrate; (d) contacting the immobilized cells with: (i) a first probe that hybridizes to the sample-specific barcode sequence corresponding to the first or second sample, and (ii) a second probe that directly or indirectly binds to an analyte in and/or on one or more of the immobilized cells, wherein the second probe comprises a second barcode region; and (e) detecting a first signal associated with the first probe or a product thereof and a second signal associated with the second probe or a product thereof on the substrate, thereby detecting the presence or absence of the analyte in one or more cells from the first sample and/or from the second sample.

In any one or more of the preceding embodiments, the first and second samples can be combined prior to processing the first and second samples to provide the population of dissociated cells.

In any one or more of the preceding embodiments, the first and second samples can be processed separately to provide dissociated cells prior to combining the dissociated cells to provide the population of dissociated cells.

In any one or more of the preceding embodiments, the first probe and/or the second barcode region can comprise one or more barcode sequences. In any one or more of the preceding embodiments, the first probe and/or the second probe can be a circularizable probe.

In any one or more of the preceding embodiments, the first signal and/or the second signal can be associated with a rolling circle amplification (RCA) product of a circularized probe comprising a sequence of the circularizable probe, wherein the RCA product comprises multiple copies of the complement of the one or more barcode sequences, and wherein the first signal and/or the second signal is detected using a detectable probe that hybridizes to the complement. In any one or more of the preceding embodiments, the detectable probe can be detectably labeled or comprise a sequence that hybridizes to a detectably labeled probe.

In any one or more of the preceding embodiments, the method can comprise detecting signals associated with the one or more barcode sequences in sequential cycles using a plurality of detectable probes (e.g., probes that hybridize to an RCA product or probes that hybridize to intermediate probes that hybridize to an RCA product), thereby detecting the presence or absence of the analyte in one or more cells from the first sample and/or from the second sample.

In any one or more of the preceding embodiments, the method can be for sample analysis, comprising: (a) contacting a first population of cells with a first labeling agent to provide a first plurality of labeled cells and contacting a second population of cells with a second labeling agent to provide a second plurality of labeled cells, wherein the first labeling agent comprises (i) a first binding moiety and (ii) a first reporter oligonucleotide comprising a first sample-specific barcode sequence that identifies the first population of cells, wherein the second labeling agent comprises (i) a second binding moiety and (ii) a second reporter oligonucleotide comprising a second sample-specific barcode sequence that identifies the second population of cells; (b) pooling cells from the first plurality of labeled cells and the second plurality of labeled cells to provide a pooled plurality of labeled cells; (c) immobilizing the pooled plurality of labeled cells on a substrate; (d) contacting the immobilized cells with: (i) a first probe that hybridizes to the first sample-specific barcode sequence corresponding to the first or second sample, (ii) a second probe that hybridizes to the second sample-specific barcode sequence corresponding to the first or second sample, and (iii) a third probe or probe set that directly or indirectly binds to one or more analytes in and/or on one or more of the immobilized cells; and (e) detecting: (i) the first probe to identify the first sample-specific barcode sequence; (ii) the second probe to identify the second sample-specific barcode sequence; and (iii) the third probe or probe set to identify the one or more analytes in and/or on one or more of the immobilized cells; and (f) using the first sample-specific barcode sequence to identify cells from the first population of cells and the second sample-specific barcode sequence to identify cells from the second population of cells.

In any one or more of the preceding embodiments, the first and/or second binding moiety can covalently bind to one or more molecules in and/or on a cell of the first or second population of cells, optionally wherein the first and/or second binding moiety binds to one or more molecules in and/or on a cell of the first or second population of cells via a linker.

In any one or more of the preceding embodiments, the first and/or second binding moiety can noncovalently bind to one or more molecules in and/or on a cell of the first or second population of cells, optionally wherein the first and/or second binding moiety binds to one or more molecules in and/or on a cell of the first or second population of cells via a linker.

In any one or more of the preceding embodiments, the first and/or second binding moiety can bind to a surface of a cell of the first or second population of cells. In any one or more of the preceding embodiments, the binding moiety can be selected from the group consisting of: an antibody or an epitope binding fragment thereof; a lipophilic moiety which is optionally cholesterol; a receptor; a receptor ligand; a small molecule; an aptamer; a monobody; an affimer; a darpin; and a protein scaffold.

In any one or more of the preceding embodiments, the first plurality of labeled cells and the second plurality of labeled cells may but do not need to be in a partition. In any one or more of the preceding embodiments, the partition can be or comprise an emulsion droplet or a microwell of a microwell array.

In any one or more of the preceding embodiments, the first plurality of labeled cells and the second plurality of labeled cells may but do not need to be lysed prior to and/or during the immobilization of the pooled plurality of labeled cells on the substrate.

In any one or more of the preceding embodiments, the first probe can comprise a first detectable label and wherein detecting the first probe comprises detecting the first detectable label, optionally wherein the first detectable label is an first optical label, and optionally wherein detecting the first probe comprises using imaging to detect the first optical label. In any one or more of the preceding embodiments, the second probe can comprise a second detectable label and wherein detecting the second probe comprises detecting the second detectable label, optionally wherein the second detectable label is a second optical label, and optionally wherein detecting the second probe comprises using imaging to detect the second optical label.

In any one or more of the preceding embodiments, the one or more analytes can be or comprise one or more nucleic acid analytes. In any one or more of the preceding embodiments, the one or more nucleic acid analytes can be or comprise cellular RNA molecules. In any one or more of the preceding embodiments, the one or more analytes can be or comprise one or more polypeptides.

In any one or more of the preceding embodiments, the third probe or probe set can comprise: a probe comprising a 3' or 5' overhang upon hybridization to a sequence in an analyte of the one or more analytes, optionally wherein the 3' or 5' overhang comprises one or more additional barcode sequences that identify the analyte; a probe comprising a 3' overhang and a 5' overhang upon hybridization to a sequence in an analyte of the one or more analytes, optionally wherein the 3' overhang and the 5' overhang each independently comprises one or more additional barcode sequences that collectively identify the analyte; a circular probe that hybridizes to an analyte of the one or more analytes, optionally wherein the circular probe comprises one or more additional barcode sequences that identify the analyte; a circularizable probe or probe set that hybridizes to an analyte of the one or more analytes, optionally wherein the circularizable probe or probe set comprises one or more additional barcode sequences that identify the analyte; a probe or probe set comprising a split hybridization region configured to hybridize to a splint; or any combinations thereof, and optionally wherein detecting the third probe or probe set comprises detecting at least a portion of the one or more additional barcode sequences.

In any one or more of the preceding embodiments, the first and/or second population of cells can each comprise at least about 100, at least about 1,000, at least about 10,000, at least about 50,000, at least about 100,000, or at least about 500,000 dissociated cells, optionally wherein the pooled plurality of labeled cells are immobilized on the substrate within an area of about 0.1 $cm^2$, about 0.5 $cm^2$, about 1 $cm^2$, about 2 $cm^2$, about 5 $cm^2$, or about 10 $cm^2$, and optionally wherein at least about 100,000 cells of the pooled plurality of labeled cells are immobilized on the substrate within about 1 $cm^2$.

In any one or more of the preceding embodiments, the method can further comprise imaging at least some of the immobilized cells prior to, during, and/or after the detecting in (e), optionally wherein the imaging comprises imaging a shape, a size, a morphological feature, and/or a marker of the immobilized cells, optionally wherein the marker is a fluorescent marker.

In any one or more of the preceding embodiments, the immobilized cells can be fixed prior to the detecting.

In any one or more of the preceding embodiments, the method may but does not need to comprise introducing an exogenous polynucleotide into cells of the first or second population of cells prior to the contacting, or which does not comprise introducing an exogenous polynucleotide comprising a barcode sequence into cells of the first or second population of cells prior to the contacting. In any one or more of the preceding embodiments, the exogenous polynucleotide can comprise or encode a gene, a modified/damaged/non-natural nucleotide or nucleotide analog, an overexpressed gene, an RNAi based system, a regulatory RNA, a non-coding RNA, an mRNA, a zinc finger nuclease, a transcription activator-like effector nuclease (TALEN), a meganuclease, a computationally designed protein, a computationally designed RNA, and/or a CRISPR-Cas system.

In any one or more of the preceding embodiments, a method herein can comprise: (a) providing a population of cells comprising a labeled cell, wherein the cell is labeled with a labeling agent comprising a binding moiety and a reporter oligonucleotide, and wherein the binding moiety is bound to the cell (e.g., the binding moiety is covalently or noncovalently bound to one or more molecules in and/or on the cell); (b) immobilizing the labeled cell on a substrate; (c) contacting the immobilized labeled cell with: (i) a first probe that binds to the labeling agent, and (ii) a second probe that binds to an analyte in and/or on the immobilized labeled cell; and (d) detecting a first signal associated with the first probe or a product thereof and a second signal associated with the second probe or a product thereof in the immobilized labeled cell. In some embodiments, the first probe binds to the binding moiety of the labeling agent. In some embodiments, the first probe binds to the reporter oligonucleotide of the labeling agent. In some embodiments, the first probe binds to the binding moiety and the reporter oligonucleotide. In some embodiments, the first probe is a sample identification probe, which is a detectable probe for identifying a sample from which the labeled cell is derived. In some embodiments, the second probe is an analyte detection probe, which is a detectable probe for detecting an analyte of interest in the population of cells comprising cells from different samples.

In any one or more of the preceding embodiments, the cell can be labeled with a sample-specific barcode sequence corresponding to a sample from which the labeled cell is derived. The sample-specific barcode sequence can be comprised in the labeling agent. For instance, the sample-specific barcode sequence can be comprised in the reporter oligonucleotide. As an alternative or addition to the labeling agent comprising a sample-specific barcode sequence, a molecule or complex separate from the labeling agent can comprise another sample-specific barcode sequence that is the same or different in sequence compared to the sample-specific barcode sequence. For instance, the sample-specific barcode sequence can be comprised in a separate labeling agent that labels the same cell as the labeling agent.

In any one or more of the preceding embodiments, a method herein can comprise (a) providing a population of cells comprising a labeled cell, wherein the cell is labeled with a labeling agent comprising a binding moiety and a reporter oligonucleotide, and wherein the binding moiety is bound to the cell; (b) immobilizing the labeled cell on a substrate; (c) contacting the immobilized labeled cell with (i) a first probe that binds to the labeling agent, e.g., the binding moiety and/or the reporter oligonucleotide, and (ii) a second probe that binds to an analyte in and/or on the immobilized labeled cell; and (d) detecting a first signal associated with the first probe or a product thereof and a second signal associated with the second probe or a product thereof in the immobilized labeled cell, wherein the reporter oligonucleotide of the labeling agent comprises a sample-specific barcode sequence corresponding to a sample from which the labeled cell is derived.

In any one or more of the preceding embodiments, a method herein can comprise (a) providing a population of cells comprising a labeled cell, wherein the cell is labeled with a labeling agent comprising a binding moiety and a reporter oligonucleotide, and wherein the binding moiety is bound to the cell; (b) immobilizing the labeled cell on a substrate; (c) contacting the immobilized labeled cell with (i) a first probe that binds to the binding moiety and/or the reporter oligonucleotide, and (ii) a second probe that binds to an analyte in and/or on the immobilized labeled cell; and (d) detecting a first signal associated with the first probe or a product thereof and a second signal associated with the second probe or a product thereof in the immobilized labeled cell, wherein the first probe is a sample identification probe for identifying a sample from which the labeled cell is derived and the first signal is associated with sample identity, whereas the second probe is an analyte detection probe for detecting an analyte of interest across cells or cell populations pooled from different samples.

In any one or more of the preceding embodiments, the binding moiety can covalently or noncovalently bind to one or more molecules in and/or on the cell. In some embodiments, the binding moiety can bind to the one or more molecules via a linker. In some embodiments, the binding moiety can bind to a surface of the cell or can be internal to the cell.

In any one or more of the preceding embodiments, the binding moiety can comprise a polynucleotide or analog thereof, a polypeptide or analog thereof, a lipid or analog thereof, a carbohydrate or analog thereof, or a combination thereof. In any one or more of the preceding embodiments, the binding moiety can be selected from the group consisting of an antibody or an epitope binding fragment thereof, a lipophilic moiety, a receptor, a receptor ligand, a small molecule, an aptamer, a monobody, an affimer, a darpin, and a protein scaffold. In some embodiments, the lipophilic moiety is cholesterol.

In any one or more of the preceding embodiments, the first probe can bind to the reporter oligonucleotide or a sequence thereof. In any one or more of the preceding embodiments, the reporter oligonucleotide can comprise a target-specific barcode sequence corresponding to the binding moiety (of the labeling agent) or target thereof. In any one or more of the preceding embodiments, the target-specific barcode sequence can be in the reporter oligonucleotide. In any one or more of the preceding embodiments, the target-specific barcode sequence and the sample-specific barcode sequence may at least partially overlap in sequence. In some embodiments, the target-specific barcode sequence and the sample-specific barcode sequence do not overlap. In some embodiments, the target-specific barcode sequence and the sample-specific barcode sequence are the same barcode sequence. In some embodiments, the target-specific barcode sequence and the sample-specific barcode sequence are distinct barcode sequences.

In any one or more of the preceding embodiments, the labeled cell may not need to be in a partition prior to, during, and/or after the providing step in (a) or during the immobilizing in step (b), optionally wherein the partition is an emulsion droplet or a microwell. In some embodiments, the cell is not partitioned in a partition (e.g., an emulsion droplet or a microwell) prior to, during, and/or after being labeled with the labeling agent. In some embodiments, the partition is an emulsion droplet or a microwell. In some embodiments, the labeled cell is not partitioned in a partition (e.g., an emulsion droplet or a microwell) throughout the providing step, the immobilizing step, the contacting step, and/or the detecting step.

In any one or more of the preceding embodiments, the labeled cell may not need to be lysed or homogenized prior to and/or during the immobilizing in step (b). In some embodiments, the cell is not lysed or homogenized prior to, during, and/or after being labeled with the labeling agent. In some embodiments, the labeled cell is not lysed or homogenized throughout the providing step, the immobilizing step, the contacting step, and/or the detecting step, although the labeled cell may be permeabilized, fixed, crosslinked/decrosslinked, embedded in a matrix, cleared, and/or otherwise treated.

In any one or more of the preceding embodiments, a nucleic acid of the labeled cell may not need to be extended and/or reverse transcribed by a polymerase, ligated to another nucleic acid, amplified, and/or sequenced between the providing step (a) and the immobilizing in step (b). In any one or more of the preceding embodiments, the nucleic acid is the reporter oligonucleotide or a cellular DNA or RNA molecule of the cell. In some embodiments, the reporter oligonucleotide is not extended and/or reverse transcribed by a polymerase, ligated to another nucleic acid, amplified, and/or sequenced, in order for the labeling agent to be detected. In some embodiments, the cellular DNA or RNA molecule of the cell is not extended and/or reverse transcribed by a polymerase, ligated to another nucleic acid, amplified, and/or sequenced, in order for the analyte to be detected.

In any one or more of the preceding embodiments, a nucleic acid of the labeled cell may not need to be released from the cell between the providing step (a) and the immobilizing in step (b). In some embodiments, the nucleic acid is the reporter oligonucleotide or a cellular DNA or RNA molecule of the cell. In some embodiments, the reporter oligonucleotide is not released from the cell, in order for the labeling agent to be detected. In some embodiments, the cellular DNA or RNA molecule of the cell is not released from the cell, in order for the analyte to be detected.

In any one or more of the preceding embodiments, the first probe can hybridize to a sequence in the reporter oligonucleotide. In any one or more of the preceding embodiments, the first probe can be detectably labeled.

In any one or more of the preceding embodiments, the first probe can be selected from the group consisting of: a probe comprising a 3' or 5' overhang upon hybridization to the sequence in the reporter oligonucleotide; a probe comprising a 3' overhang and a 5' overhang upon hybridization to the sequence in the reporter oligonucleotide; a circular probe; a circularizable probe or probe set; a probe or probe set comprising a split hybridization region configured to hybridize to a splint; and a combination thereof. In some embodiments, the 3' or 5' overhang comprises one or more barcode sequences. In some embodiments, the 3' and the 5' overhang independently comprises one or more barcode sequences. In some embodiments, the split hybridization region comprises one or more barcode sequences.

In any one or more of the preceding embodiments, the method can further comprise hybridizing a first detectable probe to the first probe and/or generating a first product of the first probe and/or the first detectable probe. In any one or more of the preceding embodiments, the first product can be a hybridization product, a ligation product, an amplification product, or a combination thereof. In some embodiments, the first product can comprise a branched structure, a hybridization chain reaction (HCR) product, a linear-oligo hybridization chain reaction (LO-HCR), and/or a rolling circle amplification (RCA) product. In any one or more of the preceding embodiments, the first signal can be associated with the first product and can be detected in situ.

In any one or more of the preceding embodiments, the analyte can be a nucleic acid analyte or a non-nucleic acid analyte. In any one or more of the preceding embodiments, the binding moiety of the labeling agent may but does not need to bind to the analyte.

In any one or more of the preceding embodiments, the second probe can hybridize to a sequence in the analyte. In any one or more of the preceding embodiments, the second probe can hybridize to a sequence in a probe targeting the analyte or a product of the probe targeting the analyte. For instance, the second probe can be a detectable probe capable of hybridizing to a rolling circle amplification product of a circularizable probe or probe set that hybridizes to a cellular nucleic acid (e.g., genomic DNA, mRNA, or cDNA) or a reporter oligonucleotide of a probe that binds a nucleic acid or non-nucleic acid analyte. In some embodiments, the probe targeting the analyte is configured to directly or indirectly bind to the analyte. In any one or more of the preceding embodiments, the second probe can be detectably labeled.

In any one or more of the preceding embodiments, the second probe can be selected from the group consisting of: a probe comprising a 3' or 5' overhang upon hybridization to the sequence in the analyte or in the probe targeting the analyte; a probe comprising a 3' overhang and a 5' overhang upon hybridization to the sequence in the analyte or in the probe targeting the analyte; a circular probe; a circularizable probe or probe set; a probe or probe set comprising a split hybridization region configured to hybridize to a splint; and a combination thereof. In some embodiments, the 3' or 5' overhang comprises one or more barcode sequences. In some embodiments, the 3' overhang and the 5' overhang each independently comprises one or more barcode sequences. In some embodiments, the split hybridization region comprises one or more barcode sequences.

In any one or more of the preceding embodiments, the method can further comprise hybridizing a second detectable probe to the second probe and/or generating a second product of the second probe and/or the second detectable probe.

In any one or more of the preceding embodiments, the second product can be a hybridization product, a ligation product, an amplification product, or a combination thereof. In some embodiments, the second product comprises a branched structure, a hybridization chain reaction (HCR) product, a linear-oligo hybridization chain reaction (LO-HCR), and/or a rolling circle amplification (RCA) product. In any one or more of the preceding embodiments, the second signal can be associated with the second product and is detected in situ.

In any one or more of the preceding embodiments, the method can further comprise comparing signals detected in the immobilized labeled cell with signal(s) detected in one or more other cells in the population of cells. In some embodiments, the one or more other cells in the population of cells are on the same substrate as the immobilized labeled cell. In some embodiments, the immobilized labeled cell and the one or more other cells are from the same sample. In some embodiments, the immobilized labeled cell and the one or more other cells are from different samples.

In any one or more of the preceding embodiments, the population of cells can comprise cells derived from multiple different samples. In any one or more of the preceding embodiments, the population can comprise at least about 100, at least about 1,000, at least about 10,000, at least about 50,000, at least about 100,000, or at least about 500,000 dissociated cells. In any one or more of the preceding embodiments, the dissociated cells can be immobilized on the substrate within an area of about 0.1 $cm^2$, about 0.5 $cm^2$, about 1 $cm^2$, about 2 $cm^2$, about 5 $cm^2$, or about 10 $cm^2$. In some embodiments, the population of cells comprises at least about 100,000 dissociated cells which are immobilized on the substrate within about 1 $cm^2$. In any one or more of the preceding embodiments, the dissociated cells can be from two, three, four, five, six, seven, eight, nine, ten, or more different samples, and the sample origin of a dissociated cell can be identified on an in situ platform, for instance, by detecting a sample-specific barcode sequence in a labeling agent in and/or on the dissociated cell immobilized on the substrate.

In any one or more of the preceding embodiments, the method can further comprise imaging the immobilized labeled cell prior to, during, and/or after the detecting step (d). In some embodiments, the imaging can comprise imaging a shape, a size, a morphological feature, and/or a marker of the immobilized labeled cell or a portion thereof. In some embodiments, the marker can be a fluorescent marker.

In some embodiments according to any one of the methods described herein, the immobilized labeled cell can be live or fixed prior to the detecting step (d).

In any one or more of the preceding embodiments, a method herein can be for cell analysis, comprising (a) providing a population of cells comprising a labeled cell, wherein the cell is labeled with a labeling agent comprising (i) a binding moiety and (ii) a reporter oligonucleotide comprising a first barcode region, and wherein the binding moiety is bound to the cell; (b) immobilizing the population of cells comprising the labeled cell on a substrate; (c) contacting the immobilized cells with (i) a first probe that hybridizes to the first barcode region, and (ii) a second probe that binds to an analyte in and/or on one or more of the immobilized cells, wherein the second probe can comprise a second barcode region; and (d) detecting a first signal associated with the first probe or a product thereof and a second signal associated with the second probe or a product thereof on the substrate, thereby detecting the presence or absence of the analyte in the immobilized labeled cell.

In any one or more of the preceding embodiments, cells in the population do not need to be partitioned into partitions prior to, during, and/or after the providing step in (a) or during the immobilizing in step (b). In some embodiments, the partitions can be emulsion droplets and/or microwells. In some embodiments, cells in the population are not partitioned in a partition (e.g., an emulsion droplet or a microwell) prior to, during, and/or after being labeled with labeling agents. In some embodiments, cells in the population are not partitioned in a partition (e.g., an emulsion droplet or a microwell) throughout the providing step, the immobilizing step, the contacting step, and/or the detecting step.

In any one or more of the preceding embodiments, the first barcode region can comprise a sample-specific barcode sequence corresponding to a sample from which the labeled cell is derived. In some embodiments, the first barcode region can comprise (i) a sample-specific barcode sequence corresponding to a sample from which the labeled cell is derived, and (ii) a target-specific barcode sequence corresponding to the binding moiety or target thereof. In some embodiments, the first barcode region can comprise (iii) a barcode sequence corresponding to a cell feature. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof. As such, the labeling agent can be used to identify the sample from which the labeled cell is derived. In some aspects, the labeling agent can be used to identify the binding moiety or target of the labeling agent. In some aspects, the labeling agent can be used to identify a cell feature of the labeled cell.

In any one or more of the preceding embodiments, the second barcode region can comprise a binding site for a detectable probe. In some embodiments, the detectable probe can comprise (i) a fluorescently labeled probe, (ii) an intermediate probe comprising a binding site for another detectable probe, and/or (iii) a circular probe or circularizable probe or probe set, of which a rolling circle amplification (RCA) product can comprise a plurality of binding sites for yet another detectable probe. In some embodiments, the binding site of the intermediate probe can be or comprise a barcode sequence.

In any one or more of the preceding embodiments, a method herein can be for sample analysis, comprising (a) contacting a first sample and a second sample with a first labeling agent and a second labeling agent, respectively, to provide labeled cells in each sample, wherein the first labeling agent and the second labeling agent each can comprise (i) a binding moiety and (ii) a reporter oligonucleotide comprising a first barcode region comprising a sample-specific barcode sequence corresponding to the respective sample, wherein the binding moiety of each labeling agent binds to one or more dissociated cells in the respective sample; (b) combining labeled cells from the first and second samples; (c) immobilizing a population of cells comprising labeled cells from the first and second samples on a substrate; (d) contacting the immobilized cells with (i) a first probe that hybridizes to the sample-specific barcode sequence corresponding to the first or second sample, and (ii) a second probe that binds to an analyte in and/or on one or more of the immobilized cells, wherein the second probe comprises a second barcode region; and (e) detecting a first signal associated with the first probe or a product thereof and a second signal associated with the second probe or a product thereof on the substrate, thereby detecting the presence or absence of the analyte in one or more cells from the first sample and/or from the second sample. In some embodiments, the first sample and/or the second sample can comprise dissociated cells.

In any one or more of the preceding embodiments, a method herein can be for sample analysis, comprising (a) contacting a first sample and a second sample with a first labeling agent and a second labeling agent, respectively, to provide labeled cells in each sample, wherein the first labeling agent and the second labeling agent each can comprise (i) a binding moiety and (ii) a reporter oligonucleotide comprising a first barcode region comprising a sample-specific barcode sequence corresponding to the respective sample, wherein the binding moiety of each labeling agent binds to one or more cells in the respective sample; (b) combining the first and second samples; (c) immobilizing a population of dissociated cells comprising labeled cells from the first and second samples on a substrate; (d) contacting the immobilized cells with: (i) a first probe that hybridizes to the sample-specific barcode sequence corresponding to the first or second sample, and (ii) a second probe that binds to an analyte in and/or on one or more of the immobilized cells, wherein the second probe can comprise a second barcode region; and (e) detecting a first signal associated with the first probe or a product thereof and a second signal associated with the second probe or a product thereof on the substrate, thereby detecting the presence or absence of the analyte in one or more cells from the first sample and/or from the second sample. In some embodiments, the first and second samples can be combined in (b) prior to processing the first and second samples to provide the population of dissociated cells in (c). In some embodiments, the first and second samples can be processed separately to provide dissociated cells prior to combining the dissociated cells in (b) to provide the population of dissociated cells in (c).

In any one or more of the preceding embodiments, the first probe and/or the second barcode region can comprise one or more barcode sequences. In some embodiments, the first probe and/or the second probe can be a circularizable probe.

In any one or more of the preceding embodiments, the first signal and/or the second signal can be associated with a rolling circle amplification (RCA) product of a circularized probe comprising a sequence of the circularizable probe, wherein the RCA product can comprise multiple copies of the complement of the one or more barcode sequences, and wherein the first signal and/or the second signal can be detected using a detectable probe that hybridizes to the complement. In some embodiments, the detectable probe can be detectably labeled or can comprise a sequence that can hybridize to a detectably labeled probe.

In any one or more of the preceding embodiments, a method herein can comprise detecting signals associated with the one or more barcode sequences in sequential cycles using a plurality of detectable probes, thereby detecting the presence or absence of the analyte in one or more cells from the first sample and/or from the second sample.

In any one or more of the preceding embodiments, the second probe can: (i) bind directly or indirectly to an analyte (e.g., a nucleic acid analyte or protein analyte) in and/or on one or more of the immobilized cells, and (ii) comprise a nucleic acid tag which may comprise the second barcode region. The second signal can be detected by detecting: (i) the nucleic acid tag of the second probe, (ii) a product (e.g., an RCA product) of the nucleic acid tag, (iii) a probe or probe set that hybridizes to the nucleic acid tag, e.g., at the second barcode region, and (iv) a product (e.g., an RCA product) of the probe or probe set that hybridizes to the nucleic acid tag.

In any one or more of the preceding embodiments, cell nuclei can be isolated from cells and labeled with the labeling agents and detected on an in situ platform as described herein. In any one or more of the preceding embodiments, the population of cells and/or nuclei can be in a suspension prior to labeling with the labeling agent. In any one or more of the preceding embodiments, a suspension containing the population of cells and/or nuclei can be obtained from a sample labeled with the labeling agent.

DETAILED DESCRIPTION

Figure 1:
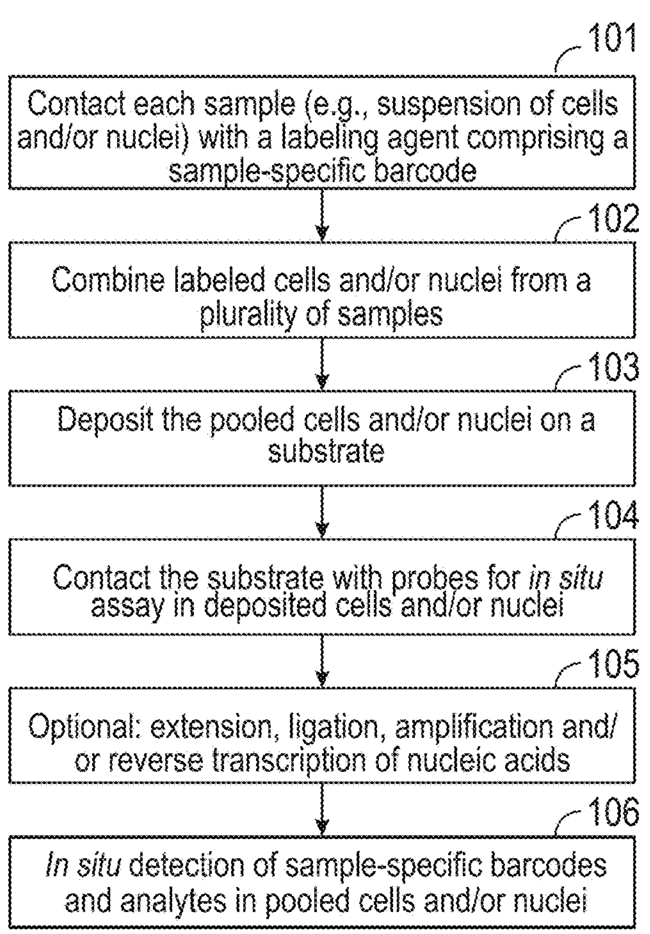
FIG. 1 shows an exemplary workflow comprising analyzing labeled single cells on a substrate using an in situ assay platform.

Provided herein in some aspects are multiplexed assays using a microscopy readout (e.g., optical detection of a barcode sequence of a probe directly or indirectly bound to an analyte), for example, for analyzing a plurality of analytes in dissociated cells in situ. In some embodiments, the dissociated cells are from different samples and the method comprises labeling cells with labeling agents comprising sample-specific barcodes and pooling the labeled cells from multiple biological samples onto a substrate for detecting analytes in the labeled cells in situ. The sample-specific barcodes can be analyzed in situ in the labeled cells on the substrate to trace the origins of single cells back to the samples prior to pooling. In addition, the labeled cells can be analyzed under a microscope for cell morphology, size, one or more biomarkers (e.g., proteins, nucleic acids, lipids, carbohydrates, etc.), genetic and genomic structures, gene expression, and/or one or more additional cellular features. For instance, expression and spatial information of one or more mRNA species in a labeled cell can be detected in situ in the cell and correlated with the sample origin and optionally one or more other features of that cell. Methods, compositions, kits, devices, and systems for these single-cell in situ assays, including genomics and transcriptomic assays, are provided. In some embodiments, the methods provided are quantitative at single-cell resolution without partitioning. Also provided herein are compositions and methods for detecting and/or quantifying nucleic acids in cells, tissues, organs or organisms. In some embodiments, the present disclosure provides methods for high-throughput profiling of a large number of cells, a large number of different samples from which the cells are derived, and/or a large number of analytes in situ, e.g., without the need to partition a population of cells into individual partitions (e.g., emulsion droplets or microwell arrays) in order to carry out the high-throughput multiplex profiling.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Provided herein in some aspects is an in situ platform for analyzing cells and cell populations such as dissociated cells, including blood samples and cell lines, e.g., for genomic analysis, transcriptomic analysis, analysis of proteins and interactions, and other applications. In some embodiments, the methods, compositions, kits, and systems provided herein can offer at least some advantages over existing single-cell assays, e.g., the ability to perform higher cell throughput at a lower cost per cell, and the ability to add layers of additional phenotypic information to molecular information, such as cell shape and/or expression of certain markers.

Cells and/or nuclei can be packed relatively tightly on a substrate per unit area (e.g., about 100,000 cells per $cm^2$) for in situ analysis by imaging the cells and/or nuclei to analyze molecular information within cells and/or nuclei from different samples. Each sample can independently comprise a relatively homogenous population (e.g., cells of a cell line, or cells purified or enriched based on particular marker(s)), a mixture of multiple populations (e.g., multiple cell lines), or a heterogenous population of cells (e.g., multiple different cell types or cells with different mutations from an organ or a tissue, such as cancer tissues). Cells and/or nuclei from the same sample can share a common sample-specific barcode sequence, such that cells and/or nuclei from multiple samples can be pooled, analyzed by imaging, and demultiplexed. In some embodiments, the methods and compositions provided herein offer cost effective methods of analysis by pooling cells and/or nuclei and cell populations from multiple different biological samples. In some embodiments, cells pooled from multiple different biological samples can be immobilized onto a single substrate and analyzed in one or more rounds of in situ analysis.

In some embodiments, cells and/or nuclei and cell populations from multiple different biological samples can be stained prior with multiplexing reagents, such as labeling agents, prior to pooling. In some embodiments, the labeling agents can comprise a detection component, such as a DNA oligonucleotide comprising a sample-specific barcode sequence. The sample-specific barcode sequence can be directly detected in the cell sample, as opposed to other methods involving nucleic acid isolation/purification, amplification, and sequencing (e.g., on a next generation sequencing platform). In some embodiments, the sample-specific barcode sequence can be detected by hybridization of detectably-labeled complementary probes, such as a fluorophore-linked complementary probes. In some embodiments, the labeling agents may further comprise a binding component or a binding moiety, such as antibody, lipid or aptamer. In some embodiments, the binding moiety can bind to the surface of the cell, or can be absorbed into the cell. In some embodiments, the labeled cells can be combined together and immobilized onto a substrate, such a glass slide, for in situ measurements.

In some embodiments, the labeled immobilized cells can be imaged upfront to acquire information, including non-molecular (e.g., phenotypic) or sub-cellular profiles. In some embodiments, the labeled immobilized cells can be imaged at the end of the in situ analysis. In some embodiments, the in situ analysis includes detecting the sample-specific barcode sequence, by methods such as in situ hybridization and/or in situ sequencing (e.g., in situ sequencing by synthesis or in situ sequencing by ligation), in the first round(s) to identify the location of the cell on the substrate and the biological samples from which the cell was derived. In some embodiments, the in situ analysis comprises further rounds of analysis and de-multiplexing to capture additional molecular information, such as presence of target genes or level of gene expression, and to associate the molecular information to the samples from which the cells were derived. In some embodiments, sample de-multiplexing comprises associating the detected signals indicative of sample-specific barcode sequences on an in situ platform with the samples of origin of the cells labeled with the sample-specific barcode sequences.

In some embodiments, the method comprises generating a signal code sequence at one or more locations in the dissociated cells on the substrate, the signal code sequence comprising signal codes corresponding to the signals (or absence thereof) associated with detectable probes for in situ hybridization that are sequentially hybridized to the dissociated cells, wherein the signal code sequence corresponds to a reporter oligonucleotide (which identifies the sample origin of a dissociated cell labeled with the reporter oligonucleotide) or an analyte in the dissociated cells, thereby detecting the analyte at the one or more of the multiple locations in the dissociated cells and identifying the sample origins of the dissociated cells.

In some embodiments, provided herein is a method for cell analysis, comprising (a) providing a population of cells comprising a labeled cell, wherein the cell is labeled with a labeling agent comprising a binding moiety and a reporter oligonucleotide, and wherein the binding moiety is bound to the cell; (b) immobilizing the labeled cell on a substrate; (c)

contacting the immobilized labeled cell with: (i) a first probe that binds to the labeling agent, and (ii) a second probe that binds to an analyte in and/or on the immobilized labeled cell; and (d) detecting a first signal associated with the first probe or a product thereof and a second signal associated with the second probe or a product thereof in the immobilized labeled cell, wherein the labeling agent comprises a sample-specific barcode sequence corresponding to a sample from which the labeled cell is derived. The first signal can be detected by a detectable probe that hybridizes to the sample-specific barcode sequence, and the second signal can be detected by a detectable probe that hybridizes to the second probe or a product (e.g., a rolling circle amplification product or a hybridization chain reaction complex) of the second probe. The first signal can be used to identify the sample from which the labeled cell is derived, and the second signal may be used to detect and/or decode the analyte in and/or on the immobilized labeled cell. In some embodiments, sequential hybridization of detectable probes can be used to (i) identify the samples from which the labeled single cells are derived and/or (ii) detect multiple analytes in and/or on the labeled single cells. Any suitable detection/decoding methods can be used, and exemplary methods comprising sequential hybridization of detectable probes are described in US 2019/0161796, US 2020/0224244, US 2022/0010358, US 2021/0340618, and WO 2021/138676, all of which are incorporated herein by reference.

In one aspect, provided herein is a method that comprises an in situ assay for one or more analytes of interest in one or more cells deposited and/or immobilized on a substrate. In some embodiments, the assay comprises analyzing the presence/absence, distribution, location, amount, level, expression, or activity of analytes (e.g., nucleic acid molecules) in one or more single cells in situ. Analytes can include nucleic acid molecules and non-nucleic acid molecules, such as proteins and peptides. Nucleic acid molecules can be derived from or analyzed in any specific type of cell and/or a specific sub-cellular region, e.g., from cytosol, from cell nuclei, from mitochondria, from microsomes, and more generally, from any other compartment, organelle, or portion of a cell. Examples comprise DNA analytes such as genomic DNA, methylated DNA, specific methylated DNA sequences, fragmented DNA, mitochondrial DNA, and RNA/DNA hybrids. Examples of target nucleic acid molecules also comprise RNA analytes such as various types of coding and non-coding RNA. Examples of the different types of RNA analytes comprise messenger RNA (mRNA), ribosomal RNA (rRNA), transfer RNA (tRNA), microRNA (miRNA), pre-mRNA, and viral RNA. RNA analytes can be obtained from or analyzed in cells or cellular compartments (e.g., nucleus).

In some embodiments, the method comprises analyzing a transcriptome or genome, e.g., the global transcriptome or genome, of one or more single cells deposited and/or immobilized on a substrate. In some embodiments, the method comprises a process for high-throughput profiling of a large number of analytes in situ, which enables the simultaneous analysis of an expression pattern and/or a location/distribution pattern of the genes or genomic loci expressed or present in one or more single cells deposited and/or immobilized on a substrate.

In some embodiments, the in situ assay is a targeted assay, e.g., one that analyzes pre-designed probes that directly or indirectly bind to biological analytes of interest, e.g., mRNA molecules in one or more single cells deposited and/or immobilized on a substrate. In some embodiments, the in situ assay comprises providing one or more nucleic acid probes that hybridize to a nucleic acid analyte (or a complement, amplification product, or derivative thereof) and detecting the one or more nucleic acid probes. In some embodiments, the pre-designed probes comprise one or more primary probes or probe sets, e.g., a probe that binds to an analyte of interest, and/or one or more secondary probes or probe sets, e.g., a probe that binds to a primary probe or complement thereof or product (e.g., a hybridization product, a ligation product, an extension product (e.g., by a DNA or RNA polymerase), a replication product, a transcription/reverse transcription product, and/or an amplification product) thereof. In some embodiments, the pre-designed probes comprise one or more higher order probes or probe sets, e.g., an $(n+1)^{th}$ order probe that binds to an $n^{th}$ order probe or complement thereof or product (e.g., a hybridization product, a ligation product, an extension product (e.g., by a DNA or RNA polymerase), a replication product, a transcription/reverse transcription product, and/or an amplification product) thereof, where n is an integer of 2 or greater. In some embodiments, the pre-designed probes are barcoded probes. In some embodiments, an $n^{th}$ order probe comprises a barcode sequence (an $n^{th}$ order barcode sequence), and an $(n+1)^{th}$ order probe binds to the $n^{th}$ order barcode sequence and comprises an $(n+1)^{th}$ order barcode sequence for binding by another barcoded probe or by a detectably labeled probe, e.g., a fluorescently labeled detection oligo, where n is an integer of 1 or greater. In any of the embodiments disclosed herein, the binding of a probe to another probe or to an analyte of interest may be direct (e.g., via direct hybridization of nucleic acid sequences or antigen-antibody binding) or indirect (e.g., indirect hybridization via one or more bridging oligo or binding interaction). The binding interactions may be analyzed using microscopy, such as high-resolution optical microscopy, to provide readouts of the presence/absence, distribution, location, amount, level, expression, or activity of the target analyte. In some embodiments, the in situ assay comprises in situ sequencing and/or in situ hybridization, such as sequential hybridization of probes. In some embodiments, the in situ assay analyzes about 20, about 50, about 100, about 200, about 500, about 1,000, about 2,000, about 5,000, about 10,000, or more genes, e.g., mRNA transcripts from the genes in one or more single cells deposited and/or immobilized on a substrate. In some embodiments, mRNA transcripts from between about 100 and about 1,000 genes are analyzed in situ in one or more single cells deposited and/or immobilized on a substrate.

In some aspects, the method comprises analyzing a transcriptome or genome, e.g., the global transcriptome or genome, of a tissue sample. Cells of the tissue sample can be dissociated, and dissociated single cells are deposited and/or immobilized on a substrate for in situ analysis. In some embodiments, the method comprises a process for performing transcriptomics and/or genomics, which enables the simultaneous analysis of an expression pattern and/or a location/distribution pattern of the genes or genomic loci expressed or present in single cells of a tissue sample. In some embodiments, the method further comprises synthesis of nucleic acid molecules which are sequenced, e.g., with single nucleotide resolution, and analyzed to determine which genes are expressed in one or more single cells deposited and/or immobilized on a substrate. In some embodiments, the individual, separate and specific transcriptome of each cell can be obtained at the same time, providing highly parallel comprehensive transcriptome signatures from individual cells within a large number of single cells derived from multiple samples (e.g., tissue samples) without performing cell partitioning.

In some embodiments, a method disclosed herein comprises sequentially performing one or more in situ assays. The in situ analysis of a first target may be performed either before, concurrently with, or after analyzing a second analyte. In some embodiments, a method disclosed herein comprises providing a readout, e.g., a microscopy readout. In some embodiments, a method disclosed herein comprises analyzing a microscopy readout for the in situ assay. In some embodiments, the first analyte and the second analyte are different molecules.

In some embodiments, a method disclosed herein comprises contacting dissociated cells deposited and/or immobilized on a substrate, e.g., a glass slide, with one or more nucleic acid probes that directly or indirectly bind to a first target nucleic acid or a complement or product (e.g., a hybridization product, a ligation product, an extension product (e.g., by a DNA or RNA polymerase), a replication product, a transcription/reverse transcription product, and/or an amplification product) thereof in the immobilized cell sample. In some embodiments, the method further comprises contacting dissociated cells on the substrate with nucleic acid probes that directly or indirectly bind to one or more second target nucleic acids in the immobilized cell sample.

In some embodiments, the dissociated cells on the substrate are subjected to an in situ analysis, e.g., in situ detection of the reporter oligonucleotides indicative of the sample origins of dissociated cells and in situ detection of one or more analytes (e.g., nucleic acid analytes and/or non-nucleic acid analytes) in the immobilized cell sample. In some embodiments, the first target nucleic acid is located within the labeling agent bound to the cell surface. In some embodiments, the first target nucleic acid is the reporter oligonucleotide of the labeling agent and comprises a sample-specific barcode sequence. In some embodiments, the one or more second target nucleic acids are located in and/or on the immobilized cells. In some embodiments, the one or more second target nucleic acids comprise a plurality of genomic DNA, cellular RNA (e.g., mRNA), and/or cDNA molecules. In some embodiments, the one or more second target nucleic acids comprise transcripts of a plurality of genes of interest. In some embodiments, the one or more second target nucleic acids comprise a plurality of nucleic acid tags directly or indirectly conjugated to binding moieties that bind to non-nucleic acid analytes in the dissociated cells from different samples. In some embodiments, the dissociated single cells are derived from multiple different biological samples wherein each sample is contacted with a labeling agent comprising a reporter that identifies the sample origin. Thus, using the compositions, systems, and methods described herein, cells from different samples (e.g., different cell populations, cell types, experimental conditions, etc.) can be "tagged" with different reporters (e.g., sample-specific barcode sequences) and subsequently combined for multiplex in situ analysis with tags serving to later identify specific sample sources when de-multiplexing. In some embodiments, the biological sample is a tissue sample, such as a freshly isolated or preserved tissue section. The tissue sample can be labeled with a labeling agent, and cells of the tissue sample are then dissociated to provide a population of single cells. Alternatively, the tissue sample can be dissociated to provide a population of single cells, and cells in the population are then labeled with a labeling agent.

In some embodiments, the dissociated single cells are pooled and immobilized onto a substrate. In some embodiments, the dissociated single cells are fixed by reversible cross-linking. In some embodiments, the dissociated single cells are processed such that one or more analyte molecules (e.g., RNA molecules) are reversibly or irreversibly locked in place to preserve a spatial pattern of the presence/absence, distribution, location, amount, level, expression, or activity of the analyte within a dissociated single cell and/or relatively to one or more other analytes in the dissociated single cell. In some embodiments, the dissociated single cells on the substrate are embedded in a matrix, such as a polymeric matrix. In some embodiments, the dissociated single cells on the substrate are hydrogel-embedded. In some embodiments, the one or more analyte molecules (e.g., RNA molecules) are targeted by probes and analyzed using in situ imaging, for example sequencing by ligation, sequencing by hybridization, sequencing by synthesis, sequencing by binding, and/or sequential hybridization of barcoded probes followed by decoding. In some embodiments, molecules of a plurality of analytes in the sample are analyzed in situ in a highly multiplexed approach.

In some embodiments, the in situ analysis comprises detecting the reporter oligonucleotides of the dissociated cells and one or more target nucleic acids in the dissociated cells. In some embodiments, one or more signals associated with the reporter oligonucleotides of the dissociated cells are detected before detecting one or more signals associated with the one or more target nucleic acids in the dissociated cells. In some embodiments, one or more signals associated with the reporter oligonucleotides of the dissociated cells are detected after detecting one or more signals associated with the one or more target nucleic acids in the dissociated cells. In some embodiments, one or more signals associated with the reporter oligonucleotides of the dissociated cells are detected concurrently with detecting one or more signals associated with the one or more target nucleic acids in the dissociated cells.

For example, the dissociated cells can be derived from four different samples, each of which is identified by a reporter oligonucleotide comprising a sample-specific barcode sequence. In this example, a particular dissociated cell on the substrate is labeled with one of the four different reporter oligonucleotides. The dissociated cells can be contacted with a plurality of detectable probes each configured to directly or indirectly bind to one of four different reporter oligonucleotides, and signals associated with the plurality of detectable probes at the locations of the dissociated cells on the substrate can be detected to identify the sample origins of the dissociated cells. For instance, each of the four different reporter oligonucleotides can be detected by a fluorescently labeled probe of a different color. In cases where the number of different samples is large, a combinatorial approach can be used to increase capacity of sample multiplexing. As an example, the reporter oligonucleotides and the corresponding detectable probes can be designed such that each reporter oligonucleotide comprises two regions each detectable by a detectable probe. With four different colors, at least sixteen different samples can be identified by reporter oligonucleotides of different combinations of the four colors.

In some instances, in situ assays take a targeted approach interrogating a panel of target analytes, e.g., between about 50 to about 1,000 genes and mRNA transcripts therefrom, using target-binding probes and a microscopy-based readout and analysis of optical signals for target analysis and/or sequence determination. In some embodiments, the in situ assay comprises in situ detection of one or more barcode sequences of a probe that directly or indirectly binds an analyte. In some embodiments, the in situ assay comprises detecting signals indicative of hybridization of one or more detectably labeled oligonucleotides to one or more barcode sequences of a probe (or amplification product thereof) that directly or indirectly hybridizes to a nucleic acid moiety of an analyte, and a spatial and/or temporal pattern of the signals from the sequential hybridization is used to analyze the analyte. In some embodiments, in situ probes (e.g., circular or circularizable probes for RCA and/or primary probes for in situ hybridization involving sequential hybridization of detectable probes) bind to target analytes (e.g., nucleic acid molecules) in a sample for in situ analysis. The in situ probes may comprise two or more probes that are assembled to form a larger probe upon binding to a target molecule and connecting the two or more probes (e.g., via ligation such as DNA-templated ligation and/or RNA-template dependent ligation of DNA probes comprising ribonucleotides). The in situ probes or products thereof can be amplified, e.g., using rolling circle amplification, to generate an amplification product which can be detected in situ, e.g., as shown in FIG. 1.

The present disclosure in another aspect provides a method for sample analysis, comprising (a) contacting a first sample and a second sample with a first labeling agent and a second labeling agent, respectively, to provide labeled cells in each sample, wherein the first labeling agent and the second labeling agent each comprises (i) a binding moiety and (ii) a reporter oligonucleotide comprising a first barcode region comprising a sample-specific barcode sequence corresponding to the respective sample, wherein the binding moiety of each labeling agent binds to one or more cells in the respective sample; (b) combining the first and second samples; (c) dissociating the first and second samples into dissociated cells; (d) immobilizing a population of cells comprising labeled cells from the first and second samples on a substrate; (e) contacting the immobilized cells with: (i) a first probe that hybridizes to the sample-specific barcode sequence corresponding to the first or second sample, and (ii) a second probe that binds to an analyte in and/or on one or more of the immobilized cells, wherein the second probe comprises a second barcode region; and (f) detecting a first signal associated with the first probe or a product thereof and a second signal associated with the second probe or a product thereof on the substrate, thereby detecting the presence or absence of the analyte in one or more cells from the first sample and/or from the second sample. In some embodiments, the first and second samples are combined in (b) prior to the dissociation into dissociated cells in (c). In some embodiments, the first and second samples are dissociated into dissociated cells in (c) prior to the combined in (b).

Additional details of the disclosure are provided below by way of example.

II. Samples, Analytes, and Target Sequences

A. Samples

A sample disclosed herein can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can include nucleic acids (such as DNA or RNA), proteins/polypeptides, carbohydrates, and/or lipids. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate as described elsewhere herein.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i). Disaggregation of Cells

In some embodiments, the biological sample corresponds to cells (e.g., derived from a cell culture, a tissue sample, or cells deposited on a surface). In a cell sample with a plurality of cells, individual cells can be naturally unaggregated. For example, the cells can be derived from a suspension of cells (e.g., a body fluid such as blood) and/or disassociated or disaggregated cells from a tissue or tissue section. The number of cells in the biological sample can vary. Some biological samples comprise large numbers of cells, e.g., blood samples, while other biological samples comprise smaller or only a small number of cells or may only be suspected of containing cells, e.g., plasma, serum, urine, saliva, synovial fluids, amniotic fluid, lachrymal fluid, lymphatic fluid, liquor, cerebrospinal fluid and the like.

In some embodiments, a cell-containing biological sample can comprise a body fluid or a cell-containing sample derived from the body fluid, e.g., whole blood, samples derived from blood such as plasma or serum, buffy coat, urine, sputum, lachrymal fluid, lymphatic fluid, sweat, liquor, cerebrospinal fluid, ascites, milk, stool, bronchial lavage, saliva, amniotic fluid, nasal secretions, vaginal secretions, semen/seminal fluid, wound secretions, cell culture and swab samples, or any cell-containing sample derived from the aforementioned samples. In some embodiments, a cell-containing biological sample can be a body fluid, a body secretion or body excretion, e.g., lymphatic fluid, blood, buffy coat, plasma or serum. In some embodiments, a cell-containing biological sample can be a circulating body fluid such as blood or lymphatic fluid, e.g., peripheral blood obtained from a mammal such as human In some embodiments, the cells in a biological sample may be aggregated, and may be disaggregated into individual cells using, for example, enzymatic or mechanical techniques. Examples of enzymes used in enzymatic disaggregation include, but are not limited to, dispase, collagenase, trypsin, and combinations thereof. Mechanical disaggregation can be performed, for example, using a tissue homogenizer. The biological sample may comprise disaggregated cells (e.g., nonadherent or suspended cells) which are deposited on a surface and subjected to an in situ assay disclosed herein.

In addition to separating a biological sample into single cells, described herein are methods of separating a biological sample into cell groups, types of cells, or a region or regions of interest. For example, a biological sample can be dissociated and/or separated into single cells, cell groups, types of cells, or a region or regions of interest before being contacted with the labeling agents (e.g., binding moiety attached to a reporter oligonucleotide). In other examples, a biological sample is first contacted with one or more labeling agents, and then separated into single cells, cell groups, types of cells, or a region or regions of interest.

In some embodiments, a biological sample can be separated into chucks using pixelation. Pixelation can include the steps of providing a biological sample, and punching out one or more portions of the biological sample.

Non-limiting, non-exhaustive steps for "pixelating" a sample, include cutting, stamping, microdissecting, or transferring by hollow-needle or microneedle, and/or moving a small portion of the sample into an individual partition or well. In an example, an array of needles are punched through a sample on a scaffold and into nanowells containing reagents.

In any of the embodiments herein, a population of cells can comprise cells derived from multiple different samples. In any of the embodiments herein, the population can comprise at least about 100, at least about 1,000, at least about 10,000, at least about 50,000, at least about 100,000, or at least about 500,000 dissociated cells.

In some aspects, a method disclosed herein provides an alternative to partition-based analysis, and the method can be used to analyze multiple samples (e.g., multiple different cell suspensions) in bulk without the need to partition individual cells into separate partitions or reaction chambers. While certain single-cell assays such as single-cell RNA sequencing techniques may require generating singlets and removing multiplets, the method disclosed herein uses an in situ platform for multiplex detection and can tolerate multiplets (e.g., doublets), as long as when deposited on a substrate, the cells or nuclei in the multiplets can be segmented and an analyte in an individual cell or nucleus can be detected without interference by an adjacent cell or nucleus in the multiplets.

In some embodiments, a sample such as a tissue sample can be dissociated to generate singlets which are contacted with a sample-specific labeling agent. In some embodiments, the sample can be contacted with the sample-specific labeling agent and dissociated to generate singlets, where the singlets remain labeled by the sample-specific labeling agent. Singlets can include single cells or nuclei captured after multiplet removal. Dissociated single cells or nuclei from multiple biological samples can be labeled with sample-specific labeling agents such that the sample origin of a particular single cell or nucleus can be identified based on its sample-specific labeling agent(s). In some embodiments, at least or about 100, at least or about 200, at least or about 500, at least or about 1,000, at least or about 2,000, at least or about 5,000, at least or about 10,000, at least or about 20,000, at least or about 50,000, at least or about 100,000, at least or about 200,000, at least or about 500,000, at least or about 1,000,000, at least or about 2,000,000, or at least or about 5,000,000 singlets from a first sample are labeled with the same first sample-specific labeling agent or combination of sample-specific labeling agents, whereas at least or about 100, at least or about 200, at least or about 500, at least or about 1,000, at least or about 2,000, at least or about 5,000, at least or about 10,000, at least or about 20,000, at least or about 50,000, at least or about 100,000, at least or about 200,000, at least or about 500,000, at least or about 1,000, 000, at least or about 2,000,000, or at least or about 5,000,000 singlets from a second sample are labeled with the same second sample-specific labeling agent or combination of sample-specific labeling agents, where the first and second sample-specific labeling agents (or combinations of sample-specific labeling agents) are different such that when the samples are combined for multiplex detection on an in situ platform, the sample origin of a particular singlet can be identified. In some embodiments, at least or about 50%, at least or about 60%, at least or about 70%, at least or about 80%, at least or about 90%, at least or about 95%, or at least or about 99% of cells or nuclei in a sample (e.g., a suspension of cells and/or nuclei) labeled with the same sample-specific barcode sequence can be singlets, and the rest can be multiplets (e.g., doublets) which may or may not be removed prior to depositing the labeled cells and/or nuclei for analysis on an in situ platform. In some embodiments, the sample-specific barcode sequence for a sample is shared by at least or about 100, at least or about 200, at least or about 500, at least or about 1,000, at least or about 2,000, at least or about 5,000, at least or about 10,000, at least or about 20,000, at least or about 50,000, at least or about 100,000, at least or about 200,000, at least or about 500,000, at least or about 1,000,000, at least or about 2,000,000, or at least or about 5,000,000 cells and/or nuclei from the sample and is not specific to any particular endogenous polynucleotide or exogenous polynucleotide introduced into one or more cells or nuclei of the sample.

(ii). Substrate Attachment

In some embodiments, the biological sample can be attached to a substrate. Examples of substrates suitable for this purpose are described in detail below. Attachment of the biological sample can be irreversible or reversible, depending upon the nature of the sample and subsequent steps in the analytical method.

In certain embodiments, the sample can be attached to the substrate reversibly by applying a suitable polymer coating to the substrate, and contacting the sample to the polymer coating. The sample can then be detached from the substrate using an organic solvent that at least partially dissolves the polymer coating. Hydrogels are examples of polymers that are suitable for this purpose.

More generally, in some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

(iii) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DiR, DiD). Other cell membrane stains may include FM and RH dyes or immunohistochemical reagents specific for cell membrane proteins. In some examples, the stain may include but is not limited to, acridine orange, acid fuchsin, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine, or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Any suitable methods of destaining or discoloring a biological sample may be utilized and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(iv) Isometric Expansion

In some embodiments, a biological sample embedded in a matrix (e.g., a hydrogel) can be isometrically expanded. Isometric expansion methods that can be used include hydration, a preparative step in expansion microscopy, as described in, e.g., Chen et al., *Science* 347(6221):543-548, 2015 and U.S. Pat. No. 10,059,990. Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel).

(v) Crosslinking and De-Crosslinking

In some embodiments, the biological sample is reversibly cross-linked prior to or during an in situ assay. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, the biological sample is immobilized in a hydrogel via cross-linking of the polymer material that forms the hydrogel.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof. Examples of suitable hydrogels are described, for example, in U.S. Pat. Nos. 6,391,937, 9,512, 422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. In some embodiments, hydrogel formation within a biological sample is reversible.

In some embodiments, HTC and/or additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, ligase, proteinase K, and DNAse. Additional reagents can also include reverse transcriptase enzymes, including enzymes with terminal transferase activity, primers, and switch oligonucleotides. In some embodiments, a cell labeling agent, including optical labels are added to the hydrogel subunits before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(vi) Cell Permeabilization and Treatment

In some embodiments, a biological sample (e.g., dissociated cells on a substrate) can be permeabilized to facilitate transfer of species (such as labeling agents and/or detectable probes) into the sample. In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods, e.g., physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to open up DNA in a cell for hybridization by a probe. For example, proteinase K treatment may be used to free up DNA with proteins bound thereto.

B. Labeling Agents

In some embodiments, provided herein are methods and compositions for cell analysis using one or more labeling agents. In some embodiments, a labeling agent is capable of binding to or otherwise coupling to one or more cells or cell features (e.g., a molecule on and/in a cell). For example, a labeling agent may comprise a lipophilic moiety (e.g., cholesterol) that can interact with all cells in one or more samples in a non-analyte specific way. In some embodiments, the labeling agent does not bind an analyte. In some embodiments, the labeling agent comprises a binding moiety and/or a reporter oligonucleotide. In some embodiments, the binding moiety of the labeling agent does not bind to the analyte. In some embodiments, the reporter oligonucleotide comprises one or more barcodes (e.g., target-specific barcodes and/or sample-specific barcodes) Exemplary labeling agents for binding to or coupling to one or more cells or cell features is described in Section III-A.

In some embodiments, provided herein are methods and compositions for analyzing endogenous analytes (e.g., RNA, ssDNA, cell surface or intracellular proteins, and/or metabolites) in a sample using one or more labeling agents. In some embodiments, a labeling agent may include an agent that interacts with an analyte (e.g., an endogenous analyte in a sample).

In some embodiments, the labeling agent comprises a probe that targets an analyte. For instance, the labeling agent comprises a probe that binds to a house-keeping gene transcript that is present in substantially all cells in a sample. In some embodiments, the labeling agent may comprise a sample-specific barcode. In some embodiments, the labeling agent can comprise a sample-specific barcode and/or a target-specific barcode.

In some embodiments, the labeling agent comprises a probe that binds to an analyte. In some embodiments, the probe can directly or indirectly bind to a nucleic acid analyte (e.g., mRNA). In some embodiments, the probe can comprise one or more barcode sequences (e.g., target-specific barcode sequences and/or sample-specific barcode sequence). The probe may comprise a sample-specific barcode sequence that corresponds to the samples from which the biological cell is derived. The probe may comprise a target-specific barcode which comprises a barcode that is associated with or otherwise identifies the nucleic acid analyte to which the probe is bound. In some embodiments, the analyte bound to the labeling agent is detected in situ.

In some embodiments, the labeling agent comprises an agent that binds to a non-nucleic acid analyte (e.g., intracellular proteins). In some embodiments, the non-nucleic acid analyte bound to the labeling agent is detected in situ. In some embodiments, the labeling agents can comprise a binding moiety and a reporter oligonucleotide. The reporter oligonucleotide is indicative of the target analyte or portion thereof interacting with the binding moiety. For example, the reporter oligonucleotide may comprise a barcode sequence that permits identification of the binding moiety. In some cases, the sample contacted by the labeling agent can be further contacted with a probe (e.g., a single-stranded probe sequence), that hybridizes to a reporter oligonucleotide of the labeling agent, in order to identify the analyte associated with the labeling agent. In some embodiments, the labeling agent comprises a binding moiety and a reporter oligonucleotide comprising one or more barcode sequences, e.g., a barcode sequence that corresponds to the binding moiety and/or the target analyte. A binding moiety barcode or a target-specific barcode includes a barcode that is associated with or otherwise identifies the binding moiety. In some embodiments, by identifying a binding moiety by identifying its associated target-specific barcode, the target analyte to which the binding moiety binds can also be identified. In some embodiments, the labeling agent comprises one or more barcode sequences, e.g., a sample-specific barcode sequence that corresponds to the samples from which the biological cell is derived. The sample-specific or target-specific barcode can be a nucleic acid sequence of a given length and/or sequence that is associated with the binding moiety. A sample-specific or target-specific barcode can generally include any of the variety of aspects of barcodes described herein. In some embodiments, the method comprises one or more post-fixing (also referred to as post-fixation) steps after contacting the sample with one or more labeling agents.

In the methods and systems described herein, one or more labeling agents capable of binding to or otherwise coupling to one or more features may be used to characterize analytes, cells and/or cell features, including cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, a binding moiety may include any molecule or moiety capable of binding to an analyte (e.g., a biological analyte, e.g., a macromolecular constituent) which may be in and/or on a cell. A binding moiety may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The analyte binding moiety can be attached to a reporter oligonucleotide that is indicative of the sample from which a cell is derived. For instance, the same analyte binding moiety (e.g., an antibody or a lipid moiety configured to bind to the same cell surface feature) can be used to bind to cells from different samples, wherein the same analyte binding moiety is attached to different reporter oligonucleotides each identifying one of the different samples. For example, the reporter oligonucleotide may comprise a barcode sequence that permits identification of the sample from which a cell labeled with the reporter oligonucleotide is derived. For example, a first sample can be contacted with a binding moiety that is coupled thereto a first reporter oligonucleotide identifying the first sample, while a second sample can be contacted with the same binding moiety which is coupled to a different reporter oligonucleotide identifying the second sample.

Optionally, the reporter oligonucleotide can be indicative of a cell surface feature to which the binding moiety binds. For example, a binding moiety that is specific to one type of cell feature (e.g., a first cell surface feature) may have coupled thereto a first reporter oligonucleotide, while a binding moiety that is specific to a different cell feature (e.g., a second cell surface feature) may have a different reporter oligonucleotide coupled thereto. For a description of exemplary binding moieties, including antibody-based labeling agents, reporter oligonucleotides, and methods of use, see, e.g., U.S. Pat. No. 10,550,429; PCT Pub. No. WO2019113533A1; U.S. Pat. Pub. 20190177800; and U.S. Pat. Pub. 20190367969, which are each incorporated by reference herein in their entirety.

In some embodiments, a binding moiety includes one or more antibodies or epitope binding fragments thereof. The antibodies or epitope binding fragments including the binding moiety can specifically bind to a target analyte. In some embodiments, the analyte is a protein (e.g., a protein on a surface of the biological sample (e.g., a cell) or an intracellular protein). In some embodiments, a plurality of labeling agents comprising a plurality of binding moieties bind a plurality of analytes present in a biological sample. In some embodiments, the plurality of analytes includes a single species of analyte (e.g., a single species of polypeptide). In some embodiments in which the plurality of analytes includes a single species of analyte, the binding moieties of the plurality of labeling agents are the same. In some embodiments in which the plurality of analytes includes a single species of analyte, the binding moieties of the plurality of labeling agents are the different (e.g., members of the plurality of analyte labeling agents can have two or more species of binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labeling agent that is specific to a particular cell feature (e.g., a molecule on and/in a cell) may have a first plurality of the binding moiety (e.g., an antibody or lipophilic moiety) coupled to a first reporter oligonucleotide and a second plurality of the binding moiety coupled to a second reporter oligonucleotide.

In some aspects, these reporter oligonucleotides may comprise nucleic acid barcode sequences that permit identification of the sample origins of cells labeled with the reporter oligonucleotides. The selection of oligonucleotides as the reporter may provide advantages of being able to generate significant diversity in terms of sequence, while also being readily attachable to most biomolecules, e.g., antibodies, etc., as well as being readily detected, e.g., using the in situ detection techniques described herein.

Attachment (coupling) of the reporter oligonucleotides to the binding moiety may be achieved through any of a variety of direct or indirect, covalent or non-covalent associations or attachments. For example, oligonucleotides may be covalently attached to a portion of a labeling agent (such a protein, e.g., an antibody or antibody fragment) using chemical conjugation techniques (e.g., Lightning-Link® antibody labeling kits available from Innova Biosciences), as well as other non-covalent attachment mechanisms, e.g., using biotinylated antibodies and oligonucleotides (or agents that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labeling and Affinity Purification of Synthetic Oligonucleotides," Nucleic Acids Res. Jan. 15, 2003; 31(2):708-715, all of which are herein incorporated by reference in their entireties s. Likewise, protein and peptide biotinylation techniques have been developed and are readily available. See, e.g., U.S. Pat. No. 6,265,552, the content of which is herein incorporated by reference in its entirety. Furthermore, click reaction chemistry may be used to couple reporter oligonucleotides to labeling agents. Commercially available kits, such as those from Thunderlink and Abcam, and techniques common in the art may be used to couple reporter oligonucleotides to labeling agents as appropriate. In another example, a labeling agent is indirectly (e.g., via hybridization) coupled to a reporter oligonucleotide comprising a barcode sequence that identifies the labeling agent. For instance, the labeling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labeling agent to the reporter oligonucleotide. In some instances, in addition to the sample-specific barcode sequence, a reporter oligonucleotide described herein may comprise one or more other sequences, such as an additional barcode sequence, an adapter sequence, a unique molecular identifier (UMI) sequence, and/or a primer or primer binding sequence C. Analytes A biological sample may comprise one or a plurality of analytes of interest. Methods for performing multiplexed assays to analyze two or more different analytes in a single biological sample are provided.

The methods and compositions disclosed herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of an RCA (rolling circle amplification) template (e.g. a padlock or other circularizable probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, including combinations of the aforementioned types of molecules.

(i) Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labeling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and epitope binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a cell or a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a cell or a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), among others.

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be derived from or detected in a live cell. Processing conditions can be adjusted to ensure that a biological sample remains live during analysis. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In some embodiments described herein, the analyte comprises a target sequence. In some embodiments, the target sequence may be endogenous to the sample, generated in the sample, added to the sample, or associated with an analyte in the sample. In some embodiments, the target sequence is a single-stranded target sequence (e.g., a sequence in a rolling circle amplification product). In some embodiments, the analytes comprise one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

In Situ(ii) Products of Endogenous Analyte and/or Labeling Agent

In some embodiments, provided herein are methods and compositions for analyzing one or more products of an endogenous analyte and/or a labeling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product such as a rolling circle amplification (RCA) product) thereof is analyzed. In some embodiments, a labeling agent that directly or indirectly binds to an analyte in the biological sample is analyzed. In some embodiments, a product (e.g., a hybridization product, a ligation product, an extension product (e.g., by a DNA or RNA polymerase), a replication product, a transcription/reverse transcription product, and/or an amplification product such as a rolling circle amplification (RCA) product) of a labeling agent that directly or indirectly binds to an analyte in the biological sample is analyzed.

(a) Hybridization

In some embodiments, a product of an endogenous analyte and/or a labeling agent is a hybridization product comprising the pairing of substantially complementary or complementary nucleic acid sequences within two different molecules, one of which is the endogenous analyte or the labeling agent (e.g., reporter oligonucleotide attached thereto). The other molecule can be another endogenous molecule or another labeling agent such as a probe. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

Various probes and probe sets can be hybridized to an endogenous analyte and/or a labeling agent and each probe may comprise one or more barcode sequences. Exemplary barcoded probes or probe sets may be based on a circularizable probe or probe set (e.g., padlock probe), a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set, DNA probes bound to RNA targets, or RNA-templated ligation probes. The specific probe or probe set design can vary.

(b) Ligation

In some embodiments, a product of an endogenous analyte and/or a labeling agent is a ligation product. In some embodiments, the ligation product is formed between two or more endogenous analytes. In some embodiments, the ligation product is formed between two or more labeling agent. In some embodiments, the ligation product is an intramolecular ligation of an endogenous analyte. In some embodiments, the ligation product is an intramolecular ligation product or an intermolecular ligation product, for example, the ligation product can be generated by the circularization of a circularizable probe or probe set upon hybridization to a target sequence. The target sequence can be comprised in an endogenous analyte (e.g., nucleic acid such as a genomic DNA or mRNA) or a product thereof (e.g., cDNA from a cellular mRNA transcript), or in a labeling agent (e.g., the reporter oligonucleotide) or a product thereof.

In some embodiments, provided herein is a probe or probe set capable of DNA-templated ligation, such as from a cDNA molecule. See, e.g., U.S. Pat. No. 8,551,710, the content of which is herein incorporated by reference in its entirety. In some embodiments, provided herein is a circularizable DNA probe or probe set capable of hybridizing to target nucleic acids (e.g., mRNA molecule) and being ligating in a target-dependent manner (e.g., RNA-templated ligation). See, e.g., U.S. Pat. Pub. 2020/0224244, the content of which is herein incorporated by reference in its entirety. In some embodiments, the probe set is a SNAIL probe set. See, e.g., U.S. Pat. Pub. 20190055594, the content of which is herein incorporated by reference in its entirety. In some embodiments, provided herein is a multiplexed proximity ligation assay. See, e.g., U.S. Pat. Pub. 20140194311, the content of which is herein incorporated by reference in its entirety. In some embodiments, provided herein is a probe or probe set capable of proximity ligation, for instance a proximity ligation assay for RNA (e.g., PLAYR) probe set. See, e.g., U.S. Pat. Pub. 20160108458, which is hereby incorporated by reference in its entirety. In some embodiments, a circular probe can be indirectly hybridized to the target nucleic acid. In some embodiments, the circular construct is formed from a probe set capable of proximity ligation, for instance a proximity ligation in situ hybridization (PLISH) probe set. See, e.g., U.S. Pat. Pub. 2020/0224243, the content of which is herein incorporated by reference in its entirety.

In some embodiments, the ligation involves chemical ligation (e.g., click chemistry ligation). Exemplary click chemistry reactions are described in Section III-C-vi. In some embodiments, the chemical ligation involves template dependent ligation. In some embodiments, the chemical ligation involves template independent ligation. In some embodiments, the click reaction is a template-independent reaction (see, e.g., Xiong and Seela (2011), J. Org. Chem. 76(14): 5584-5597, the content of which is herein incorporated by reference in its entirety). In some embodiments, the click reaction is a template-dependent reaction or template-directed reaction. In some embodiments, the template-dependent reaction is sensitive to base pair mismatches such that reaction rate is significantly higher for matched versus unmatched templates. In some embodiments, the click reaction is a nucleophilic addition template-dependent reaction. In some embodiments, the click reaction is a cyclopropane-tetrazine template-dependent reaction.

In some embodiments, the ligation involves enzymatic ligation. In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, e.g., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, circularizable probe or probe set (e.g., padlock probe), or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule.

(c) Primer Extension and Amplification

In some embodiments, a product is a primer extension product of an analyte, a labeling agent, a probe or probe set bound to the analyte (e.g., a circularizable probe or probe set (e.g., padlock probe)bound to genomic DNA, mRNA, or cDNA), or a probe or probe set bound to the labeling agent (e.g., a circularizable probe or probe set (e.g., padlock probe)bound to one or more reporter oligonucleotides from the same or different labeling agents).

A primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern), other natural or synthetic nucleotides described herein that can have additional functionality. A primer extension reaction can occur when two nucleic acid sequences become hybridized by an overlap of their respective terminal complementary nucleic acid sequences (e.g., 3' termini) Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some embodiments, a product of an endogenous analyte and/or a labeling agent is an amplification product of one or more polynucleotides, for instance, a circular probe or circularizable probe or probe set. In some embodiments, the amplifying is achieved by performing rolling circle amplification (RCA). In other embodiments, a primer that hybridizes to the circular probe or circularized probe is added and used as such for amplification. In some embodiments, the RCA comprises a linear RCA, a branched RCA, a dendritic RCA, or any combination thereof.

In some embodiments, the RCA template may comprise the target analyte, or a part thereof, where the target analyte is a nucleic acid, or it may be provided or generated as a proxy, or a marker, for the analyte. In some embodiments, different analytes are detected in situ in one or more cells using a RCA-based detection system, e.g., where the signal is provided by generating an RCA product from a circular RCA template which is provided or generated in the assay, and the RCA product is detected to detect the corresponding analyte. The RCA product may thus be regarded as a reporter which is detected to detect the target analyte. However, the RCA template may also be regarded as a reporter for the target analyte; the RCA product is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (e.g., a reagent in a detection assay), which is used as a reporter for the assay, or a part of a reporter, or signal-generation system. The RCA template used to generate the RCP may thus be a circular (e.g. circularized) reporter nucleic acid molecule, namely from any RCA-based detection assay which uses or generates a circular nucleic acid molecule as a reporter for the assay. Since the RCA template generates the RCP reporter, it may be viewed as part of the reporter system for the assay.

In some embodiments, a product herein includes a molecule or a complex generated in a series of reactions, e.g., hybridization, ligation, extension, replication, transcription/reverse transcription, and/or amplification (e.g., rolling circle amplification), in any suitable combination. For example, a product comprising a target sequence for a nucleic acid probe disclosed herein may be a hybridization complex formed of a cellular nucleic acid in a sample and an exogenously added nucleic acid probe. The exogenously added nucleic acid probe may comprise an overhang that does not hybridize to the cellular nucleic acid but hybridizes to another probe (e.g., a nucleic acid probe described herein). The exogenously added nucleic acid probe may be optionally ligated to a cellular nucleic acid molecule or another exogenous nucleic acid molecule. In other examples, a product comprising a target sequence for a nucleic acid probe disclosed herein may be an RCP of a circularizable probe or probe set which hybridizes to a cellular nucleic acid molecule (e.g., genomic DNA or mRNA) or product thereof (e.g., a transcript such as cDNA, a DNA-templated ligation product of two probes, or ligation product of two DNA probes generated in an RNA-template dependent manner (e.g., RNA-templated ligation). In some embodiments, a detectable probe may comprise an overhang that does not hybridize to an RCA product but hybridizes to another probe (e.g., a fluorescently labeled probe).

C. Target Sequences

A target sequence for a probe disclosed herein may be comprised in any analyte disclose herein, including an endogenous analyte (e.g., a viral or cellular nucleic acid), a labeling agent, or a product of an endogenous analyte and/or a labeling agent.

In some aspects, one or more of the target sequences includes one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide. In any of the preceding embodiments, the methods provided herein can include analyzing the barcodes by sequential hybridization and detection with a plurality of labeled probes (e.g., detection oligos).

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises 4N complexity given a sequencing read of N bases, and a much shorter sequencing read may be required for molecular identification compared to non-barcode sequencing methods such as direct sequencing. For example, 1024 molecular species may be identified using a 5-nucleotide barcode sequence (45=1024), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and US20210164039A1, all of which are herein incorporated by reference in their entireties.

III. General Cell-Based Analytical Methodology

A. Labeling Agents for Multiple Samples and Multiplexing Methods

The present disclosure provides methods and systems for multiplexing, and otherwise increasing throughput of samples for analysis. For example, a single or integrated process workflow may permit the processing, identification, and/or analysis of more or multiple analytes, more or multiple types of analytes, and/or more or multiple types of analyte characterizations. For example, in the methods and systems described herein, one or more labeling agents capable of binding to or otherwise coupling to one or more cells or cell features (e.g., a molecule on and/in a cell) may be used to characterize cells (including the cell features and/or analytes in and/or on the cells other than the cell features. In some instances, cell features include cell surface features. Exemplary cell surface features are described in Section II-B. In some embodiments, cell features may include intracellular analytes, such as proteins, protein modifications (e.g., phosphorylation status or other post-translational modifications), nuclear proteins, nuclear membrane proteins, or any combination thereof. A labeling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof.

In a particular example, a library of potential cell feature labeling agents may be provided, where the respective cell feature labeling agents are associated with nucleic acid reporter molecules, such that a different reporter oligonucleotide sequence is associated with each labeling agent capable of binding to a specific cell feature. In other aspects, different members of the library may be characterized by the presence of a different oligonucleotide sequence label. For example, an antibody capable of binding to a first protein may have associated with it a first reporter oligonucleotide sequence, while an antibody capable of binding to a second protein may have a different reporter oligonucleotide sequence associated with it. The presence of the particular oligonucleotide sequence may be indicative of the presence of a particular antibody or cell feature which may be recognized or bound by the particular antibody.

Labeling agents capable of binding to or otherwise coupling to one or more cells may be used to characterize a cell as belonging to a particular set of cells. For example, labeling agents may be used to label a sample of cells or a group of cells. In this way, a group of cells may be labeled as different from another group of cells. In an example, a first group of cells may originate from a first sample and a second group of cells may originate from a second sample. Labeling agents may allow the first group and second group to have a different labeling agent (or reporter oligonucleotide associated with the labeling agent). This may, for example, facilitate multiplexing, where cells of the first group and cells of the second group may be labeled separately and then pooled together for downstream analysis. The downstream detection of a label may indicate analytes as belonging to a particular group when de-multiplexing to associate analytes with the different sample sources.

For example, a reporter oligonucleotide may be linked to an antibody or an epitope binding fragment thereof, and labeling a cell may comprise subjecting the antibody-linked barcode molecule or the epitope binding fragment-linked barcode molecule to conditions suitable for binding the antibody to a molecule present on a surface of the cell. The binding affinity between the antibody or the epitope binding fragment thereof and the molecule present on the surface may be within a desired range to ensure that the antibody or the epitope binding fragment thereof remains bound to the molecule. For example, the binding affinity may be within a desired range to ensure that the antibody or the epitope binding fragment thereof remains bound to the molecule during various sample processing steps, such as nucleic acid amplification and/or extension. A dissociation constant ($K_d$) between the antibody or an epitope binding fragment thereof and the molecule to which it binds may be less than about 100 μM, 90 μM, 80 μM, 70 μM, 60 μM, 50 μM, 40 μM, 30 μM, 20 μM, 10 μM, 9 μM, 8 μM, 7 μM, 6 μM, 5 μM, 4 μM, 3 μM, 2 μM, 1 μM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 900 pM, 800 pM, 700 pM, 600 pM, 500 pM, 400 pM, 300 pM, 200 pM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM, or 1 pM. For example, the dissociation constant may be less than about 10 μM.

In another example, a reporter oligonucleotide may be coupled to a cell-penetrating peptide (CPP), and labeling cells may comprise delivering the CPP coupled reporter oligonucleotide into an analyte carrier. Labeling analyte carriers may comprise delivering the CPP conjugated oligonucleotide into a cell by the cell-penetrating peptide. A CPP that can be used in the methods provided herein can comprise at least one non-functional cysteine residue, which may be either free or derivatized to form a disulfide link with an oligonucleotide that has been modified for such linkage. Non-limiting examples of CPPs that can be used in embodiments herein include penetratin, transportan, plsl, TAT (48-

60), pVEC, MTS, and MAP. Cell-penetrating peptides useful in the methods provided herein can have the capability of inducing cell penetration for at least about 30%, 40%, 50%, 60%, 70%, 80%, 90%, 95%, 96%, 97%, 98%, 99%, or 100% of cells of a cell population. The CPP may be an arginine-rich peptide transporter. The CPP may be Penetratin or the Tat peptide. In another example, a reporter oligonucleotide may be coupled to a fluorophore or dye, and labeling cells may comprise subjecting the fluorophore-linked barcode molecule to conditions suitable for binding the fluorophore to the surface of the cell. In some instances, fluorophores can interact strongly with lipid bilayers and labeling cells may comprise subjecting the fluorophore-linked barcode molecule to conditions such that the fluorophore binds to or is inserted into a membrane of the cell. In some cases, the fluorophore is a water-soluble, organic fluorophore. In some instances, the fluorophore is Alexa Fluor™ 532 maleimide, tetramethylrhodamine-5-maleimide (TMR maleimide), BODIPY-TMR maleimide, Sulfo-Cy3 maleimide, Alexa Fluor™ 546 carboxylic acid/succinimidyl ester, ATTO™ 565 maleimide, Cy3 carboxylic acid/succinimidyl ester, Cy3B carboxylic acid/succinimidyl ester, ATTO™ 565 biotin, Sulforhodamine B, Alexa Fluor™ 594 maleimide, Texas Red® maleimide, Alexa Fluor™ 633 maleimide, Abberior® STAR 635P azide, ATTO™ 647N maleimide, ATTO™ 647 SE, or Sulfo-Cy5 maleimide. See, e.g., Hughes L D, et al. PLOS One. 2014 Feb. 4; 9 (2): e87649, which is hereby incorporated by reference in its entirety for all purposes, for a description of organic fluorophores.

A reporter oligonucleotide may be part of a nucleic acid molecule comprising any number of functional sequences. In other instances, e.g., to facilitate sample multiplexing, a labeling agent that is specific to a particular cell feature may have a first plurality of the labeling agent (e.g., an antibody or lipophilic moiety) coupled to a first reporter oligonucleotide and a second plurality of the labeling agent coupled to a second reporter oligonucleotide. For example, the first plurality of the labeling agent and second plurality of the labeling agent may interact with different cells, cell populations or samples, allowing a particular report oligonucleotide to indicate a particular cell population (or cell or sample) and cell feature. In this way, different samples or groups can be independently processed and subsequently combined together for pooled analysis.

As described elsewhere herein, libraries of labeling agents may be associated with a particular cell feature as well as be used to identify analytes as originating from a particular cell population, or sample. Cell populations may be incubated with a plurality of libraries such that a cell or cells comprise multiple labeling agents. For example, a cell may comprise coupled thereto a lipophilic labeling agent and an antibody. The lipophilic labeling agent may indicate that the cell is a member of a particular cell sample, whereas the antibody may indicate that the cell comprises a particular analyte. In this manner, the reporter oligonucleotides and labeling agents may allow multi-analyte, multiplexed analyses to be performed.

In some instances, these reporter oligonucleotides may comprise nucleic acid barcode sequences that permit identification of the labeling agent which the reporter oligonucleotide is coupled to. The use of oligonucleotides as the reporter may provide advantages of being able to generate significant diversity in terms of sequence, while also being readily attachable to most biomolecules (e.g., antibodies) and detectable.

In some cases, the labeling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labeling agent (or reporter oligonucleotide) either directly or indirectly (e.g., the label can be conjugated to a molecule that can bind to the labeling agent or reporter oligonucleotide). In some cases, a label is conjugated to an oligonucleotide that is complementary to a sequence of the reporter oligonucleotide, and the oligonucleotide may be allowed to hybridize to the reporter oligonucleotide.

Figure 2:
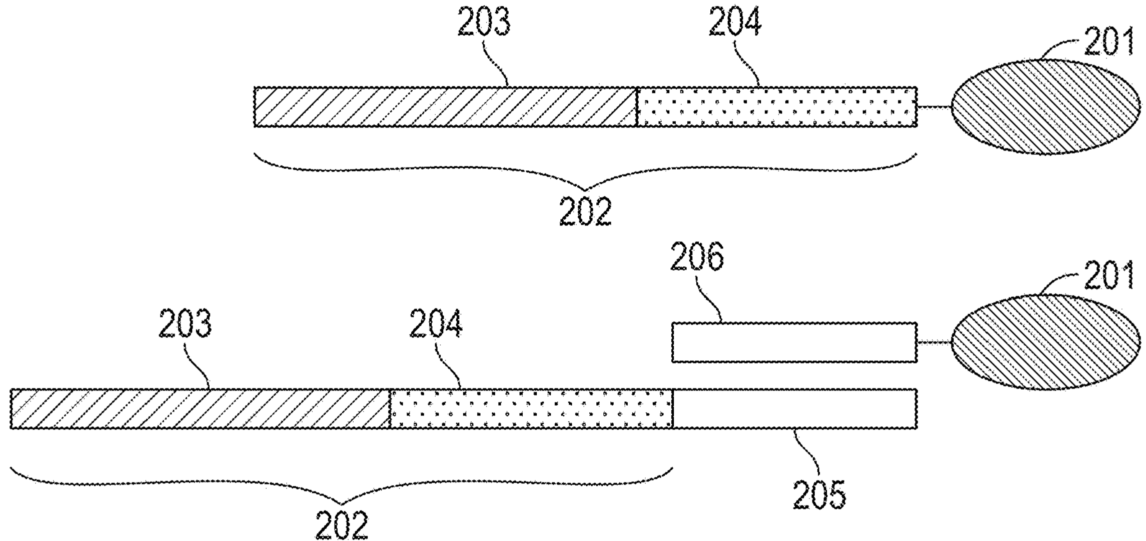
FIG. 2 schematically illustrates examples of labeling agents that comprise functional moieties 201 and reporter oligonucleotides 202.

FIG. 2 describes labeling agents comprising exemplary functional moieties 201 and reporter oligonucleotides 202 attached thereto. The functional moiety can react with and/or bind to one or more molecules on and/or in a cell. The functional moiety can be attached (either directly, e.g., covalently attached, or indirectly, e.g., via a linker) to the reporter oligonucleotide. Reporter oligonucleotide 202 may comprise a barcode region comprising one or more barcode sequences, including a sample-specific barcode sequence 203 that identifies the sample origin of a cell labeled with the labeling agent. Reporter oligonucleotide 202 may also comprise one or more other sequences 204, such as one or more other barcode sequences and/or functional sequences that can be used in subsequent processing, such as an adapter sequence, a unique molecular identifier (UMI) sequence, and/or a primer or primer binding sequence.

Referring to FIG. 2, upper panel, the functional moiety can be covalently attached to the reporter oligonucleotide. The one or more other sequences 204 can be between the sample-specific barcode sequence 203 and the functional moiety 201, as shown in the figure. However, the components can be attached to one another in any suitable configuration. For instance, the sample-specific barcode sequence can be between the one or more other sequences and the functional moiety, or between any two of the other sequences in the reporter oligonucleotide. Alternatively, the sample-specific barcode sequence and the one or more other sequences can be separately attached to the functional moiety.

Referring to FIG. 2, lower panel, the reporter oligonucleotide further comprises an adapter sequence 205 complementary to an adapter sequence 206 attached to the functional moiety 201. The reporter oligonucleotide is attached to the functional moiety via nucleic acid hybridization between adapter sequences 205 and 206. The components can be attached to one another in any suitable configuration. For instance, the sample-specific barcode sequence can be between the adapter sequence 205 and the one or more other sequences, or between any two of the other sequences in the reporter oligonucleotide.

A functional moiety can be any moiety on a first molecule that is capable of interacting with another functional moiety on the same molecule and/or on a second molecule. The interaction between the functional moieties can comprise physical interactions (e.g., direct or indirect binding) and/or chemical or enzymatic reactions, such as a reaction that forms a covalent or ionic linkage between the first and second molecules. In some instances, the functional moiety is a binding moiety. In some instances, the binding moiety is a protein or polypeptide (e.g., an antigen or prospective antigen) attached to the reporter oligonucleotide. In some instances, a sample-specific barcode sequence identifies the sample from which the labeled target (e.g., cell) is derived from. In some instances, the binding moiety is a lipophilic moiety (e.g., cholesterol) attached to the reporter oligonucleotide, where the lipophilic moiety is selected such that the binding moiety integrates into a membrane (e.g., the cell membrane) of a cell or nucleus. The reporter oligonucleotide may optionally comprise a target-specific barcode sequence that identifies the binding moiety which in some instances is used to tag cells (e.g., groups of cells, cell samples, etc.) and may be used for multiplex analyses as described elsewhere herein. In some instances, the sample-specific barcode sequence identifies the sample from which the labeled target (e.g., cell) is derived from. In some instances, the binding moiety is an antibody (or an epitope binding fragment thereof) attached to the reporter oligonucleotide.

One or more labeling agents that target a cell can be used to generate a cell comprising a plurality of labeling agents. In some instances, the plurality of the labeling agents are the same. In some instances, the plurality of the labeling agents are the different. For example, a cell may comprise, couples to the surface of the cell, a first labeling agent (e.g., comprising an antibody) and a second labeling agent (e.g., comprising a lipophilic molecule). Exemplary lipophilic molecules are disclosed in Section III-C-i. As another example, a cell may comprise, couples to the surface of the cell, a first type of labeling agent comprising a first lipophilic molecule and a second labeling agent comprising a second lipophilic molecule, wherein the first and second lipophilic molecules are different. In some instances, 1, 2, 3, 4, 5, 6, 7, 8, 9, 10, or more different labeling agents are utilized. In some instances, a plurality of labeling agents comprising different lipophilic molecules and/or antibodies can be used to label cells in a sample, and samples can be multiplexed using various combinations of lipophilic molecules and/or antibodies as the functional moieties in the labeling agents. Exemplary cell labeling methods and compositions that can be used in the present disclosures include those disclosed in WO 2021046475 A1, the content of which is herein incorporated by reference in its entirety.

Target-specific barcodes and binding moiety barcodes are barcodes that are associated with or otherwise identify the binding moiety and/or a target of the binding moiety. In some embodiments, by identifying a binding moiety by identifying its associated binding moiety barcode (e.g., target-specific barcode), the target to which the binding moiety binds can also be identified. A binding moiety barcode can be a nucleic acid sequence of a given length and/or sequence that is associated with the binding moiety. A binding moiety barcode can generally include any of the variety of aspects of barcodes described herein. For example, a labeling agent that is specific to one type of analyte can have coupled thereto a first barcode domain (e.g., that includes a first analyte binding moiety barcode), while a labeling agent that is specific to a different analyte can have a different barcode domain (e.g., that includes a second barcode analyte binding moiety barcode) coupled thereto. In some aspects, such barcode domain can include a binding moiety barcode (e.g., target-specific barcode), that permits identification of the binding moiety to which the labeling agent is coupled. The selection of the barcode domain can allow significant diversity in terms of sequence, while also being readily attachable to most binding moieties (e.g., antibodies) as well as being readily detected. In some embodiments, the labeling agents can include binding moieties with target-specific barcode domains attached to them. For example, a labeling agent can include a first binding moiety (e.g., an antibody that binds to a target, e.g., a first cell surface feature) having associated with it a target-specific barcode domain that includes a first binding moiety barcode.

Sample-specific barcodes are barcodes that are associated with or otherwise identify the sample from which the labeled cell is derived. In some embodiments, by identifying a sample-specific barcode, the sample from which the labeled cell is derived is identified. A sample-specific barcode can be a nucleic acid sequence of a given length and/or sequence that is associated with the sample. A sample-specific barcode can generally include any of the variety of aspects of barcodes described herein. For example, a labeling agent that is specific to one type of sample can have coupled thereto a first barcode domain (e.g., that includes a first sample-specific barcode), while a labeling agent that is specific to a different sample can have a different barcode domain (e.g., that includes a second sample-specific barcode) coupled thereto. In some aspects, such barcode domain can include a sample-specific barcode that permits identification of the sample from which the cell is derived. The selection of the barcode domain can allow significant diversity in terms of sequence, while also being readily attachable to most binding moieties (e.g., antibodies) as well as being readily detected.

In some embodiments, the target-specific barcode domain and/or a sample-specific barcode domain can be directly coupled to the binding moiety, or they can be attached to a bead, molecular lattice, e.g., a linear, globular, cross-slinked, or other polymer, or other framework that is attached or otherwise associated with the binding moiety, which allows attachment of multiple target-specific barcode domains and/or a sample-specific barcode domains to a single binding moiety. Attachment (coupling) of the target-specific barcode domains and/or a sample-specific barcode domains to the binding moieties can be achieved through any of a variety of direct or indirect, covalent or non-covalent associations or attachments. For example, in the case of a target-specific barcode domain and/or a sample-specific barcode domain coupled to a binding moiety that includes an antibody or epitope binding fragment, such target-specific barcode domains and/or a sample-specific barcode domains can be covalently attached to a portion of the antibody or epitope binding fragment using chemical conjugation techniques (e.g., Lightning-Link® antibody labeling kits available from Innova Biosciences).

In some embodiments, a target-specific barcode domain and/or a sample-specific barcode domain can be coupled to an antibody or epitope binding fragment using non-covalent attachment mechanisms (e.g., using biotinylated antibodies and oligonucleotides or reagents that include one or more biotinylated linker, coupled to oligonucleotides with an avidin or streptavidin linker.) Antibody and oligonucleotide biotinylation techniques can be used, and are described for example in Fang et al., Nucleic Acids Res. (2003), 31(2): 708-715, the entire contents of which are incorporated by reference herein. Likewise, protein and peptide biotinylation techniques have been developed and can be used, and are described for example in U.S. Pat. No. 6,265,552, the entire contents of which are incorporated by reference herein. Furthermore, click reaction chemistry such as a methyltetrazine-PEG5-NHS ester reaction, a TCO-PEG$_4$-NHS ester reaction, or the like, can be used to couple target-specific barcode domains and/or a sample-specific barcode domains to binding moieties. The reactive moiety on the binding moiety can also include amine for targeting aldehydes, amine for targeting maleimide (e.g., free thiols), azide for targeting click chemistry compounds (e.g., alkynes), biotin for targeting streptavidin, phosphates for targeting EDC, which in turn targets active ester (e.g., $NH_2$). The reactive moiety on the binding moiety can be a chemical compound or group that binds to the reactive moiety on the analyte binding moiety. Exemplary strategies to conjugate the binding moiety to the target-specific barcode domain and/or the sample-specific barcode domain include the use of commercial kits (e.g., Solulink, Thunder link), conjugation of mild reduction of hinge region and maleimide labeling, stain-promoted click chemistry reaction to labeled amides (e.g., copper-free), and conjugation of periodate oxidation of sugar chain and amine conjugation. In the cases where the binding moiety is an antibody, the antibody can be modified prior to or contemporaneously with conjugation of the oligonucleotide.

In some embodiments, the barcode domain coupled to a labeling agent can include modifications that render it non-extendable by a polymerase. In some embodiments, the barcode domain can serve as a template. A modification for blocking primer extension by a polymerase can be a carbon spacer group of different lengths or a dideoxynucleotide. In some embodiments, the modification can be an abasic site that has an apurine or apyrimidine structure, a base analog, or an analogue of a phosphate backbone, such as a backbone of N-(2-aminoethyl)-glycine linked by amide bonds, tetrahydrofuran, or 1', 2'-Dideoxyribose. The modification can also be a uracil base, 2'OMe modified RNA, C3-18 spacers (e.g., structures with 3-18 consecutive carbon atoms, such as C3 spacer), ethylene glycol multimer spacers (e.g., spacer 18 (hexa-ethyleneglycol spacer), biotin, di-deoxynucleotide triphosphate, ethylene glycol, amine, or phosphate.

In some embodiments, the barcode domain coupled to the binding moiety includes a cleavable domain. For example, after the labeling agent binds to a target (e.g., a cell surface molecule), the barcode domain can be cleaved and collected for downstream analysis according to the methods as described herein. In some embodiments, the cleavable domain of the barcode domain includes a U-excising element that allows the species to release from the bead. In some embodiments, the U-excising element can include a single-stranded DNA (ssDNA) sequence that contains at least one uracil. The species can be attached to a bead via the ssDNA sequence. The species can be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment can be included in downstream processing to eliminate the phosphate group, e.g., prior to ligation of additional elements.

In some embodiments, a binding moiety of a labeling agent includes one or more antibodies or epitope binding fragments thereof. The antibodies or epitope binding fragments including the binding moiety can specifically bind to a target. In some embodiments, the target is a protein (e.g., a protein on a surface of the biological sample (e.g., a cell) or an intracellular protein). In some embodiments, a plurality of labeling agents comprising a plurality of binding moieties bind a plurality of targets present in a biological sample. In some embodiments, the plurality of targets includes a single species of target (e.g., a single species of polypeptide). In some embodiments in which the plurality of targets includes a single species of target, the binding moieties of the plurality of labeling agents are the same. In some embodiments in which the plurality of targets includes a single species of target, the binding moieties of the plurality of labeling agents are different (e.g., members of the plurality of labeling agents can have two or more species of binding moieties, wherein each of the two or more species of binding moieties binds a single species of target, e.g., at different binding sites). In some embodiments, the plurality of targets includes multiple different species of target (e.g., multiple different species of polypeptides).

In some embodiments, multiple different species of targets (e.g., polypeptides) from the biological sample can be subsequently associated with the one or more physical properties of the biological sample. For example, the multiple different species of targets can be associated with locations of the targets in the biological sample. Such information (e.g., proteomic information when the binding moiety(ies) recognizes a polypeptide(s)) can be used in association with other spatial information (e.g., genetic information from the biological sample, such as DNA sequence information, transcriptome information (e.g., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by a labeling agent comprising a binding moiety that binds to the cell surface protein and a target-specific barcode that identifies that binding moiety, and the cell can be subjected to in situ analysis. Profiles of individual cells or populations of cells can be compared to profiles from other cells, e.g., 'normal' cells, to identify variations in analytes, which can provide diagnostically relevant information. In some embodiments, these profiles can be useful in the diagnosis of a variety of disorders that are characterized by variations in cell surface receptors, such as cancer and other disorders.

B. Barcoding a Biological Sample

In some embodiments, provided herein are methods and materials for attaching and/or introducing a molecule (e.g., a reporter oligonucleotide molecule) having a barcode (e.g., a sample-specific barcode) to a biological sample (e.g., to a cell in a biological sample) for use in in situ analysis. In some embodiments, a plurality of molecules (e.g., a plurality of reporter oligonucleotide molecules) having a plurality of barcodes (e.g., a plurality of sample-specific and/or target-specific barcodes) are introduced to a biological sample (e.g., to a plurality of cells in a biological sample) for use in in situ analysis.

Cells in the biological sample can be tagged using either covalent conjugation of the labeling agent to the cell surface or non-covalent interactions with cell membrane elements. A non-exhaustive list of a covalent labeling agent/cell surface interactions, including protein targeting, amine conjugation using NHS chemistry, cyanuric chloride, thiol conjugation via maleimide addition, as well as targeting glycoproteins/glycolipids expressed on the cell surface via click chemistry. Non-exhaustive examples of non-covalent interactions with cell membrane elements include lipid modified oligos, biocompatible anchor for cell membrane (oleyl-PEG-NHS), lipid modified positive neutral polymer, and antibody to membrane proteins. In some embodiments, physical force is used to facilitate attachment to or introduction of a molecule (e.g., a reporter oligonucleotide molecule) attached to a binding moiety and having a barcode into a biological sample (e.g., a cell present in a biological sample).

In some embodiments, the binding moiety can directly bind to one or more molecules in the cell. In some embodiments, the binding moiety can indirectly bind to one or more molecules in and/or on the cell. In some embodiments, the antibodies or epitope binding fragments including the binding moiety binds to a surface of the cell or is internal to the cell.

In some embodiments, biological samples (e.g., cells in a biological sample) can be labeled using labeling agents where the labeling agents comprises a binding moiety (e.g., polynucleotide), a molecule (e.g., reporter oligonucleotide)

having barcodes (e.g., sample-specific barcodes). In some embodiments, a labeling agent includes a barcode (e.g., a sample-specific barcode or a target-specific barcode). The barcode of a barcoded labeling agent can be any of the variety of barcodes described herein. In some embodiments, the barcode of a barcoded labeling agent is a sample-specific barcode corresponding to a sample from which the labeled cell is derived. In some embodiments, the barcode of a barcoded labeling agent is a sample-specific barcode corresponding to a sample containing the cell prior to labeling. In some embodiments, the sample-specific barcode sequence is in the reporter oligonucleotide. In some embodiments, the barcode of a barcoded labeling agent is a target-specific barcode. In some embodiments, the barcode of a barcoded labeling agent identifies the associated molecule, where each target-specific barcode is associated with a particular molecule. In some embodiments, the target specific barcode corresponds to the binding moiety or the target. In some embodiments, the target-specific barcode sequence is in the reporter oligonucleotide. In some embodiments, the sample-specific barcode and the target specific barcode can be the same or different. In some embodiments, the sample-specific barcode and the target specific barcode are in the same oligonucleotide or in different oligonucleotides separately conjugated to the binding moiety. In some embodiments, the target specific barcode sequence and the sample specific barcode sequence at least partially overlap in sequence.

In some embodiments, the barcode of a barcoded labeling agent corresponds to a cell feature. In some embodiments, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some embodiments, cell features may include intracellular analytes, such as proteins, protein modifications (e.g., phosphorylation status or other post-translational modifications), nuclear proteins, nuclear membrane proteins, or any combination thereof.

In some embodiments, one or more molecules are applied to a sample. In some embodiments, a nucleic acid molecule (e.g., reporter oligonucleotide molecule) that includes the barcode is covalently attached to the binding moiety. In some embodiments, a nucleic acid molecule (e.g., reporter oligonucleotide molecule) that includes the barcode is non-covalently attached to the binding moiety. A non-limiting example of non-covalent attachment includes hybridizing the nucleic acid molecule (e.g., reporter oligonucleotide molecule) that includes the barcode to a nucleic acid molecule on the binding moiety. In some embodiments, a nucleic acid molecule that is attached to a binding moiety that includes a barcode also includes one or more additional domains. Such additional domains include, without limitation, a PCR handle, a sequencing priming site, a domain for hybridizing to another nucleic acid molecule, and combinations thereof.

In some embodiments, a binding moiety attaches to the surface of a cell. When the binding moiety includes a barcode (e.g., a reporter oligonucleotide molecule that includes a sample-specific barcode), the barcode is also attached to the surface of the cell. In some embodiments, a binding moiety attaches covalently to the cell surface to facilitate introduction of the barcode sequence. In some embodiments, a binding moiety attaches non-covalently to the cell surface to facilitate introduction of the barcode sequence. In some embodiments, the binding moiety can bind to one or more molecules on the cell surface via a linker. In some embodiments, the linker comprises one or more of a N-hydroxysuccinimide (NHS) linker, a bifunctional NHS linker, an azide, an alkyne, glycol chitosan, 1,2-distearoyl-sn-glycero-3-phosphoethanolamine-Poly (ethylene glycol) (DSPE-PEG), and succinimidyl-3-(2-pyridyldithio)propionate (SPDP). Exemplary linkers include those described in US 2021/0332425 which is incorporated herein by reference in its entirety for all purposes.

In some embodiments, the biological sample is dissociated into single cells using any of the methods described herein, prior to labeling with a labeling agent(s). In some embodiments, the biological sample is labeled prior to being dissociated into single cells. Once a cell or cells in a biological sample is labeled with a labeling agent(s), the cells from a plurality of biological samples are combined for an in situ analysis. In some embodiments, such in situ analysis includes immobilizing the labeled cells of multiple biological samples (or a subset of the biological samples) and analyzing analytes present in those cells at a single cell resolution. Any of a variety of methods for analyzing analytes present in cells at a single cell resolution can be used. The cells can be permeabilized as necessary (e.g., using permeabilization agents and methods described herein), reagents for analyte analysis can be provided to the cells (e.g., a reverse transcriptase, a polymerase, nucleotides, etc.), and the analytes can be assayed in situ.

In any of the embodiments herein, a method for cell analysis comprises (a) providing a population of cells comprising labeled cells and (b) depositing the labeled cells on a substrate. In any of the embodiments herein, the labeled cell is not in a partition prior to, during, and/or after the providing step in (a) or during the depositing in step (b). In some embodiments, the labeled cell is not partitioned in a partition (e.g., an emulsion droplet or a microwell) throughout the providing step, the immobilizing step, the contacting step, and/or the detecting step. In some embodiments, the partition is an emulsion droplet or a microwell. In any of the embodiments herein, the labeled cell is not lysed or homogenized prior to and/or during the depositing in step (b). In some embodiments, the cell is not lysed or homogenized after being labeled with the labeling agent. In some embodiments, the labeled cell is not lysed or homogenized throughout the providing step, the immobilizing step, the contacting step, and/or the detecting step, although the labeled cell may be permeabilized, fixed, crosslinked/de-crosslinked, embedded in a matrix, cleared, and/or otherwise treated. In some embodiments, a nucleic acid of the labeled cell is not released from the cell between the providing step (a) and the depositing in step (b). In some embodiments, the nucleic acid is the reporter oligonucleotide or a cellular DNA or RNA molecule of the cell.

In any of the embodiments herein, a nucleic acid of the labeled cell is not extended and/or reverse transcribed by a polymerase, ligated to another nucleic acid, amplified, and/or sequenced between the providing step (a) and the depositing in step (b). In any of the embodiments herein, wherein a nucleic acid of the labeled cell is not released from the cell between the providing step (a) and the depositing in step (b).

C. Introducing a Binding Moiety to the Surface of a Cell

Non-limiting examples of binding moieties and systems that attach to the surface of a cell (e.g., thus introducing the binding moiety and any barcode attached thereto to the exterior of the cell) that can be used in accordance with materials and methods provided herein for profiling an analyte or analytes in a biological sample include lipophilic moieties conjugated to oligonucleotides, positive or neutral oligo-conjugated polymers, antibody conjugated oligonucleotides, streptavidin-conjugated oligonucleotides, dye-tagged oligonucleotides, click-chemistry, receptor-ligand systems, covalent binding systems via amine or thiol functionalities, azide-based systems, lectin-based systems, and combinations thereof.

i. Labeling Agents Comprising Lipophilic Moieties

In some embodiments, the binding moiety in a labeling agent can comprise a lipid moiety, such as a lipid anchor that is antigen independent and inserts universally into the cell or nucleus membrane, irrespective of cell or sample type. In some embodiments, a labeling agent comprising such a lipid-based binding moiety can be used to barcode samples in a sample-agnostic manner. In some embodiments, the binding moiety comprises cholesterol or a derivative thereof.

In some embodiments, a molecule (e.g., a reporter oligonucleotide molecule) having a barcode (e.g., a sample-specific barcode) is coupled to a lipophilic molecule. In some embodiments, the lipophilic molecule enables the delivery of the molecule to the cell membrane or the nuclear membrane. In some embodiments, a molecule (e.g., a reporter oligonucleotide molecule) having a barcode (e.g., a sample-specific barcode) coupled to a lipophilic molecule can associate with and/or insert into lipid membranes such as cell membranes and nuclear membranes. In some cases, the insertion can be reversible. In some cases, the association between the lipophilic molecule and the cell may be such that the cell retains the lipophilic molecule (e.g., and associated components, such as reporter oligonucleotide and the barcode sequence) during subsequent processing (e.g., cell permeabilization, amplification, pooling, etc.). In some embodiments, a molecule (e.g., a reporter oligonucleotide molecule) having a barcode (e.g., a sample-specific barcode) coupled to a lipophilic molecule may enter into the intracellular space and/or a cell nucleus. The sample-specific nucleic acid barcode coupled to a lipophilic molecule can be used to label cells by delivering the nucleic acid barcode molecule to a cell membrane or a nuclear membrane by the lipophilic molecule. Lipophilic molecules can associate with and/or insert into lipid membranes such as cell membranes and nuclear membranes. In some cases, the insertion can be reversible. In some cases, the association between the lipophilic molecule and the cell may be such that the cell retains the lipophilic molecule (e.g., and associated components, such as nucleic acid barcode molecules, thereof) during subsequent processing (e.g., cell permeabilization, amplification, pooling, etc.).

Non-limiting examples of lipophilic molecules that can be used in embodiments described herein include sterol lipids such as cholesterol, tocopherol, steryl, palmitate, lignoceric acid, and derivatives thereof. In some embodiments, the lipophilic molecules are neutral lipids that are conjugated to hydrophobic moieties (e.g., cholesterol, squalene, or fatty acids) (See Raouane et al. Bioconjugate Chem., 23(6):1091-1104 (2012) the content of which is herein incorporated by reference in its entirety). In some embodiments, a molecule (e.g., a nucleic acid molecule) having a barcode (e.g., a sample-specific barcode) may be attached to the lipophilic moiety via a linker, such as a tetra-ethylene glycol (TEG) linker. Other exemplary linkers include, but are not limited to, Amino Linker C6, Amino Linker C12, Spacer C3, Spacer C6, Spacer C12, Spacer 9, and Spacer 18. In some embodiments, a molecule (e.g., a nucleic acid molecule) having a barcode (e.g., a sample-specific barcode) is indirectly coupled (e.g., via hybridization or ligand-ligand interactions, such as biotin-streptavidin) to a lipophilic molecule. Other lipophilic molecules that may be used in accordance with methods provided herein include amphiphilic molecules wherein the head group (e.g., charge, aliphatic content, and/or aromatic content) and/or fatty acid chain length (e.g., C12, C14, C16, or C18) can be varied. For instance, fatty acid side chains (e.g., C12, C14, C16, or C18) can be coupled to glycerol or glycerol derivatives (e.g., 3-t-butyldiphenylsilylglycerol), which can also comprise, e.g., a cationic head group. In some embodiments, a molecule (e.g., a reporter oligonucleotide molecule) having a barcode (e.g., a sample-specific barcode) disclosed herein can then be coupled (either directly or indirectly) to these amphiphilic molecules. In some embodiments, a molecule (e.g., a reporter oligonucleotide molecule) having a barcode (e.g., a sample-specific barcode) coupled to an amphiphilic molecule may associate with and/or insert into a membrane (e.g., a cell, cell bead, or nuclear membrane). In some cases, an amphiphilic or lipophilic moiety may cross a cell membrane and provide a molecule (e.g., a reporter oligonucleotide molecule) having a barcode (e.g., a sample-specific barcode) to an internal region of a cell and/or cell bead.

In some embodiments, wherein the molecule (e.g., a reporter oligonucleotide molecule) has an amino group within the molecule, the molecule (e.g., a reporter oligonucleotide molecule) having a barcode (e.g., a sample-specific barcode) and an amino group can be coupled to an amine-reactive lipophilic molecule. For example, a molecule (e.g., a reporter oligonucleotide molecule) having a barcode and an amino group can be conjugated to DSPE-PEG(2000)-cyanuric chloride (1,2-distearoyl-sn-glycero-3-phosphoethanolamine-N-[cyanur(polyethylene glycol)-2000]).

In some embodiments, a binding moiety can attach to a surface of a cell through a combination of lipophilic and covalent attachment. For example, an oligonucleotide attached to a lipid to target the oligonucleotide to a cell membrane comprises an amine group that can be covalently linked to a cell surface protein(s) via any number of chemistries described herein. In these embodiments, the lipid can increase the surface concentration of the oligonucleotide and can promote the covalent reaction. In some cases, a lipophilic molecule may comprise a label, such as an optical label. Such a label may, for example, enable detection of a moiety with which the lipophilic molecule is associated. For example, a lipophilic molecule may comprise a fluorescent moiety. The fluorescent moiety may permit optical detection of the lipophilic molecule and moieties with which it is associated.

ii. Positive or Neutral Oligo-Conjugated Polymers

In some embodiments, a molecule (e.g., a reporter oligonucleotide molecule) having a barcode (e.g., a sample-specific barcode) can be coupled to a glycol chitosan derivative. The glycol chitosan derivative (e.g., glycol chitosan-cholesterol) can serve as a hydrophobic anchor (see Wang et al. J. Mater. Chem. B., 30:6165 (2015), the content of which is herein incorporated by reference in its entirety). Non-limiting examples of chitosan derivatives that can be coupled to a molecule (e.g., a reporter oligonucleotide molecule) having a barcode (e.g., a sample-specific barcode) can be found in Cheung et al., Marine Drugs, 13(8): 5156-5186 (2015), which is herein incorporated by reference in its entirety.

iii. Antibody-Based Labeling Agents

In some embodiments, a molecule (e.g., a reporter oligonucleotide molecule) having a barcode (e.g., a sample-specific barcode) can be coupled to an antibody or epitope binding fragment thereof in a manner that facilitates attachment of the molecule (e.g., a reporter oligonucleotide molecule) having a barcode (e.g., a sample-specific barcode) to the surface of a cell. In some embodiments, facilitating attachment to the cell surface facilitates introduction of the molecule (e.g., a reporter oligonucleotide molecule) having a barcode (e.g., a sample-specific barcode) into the cell. In some embodiments, the molecule (e.g., a reporter oligonucleotide molecule) having a barcode (e.g., a sample-specific barcode) can be coupled to an antibody that is directed to an antigen that is present on the surface of a cell. In some embodiments, the molecule (e.g., a reporter oligonucleotide molecule) having a barcode (e.g., a sample-specific barcode) can be coupled to an antibody that is directed to an antigen that is present on the surface of a plurality of cells (e.g., a plurality of cells in a biological sample). In some embodiments, the molecule (e.g., a reporter oligonucleotide molecule) having a barcode (e.g., a sample-specific barcode) can be coupled to an antibody that is directed to an antigen that is present on the surface of all or substantially all the cells present in a biological sample. Any of the exemplary methods described herein of attaching a molecule (e.g., a reporter oligonucleotide molecule) having a barcode (e.g., a sample-specific barcode) to another molecule (e.g., binding moiety) can be used.

In some embodiments, a reporter oligonucleotide comprising a barcode (e.g., a sample-specific barcode) can be coupled to an antibody or epitope binding fragment thereof that binds to an antigen that is ubiquitously expressed on and/or in cells of a sample, for example, cell surface markers CD298 and/or β2-microglobulin. In some embodiments, the antigen is ubiquitously expressed on and/or in cells of a sample. In some embodiments, the antigen is expressed on and/or in at least 50%, at least 55%, at least 60%, at least 65%, at least 70%, at least 75%, at least 80%, at least 85%, at least 90%, at least 95%, or at least 99% of the cells of a sample.

iv. Streptavidin-Conjugated Oligonucleotides

In some embodiments, a molecule (e.g., a reporter oligonucleotide molecule) having a barcode (e.g., a sample-specific barcode) can attach to the surface of a cell using biotin-streptavidin. In some embodiments, primary amines in the side chain of lysine residues of cell surface polypeptides are labeled with NHS-activated biotin reagents. For example, the N-terminus of a polypeptide can react with NHS-activated biotin reagents to form stable amide bonds. In some embodiments, binding moieties include molecules (e.g., a reporter oligonucleotide molecule) having barcodes (e.g., a sample-specific barcode) conjugated to streptavidin. In some cases, streptavidin can be conjugated to the molecule (e.g., a reporter oligonucleotide molecule) having a barcode using click chemistry (e.g., maleimide modification) as described herein. In some embodiments, a cell containing NHS-activated biotin incorporated into lysine side chains of a cell surface protein forms a non-covalent bond with the streptavidin conjugated to the molecule (e.g., a reporter oligonucleotide molecule) having a barcode (e.g., a sample-specific barcode). In some embodiments, the molecule (e.g., a reporter oligonucleotide molecule) having a barcode (e.g., a sample-specific barcode) conjugated to streptavidin is itself part of a binding moiety.

v. Dye-Tagged Oligonucleotides

In some embodiments, a molecule (e.g., a reporter oligonucleotide molecule) having a barcode (e.g., a sample-specific barcode) is directly linked to a fluorescent tag. In some embodiments, the physical properties of the fluorescent tags (e.g., hydrophobic properties) can overcome the hydrophilic nature of the molecule (e.g., a reporter oligonucleotide molecule) having a barcode (e.g., a sample-specific barcode). For example, in some embodiments, wherein the molecule is a reporter oligonucleotide molecule, a fluorescent tag (e.g., BODIPY, Cy3, Atto 647N, and Rhodamine Red C2) can be coupled to a 5' end of the reporter oligonucleotide molecule having a barcode (e.g., a sample-specific barcode). In some embodiments, wherein the molecule is a reporter oligonucleotide molecule, any fluorescent tag having hydrophobic properties can be coupled to the reporter oligonucleotide molecule having a barcode (e.g., a sample-specific barcode) in a manner that overcomes the hydrophilic nature of the nucleic acid molecule. Non-limiting examples of fluorescent tags with hydrophobic properties include BODIPY, Cy3, Atto 647N, and Rhodamine Red C2. In some embodiments, a fluorescent tag is part of a binding moiety.

vi. Chemical Conjugation Including Click Chemistry Conjugation

Methods of generating surface-indexed cells can generally include functionalizing the cell surface with a labeling agent that may be attached (1) directly to oligonucleotide sequences or (2) indirectly to oligonucleotide sequences through the use of linkers. In other embodiments, the oligonucleotide may be attached directly to the surface of the cell through a covalent bond. In some embodiments, primary amines in the side chain of lysine residues of cell surface polypeptides are labeled with functionalized molecules comprising oligonucleotides, such as NHS-activated molecules. For example, the N-terminus of a polypeptide can react with an NHS-activated reagent to form stable amide bonds. In some instances, a cell is contacted with an agent (e.g. a chemical agent) that generates functional groups on the surface of a cell (e.g., on proteins on the surface of the cell). In some embodiments, a component on the surface of the cell (e.g., a surface protein or carbohydrate) comprises or is modified to comprise a —COOH (carboxylic acid), —$NH_2$ (amine), —$CH_2Cl$ (chloromethyl), —$CONH_2$ (amide), —$CONHNH_2$ (hydrazide), —CHO (aldehyde), —OH (hydroxyl), —SH (thiol), —COC— (epoxy), click chemistry functional group, or maleimido group. An oligonucleotide can then be reacted with the functional group to attach the oligonucleotide to the cell surface. In some instances, the oligonucleotide comprises a functional group that reacts with the functional group on the cell surface. In some embodiments, the oligonucleotide to be conjugated to the cell surface comprises an amino modification, a thiol modification, or an acrydite modification. In some embodiments, the oligonucleotide and the cell surface are each functionalized with a click chemistry functional group (such as constituents of a copper-free click chemistry, e.g., SPAAC) as described in, e.g., Takayama et al., Click Chemistry as a Tool for Cell Engineering and Drug Delivery; Molecules 2019, 24(1), 172. In some embodiments, chemical cross-linkers are utilized to couple the oligonucleotide to component on the cell surface. In some instances, commercial conjugation kits and chemistries (such as Lightning-Link®, Thunder-Link®, or Protein-Oligonucleotide Conjugation Kit (HyNic/4FB conjugation—Solulink) are utilized to attach the oligonucleotide to a component on the cell surface.

In some embodiments, molecules (e.g., a reporter oligonucleotide molecule) having barcodes (e.g., a sample-specific barcode) are coupled to click-chemistry moieties. In some embodiments, click chemistry comprises reactions that are modular, wide in scope, give high yields, generate only inoffensive byproducts, such as those that can be removed by nonchromatographic methods, and are stereospecific (but not necessarily enantioselective) (see, e.g., Angew. Chem. Int. Ed., 2001, 40(11):2004-2021, the content of which is herein incorporated by reference in its entirety). In some cases, click chemistry can describe pairs of functional groups that can selectively react with each other in mild, aqueous conditions.

An example of a click chemistry reaction is the Huisgen 1,3-dipolar cycloaddition of an azide and an alkyne, e.g., copper-catalysed reaction of an azide with an alkyne to form the 5-membered heteroatom ring 1,2,3-triazole. The reaction is also known as a Cu(I)-Catalyzed Azide-Alkyne Cycloaddition (CuAAC), a Cu(I) click chemistry or a Cu+ click chemistry. Catalysts for the click chemistry include, but are not limited to, Cu(I) salts, or Cu(I) salts made in situ by reducing Cu(II) reagents to Cu(I) reagents with a reducing reagent (Pharm Res. 2008, 25(10): 2216-2230, which is incorporated herein by reference in its entirety). Cu(II) reagents for the click chemistry can include, but are not limited to, the Cu(II)-(TBTA) complex and the Cu(II) (THPTA) complex. TBTA, which is tris-[(1-benzyl-1H-1,2,3-triazol-4-yllmethyl]amine, also known as tris-(benzyltriazolylmethyl)amine, can be a stabilizing ligand for Cu(I) salts. THPTA, which is tris-(hydroxypropyltriazolylmethyl) amine, is another example of a stabilizing agent for Cu(I). Other conditions can also be used to construct the 1,2,3-triazole ring from an azide and an alkyne using copper-free click chemistry, such as the Strain-promoted Azide-Alkyne Click chemistry reaction (SPAAC) (see, e.g., Chem. Commun., 2011, 47:6257-6259 and Nature, 2015, 519(7544): 486-90, all of which are herein incorporated by reference in their entireties).

vii. Receptor-Ligand Systems

In some embodiments, a molecule (e.g., a reporter oligonucleotide molecule) having a barcode (e.g., a sample-specific barcode) can be coupled to a ligand, wherein the ligand is part of a receptor-ligand interaction on the surface of a cell. For example, a molecule (e.g., a reporter oligonucleotide molecule) having a barcode (e.g., a sample-specific barcode) can be coupled to a ligand that interacts selectively with a cell surface receptor thereby targeting the molecule (e.g., a reporter oligonucleotide molecule) having a barcode (e.g., a sample-specific barcode) to a specific cell. Non-limiting examples of receptor-ligand systems that can be used include integrin receptor-ligand interactions, GPCR receptor-ligand interactions, RTK receptor-ligand interactions, and TLR-ligand interactions (see Juliano, Nucleic Acids Res., 44(14): 6518-6548 (2016), the content of which is herein incorporated by reference in its entirety). Any of the methods described herein for attaching a molecule (e.g., a reporter oligonucleotide molecule) having a barcode (e.g., a sample-specific barcode) to a ligand (e.g., any of the methods described herein relating to attaching a molecule (e.g., a reporter oligonucleotide molecule) having a barcode (e.g., a sample-specific barcode) to an antibody) can be used. In some embodiments, a ligand is part of a binding moiety.

viii. Covalent Binding Systems Via Amine or Thiol Functionalities

In some embodiments, a molecule (e.g., a reporter oligonucleotide molecule) having a barcode (e.g., a sample-specific barcode) can incorporate reactive functional groups at sites within the molecule (e.g., a reporter oligonucleotide molecule). In such cases, the reactive functional groups can facilitate conjugation to ligands and/or surfaces. In some embodiments, a molecule (e.g., a reporter oligonucleotide molecule) having a barcode (e.g., a sample-specific barcode) can include thiol modifiers that are designed to react with a broad array of activated accepting groups (e.g., maleimide and gold microspheres). For example, a molecule (e.g., a reporter oligonucleotide molecule) having a barcode (e.g., a sample-specific barcode) having thiol modifiers can interact with a maleimide-conjugated peptide thereby resulting in labeling of the peptide. In some embodiments, maleimide-conjugated peptides are present on the surface of a cell whereupon interaction with the thiol-modified molecule (e.g., a reporter oligonucleotide molecule) having a barcode (e.g., a sample-specific barcode), the molecule (e.g., a reporter oligonucleotide molecule) having a barcode (e.g., a sample-specific barcode) is coupled to the surface of the cell. Non-limiting examples of thiol modifiers include: 5' thiol modifier C6 S-S, 3' thiol modifier C3 S-S, dithiol, 3'thiol modifier oxa 6-S-S, and dithiol serinol. In some embodiments, reactive functionals groups are part of a binding moiety.

In some embodiments, a molecule (e.g., a reporter oligonucleotide molecule) having a barcode (e.g., a sample-specific barcode) can include amine modifiers, e.g., amine modifiers that are designed to attach to another molecule in the presence of an acylating agent. In some embodiments, a molecule (e.g., a reporter oligonucleotide molecule) having a barcode (e.g., a sample-specific barcode) can include amine modifiers that are designed to attach to a broad array of linkage groups (e.g., carbonyl amide, thiourea, sulfonamide, and carboxamide). For example, a molecule (e.g., a reporter oligonucleotide molecule) having a barcode (e.g., a sample-specific barcode) and an amine modifier can interact with a sulfonamide-conjugated peptide thereby resulting in labeling of the peptide. In some embodiments, sulfonamide-conjugated peptides are present on the surface of a cell whereupon interaction with the amine-modified molecule (e.g., a reporter oligonucleotide molecule) having a barcode (e.g., a sample-specific barcode), the molecule (e.g., a reporter oligonucleotide molecule) having a barcode (e.g., a sample-specific barcode) is coupled to the surface of the cell. Non-limiting example of amine modifiers include: DMS(O) MT-Amino-Modifier-C6, Amino-Modifier-C3-TFA, Amino-Modifier-C12, Amino-Modifier-C6-TFA, Amino-dT, Amino-Modifier-5, Amino-Modifier-C2-dT, Amino-Modifier-C6-dT, and 3'-Amino-Modifier-C7. In some embodiments, amine modifiers are part of a binding moiety.

As another example, a molecule (e.g., a reporter oligonucleotide molecule) having a barcode (e.g., a sample-specific barcode) can incorporate reactive functional groups at sites within the molecule (e.g., a reporter oligonucleotide molecule) such as N-hydroxysuccinimide (NHS). In some embodiments, amines (e g, amine-containing peptides) are present on the surface of a cell whereupon interaction with the NHS-modified molecule (e.g., a reporter oligonucleotide molecule) having a barcode (e.g., a sample-specific barcode) the molecule (e.g., a reporter oligonucleotide molecule) having a barcode (e.g., a sample-specific barcode) is coupled to the surface of the cell. In some embodiments, a molecule (e.g., a reporter oligonucleotide molecule) having a barcode (e.g., a sample-specific barcode) is reacted with a bifunctional NHS linker to form an NHS-modified molecule (e.g., a nucleic acid molecule) having a barcode.

In some embodiments, a molecule (e.g., a reporter oligonucleotide molecule) having a barcode (e.g., a sample-specific barcode) can be coupled to a biocompatible anchor for cell membrane (BAM). For example, a BAM can include molecules that comprise an oleyl group and PEG. The oleyl group can facilitate anchoring the molecule (e.g., a nucleic acid molecule) having a barcode (e.g., a sample-specific barcode) to a cell, and the PEG can increase water solubility. In some embodiments, oleyl-PEG-NHS can be coupled to a molecule (e.g., a reporter oligonucleotide molecule) having a barcode (e.g., a sample-specific barcode) using NHS chemistry.

ix. Azide-Based Systems

In some embodiments, wherein the molecule (e.g., a reporter oligonucleotide molecule) incorporates reactive functional groups at sites within the molecule, a molecule (e.g., a reporter oligonucleotide molecule) having a barcode (e.g., a sample-specific barcode) can be coupled to an azide group on a cell surface. In some embodiments, the reactive functional group is an alkynyl group. In some embodiments, click chemistry as described herein can be used to attach the alkynyl-modified molecule (e.g., a reporter oligonucleotide molecule) having a barcode (e.g., a sample-specific barcode) to an azide group on the cell surface. An azide group can be attached to the cell surface through a variety of methods. For example, NHS chemistry can be used to attach an azide group to the cell surface. In some embodiments, N-azidoacetylmannosamine-tetraacylated (Ac4ManNAz), which contains an azide group, can react with sialic acid on the surface of a cell to attach azide to the cell surface. In some embodiments, azide is attached to the cell surface by bioorthogonal expression of azide.

x. Lectin-Based Systems

In some embodiments, a molecule (e.g., a reporter oligonucleotide molecule) having a barcode (e.g., a sample-specific barcode) can be coupled to a lectin that facilitates attachment of the molecule (e.g., a reporter oligonucleotide molecule) having a barcode (e.g., a sample-specific barcode) to a cell surface. Lectin can bind to glycans, e.g., glycans on the surface of cells. In some embodiments, the molecule (e.g., a reporter oligonucleotide molecule) having a barcode (e.g., a sample-specific barcode) has an incorporated reactive functional group such as an azide group. In some embodiments, the molecule (e.g., a reporter oligonucleotide molecule) having a barcode (e.g., a sample-specific barcode) and an azide group is reacted with a modified lectin, e.g., a lectin modified using NHS chemistry to introduce an azide reactive group. In some embodiments, a live cell is labeled with a lectin-modified molecule (e.g., a reporter oligonucleotide molecule) having a barcode (e.g., a sample-specific barcode). In some embodiments, a fixed cell is labeled with a lectin-modified molecule (e.g., a reporter oligonucleotide molecule) having a barcode (e.g., a sample-specific barcode). In some embodiments, a permeabilized cell is labeled with a lectin-modified molecule (e.g., a reporter oligonucleotide molecule) having a barcode (e.g., a sample-specific barcode). In some embodiments, organelles in the secretory pathway can be labeled with a lectin-modified molecule (e.g., a reporter oligonucleotide molecule) having a barcode (e.g., a sample-specific barcode).

D. Introducing a Binding Moiety to the Interior of a Cell

Non-limiting examples of binding moieties and systems that penetrate and/or pass through the cell membrane (e.g., thus introducing the binding moiety, reporter oligonucleotide, and any barcode attached thereto to the interior of the cell) that can be used in accordance with materials and methods provided herein for profiling an analyte or analytes in a biological sample include: a cell-penetrating agent (e.g., a cell-penetrating peptide), a nanoparticle, a liposome, a polymersome, a peptide-based chemical vector, electroporation, sonoporation, lentiviral vectors, retroviral vectors, and combinations thereof.

Non-exhaustive examples of oligo delivery vehicles may include a cell penetrating peptide or a nanoparticle. Non-exhaustive examples of the delivery systems can include lipid-based polymeric and metallic nanoparticles or oligos that can be conjugated or encapsulated within the delivery system.

i. Cell-Penetrating Agent

In some embodiments, binding of a cell feature (e.g., a molecule on and/in a cell) by a molecule (e.g., a labeling agent) having a barcode (e.g., a sample-specific barcode) and a binding moiety is facilitated by a cell-penetrating agent. In some embodiments, a molecule (e.g., a reporter oligonucleotide molecule) having a barcode (e.g., a sample-specific barcode) and a binding moiety is coupled to a cell-penetrating agent, and the cell-penetrating agent allows the molecule to interact with an analyte inside the cell. In some embodiments, a cell-penetrating agent is an agent capable of facilitating the introduction of a molecule (e.g., a reporter oligonucleotide molecule) having a barcode (e.g., a sample-specific barcode) and a binding moiety into a cell of a biological sample (see, e.g., Lovatt et al. Nat Methods. 2014 February; 11(2):190-6, the content of which is herein incorporated by reference in its entirety). In some embodiments, a cell-penetrating agent is a cell-penetrating peptide. In some embodiments, a "cell-penetrating peptide" comprises a peptide (e.g., a short peptide, e.g., a peptide not usually exceeding 30 residues) that has the capacity to cross cellular membranes.

In some embodiments, a cell-penetrating peptide coupled to a molecule (e.g., a reporter oligonucleotide molecule) having a barcode (e.g., a sample-specific barcode) and a binding moiety can cross a cellular membrane using an energy dependent or an energy independent mechanism. For example, a cell-penetrating peptide can cross a cellular membrane through direct translocation through physical perturbation of the plasma membrane, endocytosis, adaptive translocation, pore-formation, electroporation-like permeabilization, and/or entry at microdomain boundaries. Non-limiting examples of a cell-penetrating peptide include: penetratin, tat peptide, pVEC, transportan, MPG, Pep-1, a polyarginine peptide, MAP, R6W3, (D-Arg)9, Cys(Npys)-(D-Arg)9, Anti-BetaGamma (MPS—Phosducin—like protein C terminus), Cys(Npys) antennapedia, Cys(Npys)-(Arg) 9, Cys(Npys)-TAT (47-57), HIV-1 Tat (48-60), KALA, mastoparan, penetratin-Arg, pep-1-cysteamine, TAT(47-57) GGG-Cys(Npys), Tat-NR2Bct, transdermal peptide, SynB1, SynB3, PTD-4, PTD-5, FHV Coat-(35-49), BMV Gag-(7-25), HTLV-II Rex-(4-16), R9-tat, SBP, FBP, MPG, MPG (ANLS), Pep-2, MTS, plsl, and a polylysine peptide (see, e.g., Bechara et al. FEBS Lett. 2013 Jun. 19; 587(12):1693-702, the content of which is herein incorporated by reference in its entirety).

ii. Nanoparticles

In some embodiments, binding of a cell feature (e.g., a molecule on and/in a cell) by a molecule (e.g., a labeling agent) having a barcode (e.g., a sample-specific barcode) and a binding moiety is facilitated by an inorganic particle (e.g., a nanoparticle). In some embodiments, a molecule (e.g., a reporter oligonucleotide molecule) having a barcode (e.g., a sample-specific barcode) and a binding moiety is coupled to an inorganic particle (e.g., a nanoparticle), and the molecule (e.g., a reporter oligonucleotide molecule) having a barcode (e.g., a sample-specific barcode) and a binding moiety uses the nanoparticle to get access to analytes inside the cell. Non-limiting examples of nanoparticles that can be used in embodiments herein to deliver a molecule (e.g., a reporter oligonucleotide molecule) having a barcode (e.g., a sample-specific barcode) and a binding moiety into a cell and/or cell bead include inorganic nanoparticles prepared from metals, (e.g., iron, gold, and silver), inorganic salts, and ceramics (e.g., phosphate or carbonate salts of calcium, magnesium, or silicon). The surface of a nanoparticle can be coated to facilitate binding of the molecule (e.g., a reporter oligonucleotide molecule) having a barcode (e.g., a sample-specific barcode) and a binding moiety, or the surface can be chemically modified to facilitate attachment of the molecule (e.g., a reporter oligonucleotide molecule) having a barcode (e.g., a sample-specific barcode) and a binding moiety. Magnetic nanoparticles (e.g., supermagnetic iron oxide), fullerenes (e.g., soluble carbon molecules), carbon nanotubes (e.g., cylindrical fullerenes), quantum dots and supramolecular systems can also be used.

iii. Liposomes

In some embodiments, binding of a cell feature (e.g., a molecule on and/in a cell) by a molecule (e.g., a labeling agent) having a barcode (e.g., a sample-specific barcode) and a binding moiety is facilitated by a liposome. Various types of lipids, including cationic lipids, can be used in liposome delivery. In some cases, a molecule (e.g., a reporter oligonucleotide molecule) having a barcode (e.g., a sample-specific barcode) and a binding moiety is delivered to a cell via a lipid nano-emulsion. In some embodiments, a lipid emulsion comprises a dispersion of one immiscible liquid in another stabilized by emulsifying agent. Labeling cells can comprise use of a solid lipid nanoparticle.

iv. Polymersomes

In some embodiments, binding of a cell feature (e.g., a molecule on and/in a cell) by a molecule (e.g., a labeling agent) having a barcode (e.g., a sample-specific barcode) and a binding moiety is facilitated by a polymersome. In some embodiments, a molecule (e.g., a reporter oligonucleotide molecule) having a barcode (e.g., a sample-specific barcode) and a binding moiety is contained in the polymersome, and the molecule (e.g., a nucleic acid molecule) having a barcode (e.g., a sample-specific barcode) and a binding moiety uses the polymersome to get access to analytes inside the cell. In some embodiments, a "polymersome" comprises an artificial vesicle. For example, a polymersome can be a vesicle similar to a liposome, but the membrane comprises amphiphilic synthetic block copolymers (see, e.g., Rideau et al. *Chem. Soc. Rev.,* 2018, 47, 8572-8610, the content of which is herein incorporated by reference in its entirety). In some embodiments, polymersomes comprise di-(AB) or tri-block copolymers (e.g., ABA or ABC), where A and C are a hydrophilic block and B is a hydrophobic block. In some embodiments, a polymersome comprises poly(butadiene)-b-poly(ethylene oxide), poly (ethyl ethylene)-b-poly(ethylene oxide), polystyrene-b-poly (ethylene oxide), poly(2-vinylpyridine)-b-poly(ethylene oxide), polydimethylsiloxane-b-poly(ethylene oxide), polydimethylsiloxane-g-poly(ethylene oxide), polycaprolactone-b-poly(ethylene oxide), polyisobutylene-b-poly(ethylene oxide), polystyrene-b-polyacrylic acid, polydimethylsiloxane-b-poly-2-methyl-2-oxazoline, or a combination thereof (wherein b=block and g=grafted).

v. Peptide-Based Chemical Vectors

In some embodiments, binding of a cell feature (e.g., a molecule on and/in a cell) by a molecule (e.g., a labeling agent) having a barcode (e.g., a sample-specific barcode) and a binding moiety is facilitated by a peptide-based chemical vector, e.g., a cationic peptide-based chemical vector. Cationic peptides can be rich in basic residues like lysine and/or arginine. In some embodiments, binding of a biological analyte by a molecule is facilitated by a polymer-based chemical vector. Cationic polymers, when mixed with a molecule (e.g., a reporter oligonucleotide molecule) having a barcode (e.g., a sample-specific barcode) and a binding moiety, can form nanosized complexes called polyplexes. Polymer based vectors can comprise natural proteins, peptides and/or polysaccharides. Polymer based vectors can comprise synthetic polymers. In some embodiments, a polymer-based vector comprises polyethylenimine (PEI). PEI can condense DNA into positively-charged particles, which bind to anionic cell surface residues and are brought into the cell via endocytosis. In some embodiments, a polymer-based chemical vector comprises poly(L)-lysine (PLL), poly (DL-lactic acid) (PLA), poly (DL-lactide-co-glycoside) (PLGA), polyornithine, polyarginine, histones, protamines, or a combination thereof. Polymer-based vectors can comprise a mixture of polymers, for example, PEG and PLL. Other non-limiting examples of polymers include dendrimers, chitosans, synthetic amino derivatives of dextran, and cationic acrylic polymers.

vi. Electroporation

In some embodiments, binding of a cell feature (e.g., a molecule on and/in a cell) by a molecule (e.g., a labeling agent) having a barcode (e.g., a sample-specific barcode) and a binding moiety is facilitated by electroporation. With electroporation, a biological analyte by a molecule (e.g., a reporter oligonucleotide molecule) having a barcode (e.g., a sample-specific barcode) and a binding moiety can enter a cell through one or more pores in the cellular membrane formed by applied electricity. The pore of the membrane can be reversible based on the applied field strength and pulse duration.

vii. Sonoporation

In some embodiments, binding of a cell feature (e.g., a molecule on and/in a cell) by a molecule (e.g., a labeling agent) having a barcode (e.g., a sample-specific barcode) and a binding moiety is facilitated by sonoporation. Cell membranes can be temporarily permeabilized using sound waves, allowing cellular uptake of a biological analyte by a molecule (e.g., a reporter oligonucleotide molecule) having a barcode (e.g., a sample-specific barcode) and a binding moiety.

viii. Lentiviral Vectors and Retroviral Vectors

In some embodiments, binding of a cell feature (e.g., a molecule on and/in a cell) by a molecule (e.g., a labeling agent) having a barcode (e.g., a sample-specific barcode) and a binding moiety is facilitated by vectors. For example, a vector as described herein can be an expression vector where the expression vector includes a promoter sequence operably linked to the sequence encoding the molecule (e.g., a reporter oligonucleotide molecule) having a barcode (e.g., a sample-specific barcode) and a binding moiety. Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, for example, include sufficient cis-acting elements for expression where other elements for expression can be supplied by the host mammalian cell or in an in vitro expression system. Skilled practitioners will be capable of selecting suitable vectors and mammalian cells for introducing any of spatial profiling reagents described herein.

E. Other Methods and Agents for Intracellular Introduction of a Binding Moiety

In some embodiments, binding of a cell feature (e.g., a molecule on and/in a cell) by a molecule (e.g., a labeling agent) having a barcode (e.g., a sample-specific barcode) and a binding moiety is facilitated by the use of a needle, for example for injection (e.g., microinjection), particle bombardment, photoporation, magnetofection, and/or hydroporation. For example, with particle bombardment, a molecule (e.g., a reporter oligonucleotide molecule) having a barcode (e.g., a sample-specific barcode) and a binding moiety can be coated with heavy metal particles and delivered to a cell at a high speed. In photoporation, a transient pore in a cell membrane can be generated using a laser pulse, allowing cellular uptake of a molecule (e.g., a reporter oligonucleotide molecule) having a barcode (e.g., a sample-specific barcode) and a binding moiety. In magnetofection, a molecule (e.g., a reporter oligonucleotide molecule) having a barcode (e.g., a sample-specific barcode) and a binding moiety can be coupled to a magnetic particle (e.g., magnetic nanoparticle, nanowires, etc.) and localized to a target cell via an applied magnetic field. In hydroporation, a molecule (e.g., a reporter oligonucleotide molecule) having a barcode (e.g., a sample-specific barcode) and a binding moiety can be delivered to a cell and/or cell bead via hydrodynamic pressure.

IV. Substrates

In some embodiments, a substrate herein can be any support that is insoluble in aqueous liquid and which allows for positioning of biological samples, analytes, features, and/or reagents on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of cells to the substrate. Suitable substances that can be used to coat or functionalize the substrate include, but are not limited to, lectins, poly-lysine, antibodies, and polysaccharides.

In some embodiments, a substrate functions as a support for direct or indirect attachment of cells. In addition, in some embodiments, a substrate (e.g., the same substrate or a different substrate) can be used to provide support to cells, e.g., a layer of single cells deposited and/or immobilized on the substrate. Accordingly, a “substrate” is a support that is insoluble in aqueous liquid and which allows for positioning of cells on the substrate.

A wide variety of different substrates can be used for the foregoing purposes. In general, a substrate can be any suitable support material. Exemplary substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate.

The substrate can also correspond to a flow cell. Flow cells can be formed of any of the foregoing materials, and can include channels that permit reagents, solvents, features, and molecules to pass through the cell.

Among the examples of substrate materials discussed above, polystyrene is a hydrophobic material suitable for binding negatively charged macromolecules because it normally contains few hydrophilic groups. For nucleic acids immobilized on glass slides, by increasing the hydrophobicity of the glass surface the nucleic acid immobilization can be increased. Such an enhancement can permit a relatively more densely packed formation (e.g., provide improved specificity and resolution).

In some embodiments, a substrate is coated with a surface treatment such as poly(L)-lysine. Additionally or alternatively, the substrate can be treated by silanation, e.g. with epoxy-silane, amino-silane, and/or by a treatment with polyacrylamide.

The substrate can generally have any suitable form or format. For example, the substrate can be flat, curved, e.g. convexly or concavely curved towards the area where the interaction between a biological sample, e.g. cell or a tissue sample, and the substrate takes place. In some embodiments, the substrate is a flat, e.g., planar, chip or slide. The substrate can contain one or more patterned surfaces within the substrate (e.g., channels, wells, projections, ridges, divots, etc.).

A substrate can be of any desired shape. For example, a substrate can be typically a thin, flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or cross-table). In some embodiments, where a substrate structure is flat, the substrate structure can be any appropriate type of support having a flat surface (e.g., a chip or a slide such as a microscope slide).

Substrates can optionally include various structures such as, but not limited to, projections, ridges, and channels. A substrate can be micropatterned to limit lateral diffusion (e.g., to prevent overlap of spatial barcodes). A substrate modified with such structures can be modified to allow association of analytes, features, or probes at individual sites. For example, the sites where a substrate is modified with various structures can be contiguous or non-contiguous with other sites.

In some embodiments, the surface of a substrate can be modified so that discrete sites are formed that can only have or accommodate a single feature. In some embodiments, the surface of a substrate can be modified so that features adhere to random sites.

In some embodiments, the surface of a substrate is modified to contain one or more wells, using techniques such as (but not limited to) stamping techniques, microetching techniques, and molding techniques. In some embodiments in which a substrate includes one or more wells, the substrate can be a concavity slide or cavity slide. For example, wells can be formed by one or more shallow depressions on the surface of the substrate. In some embodiments, where a substrate includes one or more wells, the wells can be formed by attaching a cassette (e.g., a cassette containing one or more chambers) to a surface of the substrate structure.

In some embodiments, the structures of a substrate can comprise wells that accommodate cells.

In some embodiments, a substrate includes one or more markings on a surface of the substrate, e.g., to provide guidance for correlating spatial information with the characterization of the cells and/or analytes of interest in the cells. For example, a substrate can be marked with a grid of lines (e.g., to allow the size of objects seen under magnification to be easily estimated and/or to provide reference areas for counting objects). In some embodiments, fiducial markers can be included on the substrate. Such markings can be made using techniques including, but not limited to, printing, sand-blasting, and depositing on the surface.

In some embodiments where the substrate is modified to contain one or more structures, including but not limited to wells, projections, ridges, or markings, the structures can include physically altered sites. For example, a substrate modified with various structures can include physical properties, including, but not limited to, physical configurations, magnetic or compressive forces, chemically functionalized sites, chemically altered sites, and/or electrostatically altered sites.

In some embodiments where the substrate is modified to contain various structures, including but not limited to wells, projections, ridges, or markings, the structures are applied in a pattern. Alternatively, the structures can be randomly distributed.

In some embodiments, a substrate is treated in order to minimize or reduce non-specific analyte hybridization within or between features. For example, treatment can include coating the substrate with a hydrogel, film, and/or membrane that creates a physical barrier to non-specific hybridization. Any suitable hydrogel can be used. For example, hydrogel matrices prepared according to the methods set forth in U.S. Pat. Nos. 6,391,937, 9,512,422, and 9,889,422, and U.S. Patent Application Publication Nos. U.S. 2017/0253918 and U.S. 2018/0052081, can be used. The entire contents of each of the foregoing documents are incorporated herein by reference.

Treatment can include adding a functional group that is reactive or capable of being activated such that it becomes reactive after receiving a stimulus (e.g., photoreactive). Treatment can include treating with polymers having one or more physical properties (e.g., mechanical, electrical, magnetic, and/or thermal) that minimize non-specific binding (e.g., that activate a substrate at certain locations to allow analyte hybridization at those locations).

The substrate (e.g., a feature on an array) can include tens to hundreds of thousands or millions of individual oligonucleotide molecules (e.g., at least about 10,000, 50,000, 100,000, 500,000, 1,000,000, 10,000,000, 100,000,000, 1,000,000,000, or 10,000,000,000 oligonucleotide molecules).

In some embodiments, the surface of the substrate is coated with a cell-permissive coating to allow adherence of live cells. In some embodiments, a cell-permissive coating is a coating that allows or helps cells to maintain cell viability (e.g., remain viable) on the substrate. For example, a cell-permissive coating can enhance cell attachment, cell growth, and/or cell differentiation, e.g., a cell-permissive coating can provide nutrients to the live cells. A cell-permissive coating can include a biological material and/or a synthetic material. Non-limiting examples of a cell-permissive coating include coatings that feature one or more extracellular matrix (ECM) components (e.g., proteoglycans and fibrous proteins such as collagen, elastin, fibronectin and laminin), poly-lysine, poly (L)-ornithine, and/or a biocompatible silicone (e.g., CYTOSOFT®). For example, a cell-permissive coating that includes one or more extracellular matrix components can include collagen Type I, collagen Type II, collagen Type IV, elastin, fibronectin, laminin, and/or vitronectin. In some embodiments, the cell-permissive coating includes a solubilized basement membrane preparation extracted from the Engelbreth-Holm-Swarm (EHS) mouse sarcoma (e.g., MATRIGEL®). In some embodiments, the cell-permissive coating includes collagen. A cell-permissive coating can be used to culture adherent cells on a spatially-barcoded array, or to maintain cell viability of sample while in contact with a spatially-barcoded array.

Substrates for In Situ Detection of Analytes in Cells

In some embodiments, a plurality of labeled cells from different samples are deposited and/or immobilized on a substrate for one or more in situ assays, e.g., using one or more nucleic acid probes for detecting analytes in the labeled cells. The one or more nucleic acid probes may directly or indirectly hybridize to a target nucleic acid or a complement or an amplification product thereof in a labeled cell.

A wide variety of different substrates can be used for the in situ assay, as long as the substrate is compatible with the sample and sample processing, the in situ reagents and reactions, and in situ signal detection (e.g., optical imaging such as fluorescence microscopy). A substrate can be any suitable support material and is generally transparent. For example, a glass slide such as a cover slip may be used. The substrate can include, but are not limited to, glass, modified and/or functionalized glass, hydrogels, films, membranes, plastics, nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate. The substrate can also correspond to a flow cell.

In some embodiments, the substrate is between about 0.01 mm and about 5 mm, e.g., between about 0.05 mm and about 3 mm, between about 0.1 mm and about 2.5 mm, between about 0.2 mm and about 2 mm, between about 0.5 mm and about 1.5 mm, or about 1 mm in thickness. In some embodiments, the substrate is or is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mm in thickness, or of a thickness in between any of the aforementioned values.

V. In Situ Detection

In some embodiments, provided herein are methods comprising in situ assays using microscopy as a readout, e.g., nucleic acid sequencing, hybridization, or other detection or determination methods involving an optical readout. In some aspects, detection or determination of a sequence of one, two, three, four, five, or more nucleotides of nucleic acid analytes is performed in situ in a cell on a substrate. In some embodiments, the assay comprises detecting the presence or absence of an amplification product (e.g., RCA product). In some embodiments, the present disclosure provides methods for high-throughput profiling of a large number of targets and analytes in situ, such as transcripts and/or DNA loci, e.g., for detecting and/or quantifying nucleic acids and/or proteins in cells, tissues, organs or organisms.

In some aspects, provided herein is a method comprising analyzing biological targets based on in situ hybridization of probes comprising nucleic acid sequences. In some embodiments, the method comprises sequential hybridization of detectably-labeled oligonucleotides to barcoded probes that directly or indirectly bind to biological targets in a sample. In some embodiments, a detectably-labeled oligonucleotide directly binds to one or more barcoded probes. In some embodiments, a detectably-labeled oligonucleotide indirectly binds to one or more barcoded probes, e.g., via one or more bridging nucleic acid molecules.

In some aspects, an in situ hybridization based assay is used to localize and analyze nucleic acid sequences (e.g., a DNA or RNA molecule comprising one or more specific sequences of interest) within a native biological sample, e.g., or a single cell. In some embodiments, the in situ assay is used to analyze the presence, absence, an amount or level of mRNA transcripts (e.g., a transcriptome or a subset thereof, or mRNA molecules of interest) in a biological sample, while preserving spatial context. In some embodiments, the present disclosure provides compositions and methods for in situ hybridization using directly or indirectly labeled molecules, e.g., complementary DNA or RNA or modified nucleic acids, as probes that bind or hybridize to a target nucleic acids within a biological sample of interest.

Nucleic acid probes, in some examples, may be labeled with radioisotopes, epitopes, hapten, biotin, or fluorophores, to enable detection of the location of specific nucleic acid sequences on chromosomes or in cells. In some embodiments, probes are locus specific (e.g., gene specific) and bind or couple to specific regions of a chromosome. In alternative embodiments, probes are alphoid or centromeric repeat probes that bind or couple to repetitive sequences within each chromosome. Probes may also be whole chromosome probes (e.g., multiple smaller probes) that bind or couple to sequences along an entire chromosome.

In some embodiments, provided herein is a method comprising DNA in situ hybridization to measure and localize DNA. In some embodiments, provided herein is a method comprising RNA in situ hybridization to measure and localize RNAs (e.g., mRNAs, lncRNAs, and miRNAs) within a biological sample (e.g., a dissociated cell sample). In some embodiments, RNA in situ hybridization involves single-molecule RNA fluorescence in situ hybridization (FISH). In some embodiments, fluorescently labeled nucleic acid probes are hybridized to pre-determined RNA targets, to visualize gene expression in a biological sample. In some embodiments, a FISH method comprises using a single nucleic acid probe specific to each target, e.g., single-molecule FISH (smFISH). The use of smFISH may produce a fluorescence signal that allows for quantitative measurement of RNA transcripts. In some embodiments, smFISH comprises a set of nucleic acid probes, about 50 base pairs in length, wherein each probe is coupled to a set fluorophores. For example, the set of nucleic acid probes may comprise five probes, wherein each probe coupled to five fluorophores. In some embodiments, said nucleic acid probes are instead each coupled to one fluorophore. For example, a smFISH protocol may use a set of about 40 nucleic acid probes, about 20 base pairs in length, each coupled to a single fluorophore. In some embodiments, the length of the nucleic acid probes varies, comprising 10 to 100 base pairs, such as 30 to 60 base pairs. Alternatively, a plurality of nucleic acid probes targeting different regions of the same RNA transcript may be used. It will be appreciated by those skilled in the art that the type of nucleic acid probes, the number of nucleic acid probes, the number of fluorophores coupled to said probes, and the length of said probes, may be varied to fit the specifications of the individual assay.

In further embodiments smFISH is applied to a multiplexed workflow, wherein consecutive/sequential hybridizations are used (e.g., as in seqFISH or seqFISH+) to impart a temporal barcode on target transcripts. Sequential rounds of fluorescence in situ hybridization may be accompanied by imaging and probe stripping, detecting individual transcripts (e.g., RNA transcripts) within a biological sample of interest (e.g., a dissociated cell sample or extracted RNA). In some embodiments, each round of hybridization comprises a pre-defined set of probes (e.g., between about 10 and about 50 probes such as 24 to 32 probes) that target unique RNA transcripts. In some examples, the pre-defined set of probes is multicolored. Optionally, multiple nucleic acid probes are attached onto the sample, wherein each probe comprises an initiation sequence for amplification, allowing for decreased autofluorescence (e.g., as in single-molecule hybridization chain reaction (smHCR)). In some embodiments, a multiplexed smFISH method described herein may multiplex from 10s to over 10,000 mRNAs, optionally accompanied by imaging, to efficiently and accurately profile the entire transcriptome. In situ hybridization methods may further comprise using two probes to bind target transcripts (e.g., RNA transcripts), that serve as binding targets for amplification primers. In some embodiments, this process results in signal amplification (e.g., as in RNAscope). In some embodiments, in situ hybridization methods may employ metal tags instead of fluorophores (e.g., imaging mass cytometry). Metal-conjugated antibodies may couple to the metal tags hybridized to transcripts on a biological sample. In some embodiments, mass-cytometry may be used to quantify metal abundances, allowing the concurrent evaluation of RNA and protein within a biological sample.

In some embodiments, a method described herein comprises a multiplexed FISH protocol that is error-robust (e.g., MERFISH). In some embodiments, said protocol comprises non-readout nucleic acid probes (e.g., primary probes) comprising a binding region (e.g., a region that binds to a target such as RNA transcripts) coupled to one or more flanking regions. In some embodiments, each non-readout nucleic acid probe is coupled to two flanking regions. The non-readout nucleic acid probes may hybridize to a transcript (e.g., RNA transcript) within a biological sample (e.g., dissociated cell sample or a single cell), such that florescent readout nucleic acid probes may subsequently serially hybridize to the flanking region(s) of the non-readout nucleic acid probes. In some embodiments, each round of hybridization comprises successive imaging and probe stripping to quench signals from readout nucleic acid probes from previous rounds. RNAs may be imaged by FISH, and errors accumulated during multiple imaging rounds (e.g., imperfect hybridizations) are detected and/or corrected. In some embodiments, expansion microscopy is employed to increase the number of detected RNA targets without signal overlap. In similar embodiments, non-readout nucleic acid probes are cross-linked to target transcripts prior to imaging. Cross-linking may be performed by any suitable methods. In preferred embodiments, cross-linking is performed using hydrogel embedding. Following said cross-linking steps, barcoding may be performed, comprising sequential hybridizations using readout probes coupled to pre-determined colors to generate unique barcodes (e.g., generating pseudocolors from consecutive hybridizations). In some embodiments, one or more barcodes of a probe are targeted by detectably labeled detection oligonucleotides, such as fluorescently labeled oligonucleotides.

Similar strategies of in situ hybridization using variations of FISH techniques may be adopted by methods described herein. In some embodiments, a method comprises non-barcoding multiplexed FISH protocols (e.g., ouroboros sm-FISH (osmFISH)). Non-barcoding methods may be limited to detecting a specific number of targets, defined by the number of hybridization rounds performed. In some embodiments, imaging is performed following each hybridization round, wherein the probe is stripped after imaging, allowing for subsequent hybridization and imaging rounds.

Additional embodiments of the present disclosure may include using in situ hybridization protocols that do not rely on probe capture of transcripts from pre-defined locations. In some embodiments, optics-free spatial mapping of transcripts in a biological sample may be used (e.g., a chemically encoded microscopy system). In some embodiments, transcripts are first tagged in situ with unique nucleotide tags (e.g., unique molecular identifiers). This first reaction may be followed by a second in situ amplification reaction, labeled by a new set of unique nucleotide tags (e.g., unique event identifiers). In some embodiments, RNA or DNA sequencing may be used to identify each molecular chain sequence (e.g., concatemers). In further embodiments, an algorithm may be used to evaluate the proximities of the sequences and produce images of the target transcripts, in combination with sequence information.

In some embodiments, provided herein is a method comprising linking sequencing information and spatial information of targets within endogenous environments. For example, analysis of nucleic acid sequences may be performed directly on DNA or RNA within an intact biological sample of interest, e.g., by in situ detection of nucleic acid sequences involving sequential hybridization of detectable probes. In some embodiments, the present disclosure allows for the simultaneous identification and quantification of a plurality of targets, such as 100s, 1000s, or more of transcripts (e.g., mRNA transcripts), in addition to spatial resolution of said transcripts. In some aspects, the spatial resolution of transcripts may be subcellular. Optionally, the spatial resolution may be increased using signal amplification strategies described herein.

In some embodiments, fluorescent dyes are used to target nucleic acid bases, and circularizable probes or probe sets (e.g., padlock probe) are used to target RNAs of interest in situ. In some embodiments, mRNAs are reverse transcribed into cDNAs, and circularizable probes or probe sets (e.g., padlock probe) are able to bind or couple to cDNAs. In some embodiments, circularizable probes or probe sets (e.g., padlock probe) comprise oligonucleotides with ends that are complementary to a target sequence (e.g., target cDNA transcripts). Upon hybridization of padlock probes to the target sequence, enzymes may be used to ligate the ends of the padlock probes, and catalyze the formation of circularized DNA.

In some embodiments, the ends of the circularizable probes or probe sets (e.g., padlock probe) are in close proximity upon hybridization to the target RNA or cDNA, to allow ligation and circularization of the padlock probe. The padlock probes may additionally comprise one or more barcode sequences. In alternative embodiments, there may be a gap between the ends of the padlock probes upon hybridization to the target RNA or cDNA, that must be filled with nucleic acids (e.g., by DNA polymerization), prior to ligation of the ends of the padlock probes and circularization. In some embodiments, the gap between two ends of the padlock probes is of variable length, e.g., up to four base pairs, and can allow reading out the actual RNA or cDNA sequence. In some embodiments, the DNA polymerase has strand displacement activity. In some embodiments, the DNA polymerase may instead not have strand displacement activity, such as the polymerase used in barcode in situ target sequencing (BaristaSeq) which provides read-length of up to 15 bases using a gap-filling padlock probe approach. See, e.g., Chen et al., Nucleic Acids Res. 2018, 46, e22, the content of which is herein incorporated by reference in its entirety.

A method described herein may comprise DNA circularization and amplification (e.g., rolling circle amplification), at the location of circularizable probes or probe sets (e.g., padlock probe). In some embodiments, amplification results in multiple repeats of padlock probe sequences. Sequencing and/or decoding of the amplified padlock probes may be performed using sequencing by ligation. In alternative methods, sequencing by hybridization or sequencing by synthesis is used. In some embodiments, amplicons are stabilized by crossing-linking described herein, during the sequencing process. In some embodiments, the methods presented in this disclosure, including the in situ detection step, may be automated on a microfluidic platform.

Additional approaches to in situ detection will be appreciated by those skilled in the art. For example, in some embodiments, barcoded padlocks probes may not be reverse transcribed. Instead, a second primer binds (e.g., ligates) directly to an RNA sequence adjacent to the circularizable probe or probe set (e.g., padlock probe). In some embodiments, amplification (e.g., rolling circle amplification) is performed, wherein the amplification product becomes embedded within a hydrogel by any suitable method (e.g., hydrogel-tissue chemistry), which is then cleaned of unbound proteins and lipids. Embedded amplification products may, for example, be sequenced using variations of the sequencing by ligation approach, to determine the barcode sequence of each padlock probe. In some embodiments, the combinations of chemistry and sequencing described herein may be used to analyze spatial orientation of target transcripts in 3D.

In some embodiments, in situ detection methods described in the present disclosure may be untargeted. In some embodiments, untargeted in situ detection may comprise genome/transcriptome-wide profiling of gene expression within a biological sample of interest, e.g., as in fluorescent in situ RNA sequencing (FISSEQ). In some embodiments, RNA species are converted into cross-linked cDNA amplicons (e.g., cDNA cross-linked to the cellular protein matrix of the sample). In some examples, cDNA synthesis is performed using modified amine bases to promote the cross-linking process. The synthesis of cross-linked cDNA amplicons may be followed by amplification (e.g., rolling circle amplification) as described elsewhere herein. In some embodiments, sequencing by ligation may be used to sequence the amplification products. In some embodiments, the sequencing step includes partition sequencing to selectively sequence of subsets of amplification products. In some embodiments, the strategies described herein allow for the detection of RNA, DNA, and/or proteins, in tandem. In some embodiments, in situ detection may be combined with ex situ sequencing, e.g., as in in situ transcriptome accessibility sequencing (INSTA-Seq).

In some embodiments, in situ detection involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (nucleotide sequence) of the incorporated nucleotides or labeled primer extension products can be determined, and consequently, the nucleotide sequence of the corresponding template nucleic acid. Aspects of in situ detection are described, for example, in Mitra et al., (2003) Anal. Biochem. 320, 55-65, and Lee et al., (2014) Science, 343(6177), 1360-1363. In addition, examples of methods and systems for performing in situ detection are described in US 2021/0340618, US 2019/0032121, US 2019/0330617, US 2019/0194709, U.S. Pat. Nos. 10,138,509, 10,179,932, Wang et al., (2018) Science, 361(6499) 5691), and Moffitt, (2016) Methods in Enzymology, 572, 1-49, all of which are incorporated herein by reference.

i. Probes and Probe Hybridization

In some aspects, the methods disclosed herein involve the use of one or more probes or probe sets that hybridize to an analyte, such as an RNA molecule.

Exemplary probes or probe sets may be based on a circularizable probe or probe set (e.g., padlock probe), a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set, and circularizable DNA probes bound to RNA targets (e.g., RNA-templated ligation probes). The specific probe or probe set design can vary.

In some embodiments, a primary probe (e.g., a DNA probe that directly binds to an RNA target) is amplified through rolling circle amplification, e.g., using a circular probe or a circularized probe from padlock ligation as a template. In some embodiments, the primary probes, such as a padlock probe or a probe set that comprises a padlock probe, contain one or more barcodes. In some embodiments, one or more barcodes are indicative of a sequence in the target nucleic acid, such as a single nucleotide of interest (e.g., SNPs or point mutations), a dinucleotide sequence, a short sequence of about 5 nucleotides in length, or a sequence of any suitable length.

In some embodiments, provided herein is a probe or probe set capable of DNA-templated ligation, such as from a cDNA molecule. See, e.g., U.S. Pat. No. 8,551,710, the content of which is herein incorporated by reference in its entirety. In some embodiments, provided herein is a DNA probe or probe set comprising ribonucleotides in particular position(s) capable of hybridizing to target nucleic acids (e.g., mRNA molecule) and being ligated in a target-dependent manner. See, e.g., US 2020/0224244, the content of which is herein incorporated by reference in its entirety. In some embodiments, the probe set is a SNAIL probe set. See, e.g., U.S. Pat. Pub. 2019/0055594, the content of which is herein incorporated by reference in its entirety. In some embodiments, provided herein is a probe or probe set capable of proximity ligation, for instance a proximity ligation assay for RNA (e.g., PLAYR) probe set. See, e.g., U.S. Pat. Pub. 20160108458, the content of which is herein incorporated by reference in its entirety.

In some embodiments, a circular probe can be indirectly hybridized to the target nucleic acid. In some embodiments, the circular construct is formed from a probe set capable of proximity ligation, for instance a proximity ligation in situ hybridization (PLISH) probe set. See, e.g., US 2020/0224243, the content of which is herein incorporated by reference in its entirety.

An exemplary probe set and hybridization complex includes a circularizable probe or probe set (e.g., padlock probe) or circular probe that directly hybridizes to an RNA transcript. A splint primer can be used to facilitate DNA-templated padlock ligation. The padlock or circular probe may comprise a targeting (e.g., target-hybridizing) sequence and one or more barcode regions, such as primary barcode sequences BC1 and BC2. After probe hybridization and/or any circularization steps to provide a circular probe, in some embodiments the circular probe is amplified, e.g., in a RCA reaction, to generate an amplified molecule comprising the primary barcodes (e.g., BC1) or complementary sequences thereof. In some embodiments, after amplification, the method further comprises detecting the amplification product using a detectably labeled oligonucleotide (such as a fluorescently-labeled detection oligonucleotide) that is capable of hybridizing to one or more of the barcode sequences (e.g., BC1 or BC2) or complementary sequences thereof.

Another exemplary probe set and hybridization complex includes a circularizable probe or probe set (e.g., padlock probe) or circular probe that directly hybridizes to an RNA transcript. A splint primer can be used to facilitate DNA-templated padlock ligation. The padlock or circular probe may comprise a targeting (e.g., target-hybridizing) sequence and one or more barcode regions, such as primary barcode sequences BC1 and BC2. After probe hybridization and/or any circularization steps to provide a circular probe, in some embodiments the circular probe is amplified, e.g., in a RCA reaction, to generate an amplified molecule comprising the primary barcodes (e.g., BC1) or complementary sequences thereof. In some embodiments, after amplification, the method further comprises using a detectable probe (e.g., a secondary probe) comprising (1) a barcode-binding region that hybridizes to the primary barcode region of the targeting probe directly or indirectly, and (2) two or more detection barcode regions (e.g., SBC11 and SBC12) that each hybridizes to a detectably labeled oligonucleotide, Secondary Probe 1 and Secondary Probe 2. Secondary Probe 1 comprises a barcode-binding region that hybridizes to BC1 of the targeting probe directly or indirectly, and four detection barcode regions, Secondary Barcodes (SBC) 11, SBC12, SBC13, and SBC14. Each of SBC11, SBC12, SBC13, and SBC14 is capable of hybridizing to a detectably labeled oligonucleotide, such as a fluorescently labeled detection oligo. Likewise, Secondary Probe 2 comprises a barcode-binding region that hybridizes to BC2 of the targeting probe directly or indirectly, and four detection barcode regions, Secondary Barcodes (SBC) 21, SBC22, SBC23, and SBC24, each of which is capable of hybridizing to a detectably labeled oligonucleotide, such as a fluorescently labeled detection oligo. In some embodiments, two or more of the secondary barcodes are different from each other. For example, all of the secondary barcodes of the secondary probes that bind to the same primary probe may be different, e.g., each secondary barcode may specifically hybridize to a detection oligo and be uniquely identified by the detection oligo sequence.

In any of the embodiments disclosed herein, is a multiplexed assay where multiple target nucleic acids (e.g., genes or RNA transcripts) are probed with multiple primary probes (e.g., padlock primary probes), and optionally multiple secondary probes hybridizing to the primary barcodes (or complementary sequences thereof) are all hybridized at once, followed by sequential secondary barcode detection and decoding of the signals. In any of the embodiments disclosed herein, the multiplexed assay further comprises hybridizing labeling agents with probes and/or detectably labeled probes, followed by barcode detection and decoding of the signals.

ii. Ligation

In some embodiments, the provided methods involve ligating one or more polynucleotides that are part of a hybridization complex that comprises a reporter oligonucleotide and/or a target nucleic acid for in situ analysis. In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, e.g., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, circularizable probe or probe set (e.g., padlock probe), or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

iii. Amplification

In some embodiments, the methods of the present disclosure comprise the step of amplifying one or more polynucleotides, for instance the circularizable probe or probe set (e.g., padlock probe) or a circular probe formed from the padlock probe. In some embodiments, the amplifying is achieved by performing rolling circle amplification (RCA). In other embodiments, a primer that hybridizes to the padlock probe is added and used as such for amplification.

In some embodiments, a removing step is performed to remove molecules that are not specifically hybridized to the target nucleic acid, the reporter oligonucleotide, and/or the circular probe. In some embodiments, the removing step is performed to remove unligated probes. In some embodiments, the removing step is performed after ligation and prior to amplification.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (e.g., amplicon) containing multiple copies of the cDNA. Techniques for rolling circle amplification (RCA) that can be used include linear RCA, a branched RCA, a dendritic RCA, or any combination thereof. See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29:el 18, 2001; Dean et al. Genome Res. 11:1095-1099, 2001; Schweitzer et al, Nature Biotech. 20:359-365, 2002; U.S. Pat. Nos. 6,054,274, 6,291,187, 6,323,009, 6,344,329 and 6,368,801, all of which are herein incorporated by reference in their entireties. Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix.

Exemplary modification and polymer matrix that can be employed in accordance with the provided embodiments comprise those described in, for example, WO 2014/163886, U.S. Ser. No. 10/138,509, WO2014/025392, U.S. Ser. No. 10/545,075, WO 2017/079406, US 2016/0024555, US 2018/0251833, US2019/0276881, US2020/0071751, WO2020/076976, WO2020/076979, and WO2020/096687, which are incorporated herein by reference in their entirety. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

iv. Detection and Analysis

In some embodiments, a method disclosed herein comprises detecting the reporter oligonucleotide and/or one or more target nucleic acids in the dissociated cells on a substrate using a plurality of primary probes configured to hybridize to the reporter oligonucleotide and/or the one or more target nucleic acids, wherein each primary probe comprises (i) a target-hybridizing region configured to hybridize to a different target region in the corresponding target nucleic acid, and (ii) a barcode region. In some embodiments, the dissociated cells on the substrate are contacted with a plurality of detectable probes, wherein each detectable probe is configured to hybridize to (i) a barcode sequence in the barcode regions of the plurality of primary probes, or (ii) a complement of the barcode sequence. In some embodiments, the method further comprises detecting a signal associated with the plurality of detectable probes or absence thereof at one or more locations in the dissociated cells. In some embodiments, the dissociated cells on the substrate are contacted with a subsequent plurality of detectable probes, wherein each detectable probe in the subsequent plurality is configured to hybridize to (i) a subsequent barcode sequence in the barcode regions of the plurality of primary probes, or (ii) a complement of the subsequent barcode sequence. In some embodiments, the method further comprises detecting a subsequent signal associated with the subsequent plurality of detectable probes or absence thereof at the one or more locations in the dissociated cells. In some embodiments, the method further comprises generating a signal code sequence comprising signal codes corresponding to the signal or absence thereof and the subsequent signal or absence thereof, respectively, at the one or more locations, wherein the signal code sequence corresponds to the reporter oligonucleotide or one of the one or more target nucleic acids, thereby identifying the reporter oligonucleotide or the target nucleic acid at the one or more locations in the dissociated cells. As such, detection of the target nucleic acid in situ in a particular dissociated cell can be correlated with the sample origin of the dissociated cell, since the reporter oligonucleotide detected in situ in the particular dissociated cell identifies the sample from which the particular dissociated cell is derived from. In some embodiments, the method disclosed herein comprises comparing signals detected in a deposited labeled cell with signal(s) detected in one or more other cells in the population. In some embodiments, the dissociated cells deposited on the substrate are imaged prior to, during, and/or after detecting the signals associated with the plurality of probes or products thereof. In some embodiments, the deposited labeled cell is live or fixed prior to detecting the signals associated with the plurality of probes or products thereof.

In some embodiments, in situ detection of the reporter oligonucleotide and/or one or more target nucleic acids in the dissociated cells is performed using sequential hybridization of detectable probes to the plurality of primary probes, and using signals associated with the sequentially hybridized detectable probes to decode signal code sequences each assigned to the reporter oligonucleotide or one of the one or more target nucleic acids in the dissociated cells. Each primary probe can be selected from the group consisting of: a probe comprising a 3' or 5' overhang (e.g., L-shaped probes), optionally wherein the 3' or 5' overhang comprises one or more barcode sequences; a probe comprising a 3' overhang and a 5' overhang (e.g., U-shaped probes), optionally wherein the 3' overhang and the 5' overhang each independently comprises one or more barcode sequences; a circular probe; a circularizable probe or probe set; a probe or probe set comprising a split hybridization region configured to hybridize to a splint, optionally wherein the split hybridization region comprises one or more barcode sequences; and a combination thereof.

In some embodiments, the present disclosure relates to the detection of nucleic acids sequences in situ using probe hybridization and generation of amplified signals associated with the probes, wherein background signal is reduced and sensitivity is increased.

Exemplary in situ detection methods include targeted deposition of detectable reactive molecules around the site of probe hybridization, targeted assembly of branched structures (e.g., bDNA or branched assay using locked nucleic acid (LNA)), programmed in situ growth of concatemers by enzymatic rolling circle amplification (RCA) (e.g., as described in US 2019/0055594 incorporated herein by reference), hybridization chain reaction, assembly of topologically catenated DNA structures using serial rounds of chemical ligation (clampFISH), signal amplification via hairpin-mediated concatemerization (e.g., as described in US 2020/0362398 incorporated herein by reference), e.g., primer exchange reactions such as signal amplification by exchange reaction (SABER) or SABER with DNA-Exchange (Exchange-SABER). In some embodiments, a non-enzymatic signal amplification method may be used.

In some embodiments, a method disclosed herein comprises generating rolling circle amplification (RCA) products associated with the reporter oligonucleotide and/or one or more target nucleic acids in the dissociated cells on a substrate. In some embodiments, the RCA products are detected in situ in the dissociated cells on the substrate, thereby detecting the reporter oligonucleotide and/or the one or more target nucleic acids. In some embodiments, each of the RCA products comprises multiple complementary copies of a barcode sequence, wherein the barcode sequence is associated with a reporter oligonucleotide or a target nucleic acid in the dissociated cells and is assigned a signal code sequence. In some embodiments, the method comprises contacting the dissociated cells with a first detectable probe comprising (i) a recognition sequence complementary to a sequence in the complementary copies of the barcode sequence and (ii) a reporter. In some embodiments, the method comprises detecting a first signal or absence thereof from the reporter of the first detectable probe hybridized to its corresponding sequence of the complementary copies of the barcode sequence in the RCA product, wherein the first signal or absence thereof corresponds to a first signal code in the signal code sequence. In some embodiments, the method comprises contacting the dissociated cells with a subsequent detectable probe comprising (i) a recognition sequence complementary to a sequence of the complementary copies of the barcode sequence and (ii) a reporter. In some embodiments, the method comprises detecting a subsequent signal or absence thereof from the reporter of the subsequent detectable probe hybridized to its corresponding sequence of the complementary copies of the barcode sequence in the RCA product, wherein the subsequent signal or absence thereof corresponds to a subsequent signal code in the signal code sequence. In some embodiments, the signal code sequence comprising the first signal code and the subsequent signal code is determined at a location in the dissociated cells, thereby decoding the barcode sequence and identifying the target analyte at the location in the dissociated cells. As such, detection of the target analyte (e.g., a target nucleic acid) in situ in a particular dissociated cell can be correlated with the sample origin of the dissociated cell, since the reporter oligonucleotide detected in situ in the particular dissociated cell identifies the sample from which the particular dissociated cell is derived from.

In some embodiments, the barcode sequence comprises one or more barcode positions each comprising one or more barcode subunits. In some embodiments, a barcode position in the barcode sequence partially overlaps an adjacent barcode position in the barcode sequence. In some embodiments, the first detectable probe and the subsequent detectable probe are in a set of detectable probes each comprising the same recognition sequence and a reporter. In some embodiments, the reporter of each detectable probe in the set comprises a binding site for a reporter probe comprising a detectable moiety. In some embodiments, the reporter probe binding site of the first detectable probe and the reporter probe binding site of the subsequent detectable probe are the same. In some embodiments, the reporter probe binding site of the first detectable probe and the reporter probe binding site of the subsequent detectable probe are different. In some embodiments, the detectable moiety is a fluorophore and the signal code sequence is a fluorophore sequence uniquely assigned to the target analyte. In some embodiments, the detectable probes in the set are contacted with the dissociated cells sequentially in a pre-determined sequence which corresponds to the signal code sequence assigned to the barcode sequence. In some embodiments, the detectable probes in the set are contacted with the dissociated cells to determine signal codes in the signal code sequence until sufficient signal codes have been determined to decode the barcode sequence, thereby identifying the target analyte.

The detectable reactive molecules may comprise tyramide, such as used in tyramide signal amplification (TSA) or multiplexed catalyzed reporter deposition (CARD)-FISH. In some embodiments, the detectable reactive molecule may be releasable and/or cleavable from a detectable label such as a fluorophore. In some embodiments, a method disclosed herein comprises multiplexed analysis of a biological sample comprising consecutive cycles of probe hybridization, fluorescence imaging, and signal removal, where the signal removal comprises removing the fluorophore from a fluorophore-labeled reactive molecule (e.g., tyramide). Exemplary detectable reactive reagents and methods are described in U.S. Pat. No. 6,828,109, US 2019/0376956, WO 2019/236841, WO 2020/102094, US 20220026433, WO 2020/163397, US 20220128565, and WO 2021/067475, US 20210222234, all of which are incorporated herein by reference in their entireties.

In some embodiments, hybridization chain reaction (HCR) can be used for signal detection in situ. HCR is an enzyme-free nucleic acid amplification based on a triggered chain of hybridization of nucleic acid molecules starting from HCR monomers, which hybridize to one another to form a nicked nucleic acid polymer. This polymer is the product of the HCR reaction which is ultimately detected in order to indicate the presence of the target analyte. HCR is described in detail in Dirks and Pierce, 2004, PNAS, 101 (43), 15275-15278 and in U.S. Pat. Nos. 7,632,641 and 7,721,721 (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401). HCR monomers typically comprise a hairpin, or other metastable nucleic acid structure. In the simplest form of HCR, two different types of stable hairpin monomer, referred to here as first and second HCR monomers, undergo a chain reaction of hybridization events to form a long nicked double-stranded DNA molecule when an "initiator" nucleic acid molecule is introduced. The HCR monomers have a hairpin structure comprising a double stranded stem region, a loop region connecting the two strands of the stem region, and a single stranded region at one end of the double stranded stem region. The single stranded region which is exposed (and which is thus available for hybridization to another molecule, e.g. initiator or other HCR monomer) when the monomers are in the hairpin structure may be known as the "toehold region" (or "input domain"). The first HCR monomers each further comprise a sequence which is complementary to a sequence in the exposed toehold region of the second HCR monomers. This sequence of complementarity in the first HCR monomers may be known as the "interacting region" (or "output domain") Similarly, the second HCR monomers each comprise an interacting region (output domain), e.g. a sequence which is complementary to the exposed toehold region (input domain) of the first HCR monomers. In the absence of the HCR initiator, these interacting regions are protected by the secondary structure (e.g. they are not exposed), and thus the hairpin monomers are stable or kinetically trapped (also referred to as "metastable"), and remain as monomers (e.g. preventing the system from rapidly equilibrating), because the first and second sets of HCR monomers cannot hybridize to each other. However, once the initiator is introduced, it is able to hybridize to the exposed toehold region of a first HCR monomer, and invade it, causing it to open up. This exposes the interacting region of the first HCR monomer (e.g. the sequence of complementarity to the toehold region of the second HCR monomers), allowing it to hybridize to and invade a second HCR monomer at the toehold region. This hybridization and invasion in turn opens up the second HCR monomer, exposing its interacting region (which is complementary to the toehold region of the first HCR monomers), and allowing it to hybridize to and invade another first HCR monomer. The reaction continues in this manner until all of the HCR monomers are exhausted (e.g. all of the HCR monomers are incorporated into a polymeric chain). Ultimately, this chain reaction leads to the formation of a nicked chain of alternating units of the first and second monomer species. The presence of the HCR initiator is thus required in order to trigger the HCR reaction by hybridization to and invasion of a first HCR monomer. The first and second HCR monomers are designed to hybridize to one another are thus may be defined as cognate to one another. They are also cognate to a given HCR initiator sequence. HCR monomers which interact with one another (hybridize) may be described as a set of HCR monomers or an HCR monomer, or hairpin, system.

An HCR reaction could be carried out with more than two species or types of HCR monomers. For example, a system involving three HCR monomers could be used. In such a system, each first HCR monomer may comprise an interacting region which binds to the toehold region of a second HCR monomer; each second HCR may comprise an interacting region which binds to the toehold region of a third HCR monomer; and each third HCR monomer may comprise an interacting region which binds to the toehold region of a first HCR monomer. The HCR polymerization reaction would then proceed as described above, except that the resulting product would be a polymer having a repeating unit of first, second and third monomers consecutively. Corresponding systems with larger numbers of sets of HCR monomers could readily be conceived.

In some embodiments, similar to HCR reactions that use hairpin monomers, linear oligo hybridization chain reaction (LO-HCR) can be used for signal detection in situ. In some embodiments, provided herein is a method of detecting an analyte in a sample comprising: (i) performing a linear oligo hybridization chain reaction (LO-HCR), wherein an initiator is contacted with a plurality of LO-HCR monomers of at least a first and a second species to generate a polymeric LO-HCR product hybridized to a target nucleic acid molecule, wherein the first species comprises a first hybridization region complementary to the initiator and a second hybridization region complementary to the second species, wherein the first species and the second species are linear, single-stranded nucleic acid molecules; wherein the initiator is provided in one or more parts, and hybridizes directly or indirectly to or is comprised in the target nucleic acid molecule; and (ii) detecting the polymeric product, thereby detecting the analyte. In some embodiments, the first species and/or the second species may not comprise a hairpin structure. In some embodiments, the plurality of LO-HCR monomers may not comprise a metastable secondary structure. In some embodiments, the LO-HCR polymer may not comprise a branched structure. In some embodiments, performing the linear oligo hybridization chain reaction comprises contacting the target nucleic acid molecule with the initiator to provide the initiator hybridized to the target nucleic acid molecule. In any of the embodiments herein, the target nucleic acid molecule and/or the analyte can be an RCA product.

In some embodiments, detection of nucleic acids sequences in situ includes combination of RCA with an assembly for branched signal amplification. In some embodiments, the assembly complex comprises an amplifier hybridized directly or indirectly (via one or more oligonucleotides) to a sequence of the RCA product. In some embodiments, the assembly includes one or more amplifiers each including an amplifier repeating sequence. In some aspects, the one or more amplifiers is labeled. Described herein is a method of using the aforementioned assembly, including for example, using the assembly in multiplexed error-robust fluorescent in situ hybridization (MERFISH) applications, with branched DNA amplification for signal readout. In some embodiments, the amplifier repeating sequence is about 5-30 nucleotides, and is repeated N times in the amplifier. In some embodiments, the amplifier repeating sequence is about 20 nucleotides, and is repeated at least two times in the amplifier. In some aspects, the one or more amplifier repeating sequence is labeled. For exemplary branched signal amplification, see e.g., U.S. Pat. Pub. No. US20200399689A1, WO 2020/123742, US 20220064697 and Xia et al., Multiplexed Detection of RNA using MERFISH and branched DNA amplification. Scientific Reports (2019), each of which is fully incorporated by reference herein.

In some embodiments, detection of nucleic acids sequences in situ includes a primer exchange reaction (PER). In various embodiments, a primer with a domain on its 3' end binds to a catalytic hairpin, and is extended with a new domain by a strand displacing polymerase. For example, a primer with domain 1 on its 3' ends binds to a catalytic hairpin, and is extended with a new domain 1 by a strand displacing polymerase, with repeated cycles generating a concatemer of repeated domain 1 sequences. In various embodiments, the strand displacing polymerase is Bst. In various embodiments, the catalytic hairpin includes a stopper which releases the strand displacing polymerase. In various embodiments, branch migration displaces the extended primer, which can then dissociate. In various embodiments, the primer undergoes repeated cycles to form a concatemer primer. In various embodiments, a plurality of concatemer primers is contacted with a sample comprising RCA products generated using methods described herein. In various embodiments, the RCA product may be contacted with a plurality of concatemer primers and a plurality of labeled probes. see e.g., U.S. Pat. Pub. No. US20190106733, which is incorporated herein by reference, for exemplary molecules and PER reaction components.

In some embodiments, a reporter oligonucleotide and a sample identification probe directly or indirectly bound thereto can comprise a region which is configured to hybridize to a detectable probe or probe set. In some embodiments, the detectable probe or probe set is circular or circularizable to generate a circularized template. In some embodiments, the circular probe or circularized template is used to generate an RCA product. In some embodiments, a reporter oligonucleotide and a sample identification probe directly or indirectly bound thereto can comprise a region which is an initiator for hybridization chain reaction (HCR) or which hybridizes to an initiator for HCR. In some embodiments, a reporter oligonucleotide and a sample identification probe directly or indirectly bound thereto can comprise a region which is an initiator for linear oligonucleotide hybridization chain reaction (LO-HCR) or which hybridizes to an initiator for LO-HCR. In some embodiments, a reporter oligonucleotide and a sample identification probe directly or indirectly bound thereto can comprise a region which is a primer for primer exchange reaction (PER) or which hybridizes to a primer for PER. In some embodiments, a reporter oligonucleotide and a sample identification probe directly or indirectly bound thereto can comprise a region which is a pre-amplifier for branched DNA (bDNA) or which hybridizes to a pre-amplifier for bDNA.

In some embodiments, an analyte detection probe can comprise a region which is configured to hybridize to a detectable probe or probe set. In some embodiments, the detectable probe or probe set is circular or circularizable to generate a circularized template. In some embodiments, the circular probe or circularized template is used to generate an RCA product. In some embodiments, an analyte detection probe can comprise a region which is an initiator for hybridization chain reaction (HCR) or which hybridizes to an initiator for HCR. In some embodiments, an analyte detection probe can comprise a region which is an initiator for linear oligonucleotide hybridization chain reaction (LO-HCR) or which hybridizes to an initiator for LO-HCR. In some embodiments, an analyte detection probe can comprise a region which is a primer for primer exchange reaction (PER) or which hybridizes to a primer for PER. In some embodiments, an analyte detection probe can comprise a region which is a pre-amplifier for branched DNA (bDNA) or which hybridizes to a pre-amplifier for bDNA.

Figure 4:
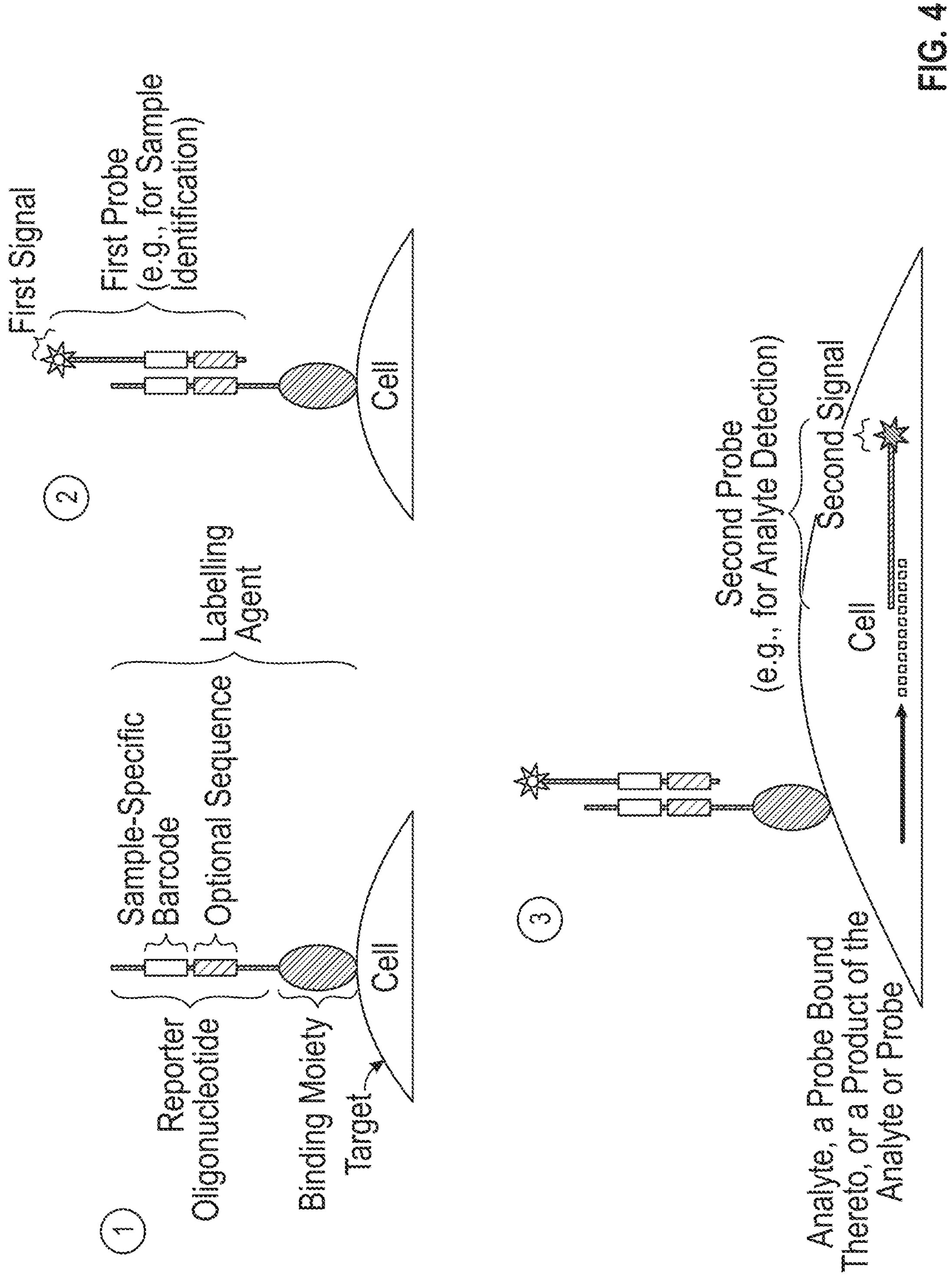
FIG. 4 shows an exemplary assay workflow, where a labeling agent binds to a target in and/or on a cell (e.g., on the cell surface) in step 1, a first probe (e.g., for sample identification) hybridizes to a reporter oligonucleotide of the labeling agent in step 2, and a second probe hybridizes directly or indirectly to an analyte (e.g., RNA or DNA) in the cell in step 3. Steps 2 and 3 may be performed simultaneously or in either order.
Figure 5:
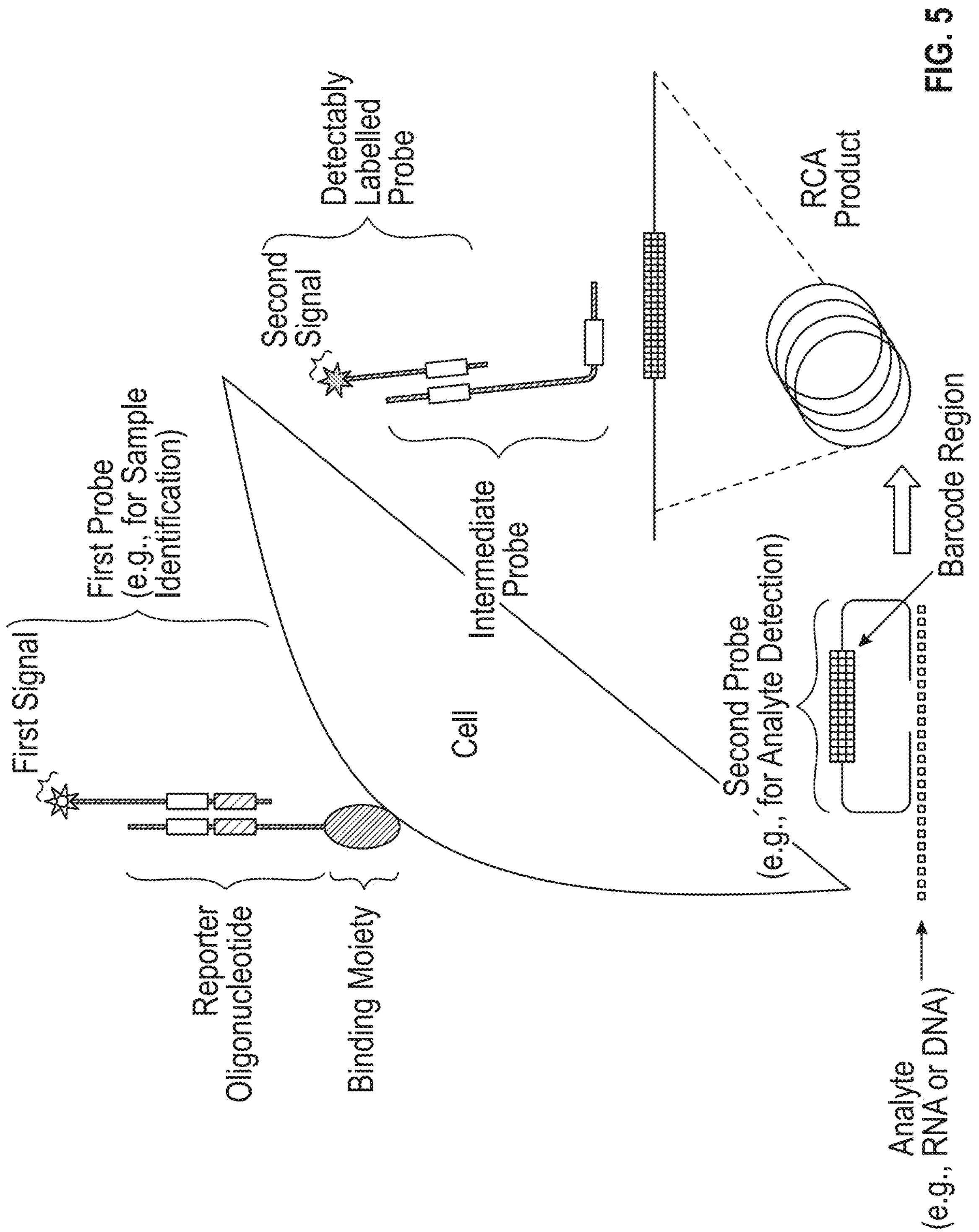
FIG. 5 shows an example where a second probe directly or indirectly hybridizes to a nucleic acid (e.g., a nucleic acid analyte or a nucleic acid tag of a probe that binds to a non-nucleic acid analyte) and an RCA product of the second probe is generated in the cell. The second probe may comprise a barcode region and the RCA product can be detected in situ, e.g., using an intermediate probe and a detectably labeled probe as shown in the figure.

In FIG. 4, the second probe (e.g., an analyte detection probe) is shown as a detectably labeled probe. However, it should be appreciated that the second probe does not need to be detectably labeled. In some examples, the second probe or a product thereof can be detected by a detectable probe that hybridizes to a detectably labeled probe. For instance, the second probe can be a circularizable probe which is circularized and amplified (e.g., by rolling circle amplification, RCA) in situ to generate an amplification product, which is detected by a detectable probe (e.g., an intermediate probe) that hybridizes to the amplification product as well as a fluorescently labeled probe. In FIG. 5, the RCA product can comprise multiple copies of a hybridization region (e.g., one or more barcode sequences) that is bound by an intermediate probe. The intermediate probe may comprise a 3' overhang and/or a 5' overhang that comprises a hybridization region that hybridizes with a detectably labeled probe providing a second signal. The reporter oligonucleotide can be detected similarly (e.g., by generating an RCA product of the reporter oligonucleotide or a probe or probe set hybridized thereto), or by detecting a first signal associated with a first probe that hybridizes to the reporter oligonucleotide as shown in the figure.

In some cases, a first probe (e.g., a sample identification probe) and/or a second probe (e.g., an analyte detection probe) can comprise one or more features of and/or be modified based on: a split FISH probe or probe set described in WO 2021/167526A1 or Goh et al., "Highly specific multiplexed RNA imaging in tissues with split-FISH," Nat Methods 17(7):689-693 (2020), which are incorporated herein by reference in their entireties; a Z-probe or probe set, such as one described in U.S. Pat. No. 7,709,198 B2, U.S. Pat. No. 8,604,182 B2, U.S. Pat. No. 8,951,726 B2, U.S. Pat. No. 8,658,361 B2, or Tripathi et al., "Z Probe, An Efficient Tool for Characterizing Long Non-Coding RNA in FFPE Tissues," Noncoding RNA 4(3):20 (2018), which are incorporated herein by reference in their entireties; an HCR initiator or amplifier, such as one described in U.S. Pat. No. 7,632,641 B2, US 2017/0009278 A1, U.S. Pat. No. 10,450,599 B2, Dirks and Pierce, "Triggered amplification by hybridization chain reaction," PNAS 101(43):15275-15278 (2004), Chemeris et al., "Real-time hybridization chain reaction," Dokl. Biochem 419:53-55 (2008), Niu et al., "Fluorescence detection for DNA using hybridization chain reaction with enzyme-amplification," Chem Commun (Camb) 46(18):3089-91 (2010), Choi et al., "Programmable in situ amplification for multiplexed imaging of mRNA expression," Nat Biotechnol 28(11):1208-12 (2010), Song et al., "Hybridization chain reaction-based aptameric system for the highly selective and sensitive detection of protein," Analyst 137(6):1396-401 (2012), Choi et al., "Third-generation in situ hybridization chain reaction: multiplexed, quantitative, sensitive, versatile, robust," Development 145 (12): dev165753 (2018), or Tsuneoka and Funato, "Modified in situ Hybridization Chain Reaction Using Short Hairpin DNAs," Front Mol Neurosci 13:75 (2020), which are incorporated herein by reference in their entireties; a PLAYR probe or probe set, such as one described in US 2016/0108458 A1 or Frei et al., "Highly multiplexed simultaneous detection of RNAs and proteins in single cells," Nat Methods 13(3):269-75 (2016), which are incorporated herein by reference in their entireties; a PLISH probe or probe set, such as one described in US 2020/0224243 A1 or Nagendran et al., "Automated cell-type classification in intact tissues by single-cell molecular profiling," eLife 7:e30510 (2018), which are incorporated herein by reference in their entireties; a RollFISH probe or probe set such as one described in Wu et al., "RollFISH achieves robust quantification of single-molecule RNA biomarkers in paraffin-embedded tumor tissue samples," Commun Biol 1, 209 (2018), which is hereby incorporated by reference in its entirety; a MERFISH probe or probe set, such as one described in WO 2020/123742 A1 (PCT/US2019/065857), US 20220064697 or Chen et al., "Spatially resolved, highly multiplexed RNA profiling in single cells," Science 348(6233):aaa6090 (2015), which are incorporated herein by reference in their entireties; or a primer exchange reaction (PER) probe or probe set, such as one described in US 2019/0106733 A1, which is hereby incorporated by reference in its entirety.

In some embodiments, the in situ detection herein can comprise sequencing performed in situ by sequencing by synthesis (SBS). In some embodiments, a sequencing primer is complementary to sequences at or near the one or more barcode(s). In such embodiments, sequencing by synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, WO 05/065814, US 2005/0100900, WO 06/064199, WO07/010,251, US 2012/0270305, US 2013/0260372, and US 2013/0079232.

In some embodiments, the in situ detection herein can comprise sequential hybridization, e.g., sequencing by hybridization and/or sequential in situ fluorescence hybridization. Sequential fluorescence hybridization can involve sequential hybridization of detectable probes comprising an oligonucleotide and a detectable label. In some embodiments, a method disclosed herein comprises sequential hybridization of the detectable probes disclosed herein, including detectably labeled probes (e.g., fluorophore conjugated oligonucleotides) and/or probes that are not detectably labeled per se but are capable of binding (e.g., via nucleic acid hybridization) and being detected by detectably labeled probes. Exemplary methods comprising sequential fluorescence hybridization of detectable probes are described in US 2019/0161796, US 2020/0224244, US 2022/0010358, US 2021/0340618, and WO 2021/138676, US 2023/0039899, all of which are incorporated herein by reference.

In some embodiments, the in situ detection herein can comprise sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597.

In some embodiments, the barcodes of the detectable probes are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labeled probes (e.g., detection oligonucleotides). Exemplary decoding schemes are described in Eng et al., "Transcriptome-scale Super-Resolved Imaging in Tissues by RNA SeqFISH+," *Nature* 568(7751):235-239 (2019); Chen et al., "Spatially resolved, highly multiplexed RNA profiling in single cells," Science; 348(6233):aaa6090 (2015); U.S. Pat. No. 10,457,980 B2; US 2016/0369329 A1; WO 2018/026873 A1, US 2021/0017587; and US 2017/0220733 A1, all of which are incorporated by reference in their entirety. In some embodiments, these assays enable signal amplification, combinatorial decoding, and error correction schemes at the same time.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004).

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett*. (2008), 33, 1026-1028, and Korlach et al., *Proc. Natl. Acad. Sci. USA* (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detectable probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detectable probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (e.g., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, provided herein is a method for cell analysis comprising: (a) providing a population of cells comprising a labeled cell, wherein the cell may be labeled with a labeling agent comprising a binding moiety and a reporter oligonucleotide, and wherein the binding moiety may be bound to the cell; (b) depositing the labeled cell on a substrate; (c) contacting the deposited labeled cell with: (i) a first probe that may bind to the labeling agent, and (ii) a second probe that may bind to an analyte in and/or on the deposited labeled cell; and (d) detecting a first signal associated with the first probe or a product thereof and a second signal associated with the second probe or a product thereof in the deposited labeled cell, wherein the labeling agent may comprise a sample-specific barcode sequence corresponding to a sample from which the labeled cell is derived. In some embodiments, the first signal may be associated with the first product and the second signal may be associated with the second product. In some embodiments, the signal(s) (e.g., first and/or second) maybe detected in situ.

In some embodiments, provided herein is a method for cell analysis, comprising: (a) providing a population of cells comprising a labeled cell, wherein the cell may be labeled with a labeling agent comprising (i) a binding moiety and (ii) a reporter oligonucleotide comprising a first barcode region, and wherein the binding moiety may be bound to the cell; (b) immobilizing the population of cells comprising the labeled cell on a substrate; (c) contacting the immobilized cells with: (i) a first probe that may hybridize to the first barcode region, and (ii) a second probe that may bind to an analyte in and/or on one or more of the immobilized cells, wherein the second probe may comprise a second barcode region; and (d) detecting a first signal associated with the first probe or a product thereof and a second signal associated with the second probe or a product thereof on the substrate, thereby detecting the presence or absence of the analyte in the immobilized labeled cell. In some embodiments, the cells in the population may not be partitioned into partitions prior to, during, and/or after the providing step in (a) or during the immobilizing in step (b), optionally wherein the partitions may be emulsion droplets and/or microwells. In some embodiments, the first barcode region may comprise (i) a sample-specific barcode sequence corresponding to a sample from which the labeled cell is derived and optionally (ii) a target-specific barcode sequence corresponding to the binding moiety or target thereof, and/or optionally (iii) a barcode sequence corresponding to a cell feature. In some embodiments, the second barcode region may comprise a binding site for a detectable probe, optionally wherein the detectable probe may comprise: (i) a fluorescently labeled probe, (ii) an intermediate probe comprising a binding site for another detectable probe, optionally wherein the binding site may be a barcode sequence, and/or (iii) a circular probe or circularizable probe or probe set, of which a rolling circle amplification (RCA) product may comprise a plurality of binding sites for yet another detectable probe.

In some embodiments, provided herein is a method for sample analysis, comprising: (a) contacting a first sample and a second sample with a first labeling agent and a second labeling agent, respectively, to provide labeled cells in each sample, wherein the first labeling agent and the second labeling agent each may comprise (i) a binding moiety and (ii) a reporter oligonucleotide comprising a first barcode region comprising a sample-specific barcode sequence corresponding to the respective sample, wherein the binding moiety of each labeling agent may bind to one or more dissociated cells in the respective sample; (b) combining labeled cells from the first and second samples; (c) immobilizing a population of cells comprising labeled cells from the first and second samples on a substrate; (d) contacting the immobilized cells with: (i) a first probe that may hybridize to the sample-specific barcode sequence corresponding to the first or second sample, and (ii) a second probe that may bind to an analyte in and/or on one or more of the immobilized cells, wherein the second probe may comprise a second barcode region; and (e) detecting a first signal associated with the first probe or a product thereof and a second signal associated with the second probe or a product thereof on the substrate, thereby detecting the presence or absence of the analyte in one or more cells from the first sample and/or from the second sample. In some embodiments, the first sample and/or the second sample may comprise dissociated cells.

In some embodiments, provided herein is a method for sample analysis, comprising: (a) contacting a first sample and a second sample with a first labeling agent and a second labeling agent, respectively, to provide labeled cells in each sample, wherein the first labeling agent and the second labeling agent each may comprise (i) a binding moiety and (ii) a reporter oligonucleotide comprising a first barcode region comprising a sample-specific barcode sequence corresponding to the respective sample, wherein the binding moiety of each labeling agent may bind to one or more cells in the respective sample; (b) combining the first and second samples; (c) immobilizing a population of dissociated cells comprising labeled cells from the first and second samples on a substrate; (d) contacting the immobilized cells with: (i) a first probe that may hybridize to the sample-specific barcode sequence corresponding to the first or second sample, and (ii) a second probe that may bind to an analyte in and/or on one or more of the immobilized cells, wherein the second probe may comprise a second barcode region; and (e) detecting a first signal associated with the first probe or a product thereof and a second signal associated with the second probe or a product thereof on the substrate, thereby detecting the presence or absence of the analyte in one or more cells from the first sample and/or from the second sample. In some embodiments, the first and second samples may be combined in (b) prior to processing the first and second samples to provide the population of dissociated cells in (c). In some embodiments, the first and second samples may be processed separately to provide dissociated cells prior to combining the dissociated cells in (b) to provide the population of dissociated cells in (c). In some embodiments, the first probe and/or the second barcode region may comprise one or more barcode sequences, optionally wherein the first probe and/or second probe may be a circularizable probe.

In some embodiments, the first signal and/or the second signal may be associated with a rolling circle amplification (RCA) product of a circularized probe comprising a sequence of the circularizable probe, wherein the RCA product may comprise multiple copies of the complement of the one or more barcode sequences, and wherein the first signal and/or the second signal may be detected using a detectable probe that hybridizes to the complement, optionally wherein the detectable probe may be detectably labeled or may comprise a sequence that hybridizes to a detectably labeled probe. In some embodiments, the method may comprise detecting signals associated with the one or more barcode sequences in sequential cycles using a plurality of detectable probes, thereby detecting the presence or absence of the analyte in one or more cells from the first sample and/or from the second sample.

VI. Compositions and Kits

Also provided herein are kits, for example comprising one or more polynucleotides disclosed herein, and reagents for performing the methods provided herein, for example reagents required for one or more steps comprising hybridization, ligation, amplification, detection, and/or sample preparation as described herein. In some embodiments, the kit comprises one or more substrates.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcoded detectable probes or detectable labels. In some embodiments, the kits optionally contain other components, for example nucleic acid primers, enzymes and reagents, buffers, nucleotides, modified nucleotides, reagents for additional assays.

VII. Terminology

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample, a target, a bead, and/or a sample). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G).

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (e.g., can be oligoribonucleotides) and/or deoxyribonucleotide monomers (e.g., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Subject

A "subject" is an animal, such as a mammal (e.g., human or a non-human simian), or avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (e.g. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, or honey bee; an arachnid such as a spider; a fish such as zebrafish; a reptile; an amphibian such as a frog or *Xenopus laevis*; a Dictyostelium discoideum; a fungi such as *Pneumocystis carinii, Takifugu rubripes*, yeast, *Saccharamoyces cerevisiae* or *Schizosaccharomyces pombe*; or a *Plasmodium falciparum*.

(vi) Splint Oligonucleotide

A "splint oligonucleotide" is an oligonucleotide that, when hybridized to other polynucleotides, acts as a "splint" to position the polynucleotides next to one another so that they can be ligated together. In some embodiments, the splint oligonucleotide is DNA or RNA. The splint oligonucleotide can include a nucleotide sequence that is partially complimentary to nucleotide sequences from two or more different oligonucleotides. In some embodiments, the splint oligonucleotide assists in ligating a "donor" oligonucleotide and an "acceptor" oligonucleotide. In general, an RNA ligase, a DNA ligase, or another other variety of ligase is used to ligate two nucleotide sequences together.

In some embodiments, the splint oligonucleotide is between 10 and 50 oligonucleotides in length, e.g., between 10 and 45, 10 and 40, 10 and 35, 10 and 30, 10 and 25, or 10 and 20 oligonucleotides in length. In some embodiments, the splint oligonucleotide is between 15 and 50, 15 and 45, 15 and 40, 15 and 35, 15 and 30, 15 and 30, or 15 and 25 nucleotides in length.

(vii) Adaptor, Adapter, and Tag

An "adaptor," an "adapter," and a "tag" are terms that are used interchangeably in this disclosure, and refer to species that can be coupled to a polynucleotide sequence (in a process referred to as "tagging") using any one of many different techniques including (but not limited to) ligation, hybridization, and tagmentation. Adaptors can also be nucleic acid sequences that add a function, e.g., spacer sequences, primer sequences/sites, barcode sequences, unique molecular identifier sequences.

(viii) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(ix) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(x) Primer Extension

Two nucleic acid sequences can become linked (e.g., hybridized) by an overlap of their respective complementary nucleic acid sequences. Such linking can be followed by nucleic acid extension (e.g., an enzymatic extension) of one, or both termini (e.g., 3' termini) using the other nucleic acid sequence as a template for extension. Enzymatic extension can be performed by an enzyme including, but not limited to, a polymerase and/or a reverse transcriptase.

(xi) Proximity Ligation

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference).

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(xii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence can be used as a template for single-strand synthesis of a corresponding cDNA molecule.

(xiii) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e g enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments, the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9° N) DNA ligase (9° NTM DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA can be carried out by real-time PCR (also known as quantitative PCR or qPCR), using techniques such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xiv) Antibody

An "antibody" is a polypeptide molecule that recognizes and binds to a complementary target antigen. Antibodies typically have a molecular structure shape that resembles a Y shape. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form epitope binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site.

Antibodies can also refer to an "epitope binding fragment" or "antibody fragment," which as used herein, generally refers to a portion of a complete antibody capable of binding the same epitope as the complete antibody, albeit not necessarily to the same extent. Although multiple types of epitope binding fragments are possible, an epitope binding fragment typically comprises at least one pair of heavy and light chain variable regions (VH and VL, respectively) held together (e.g., by disulfide bonds) to preserve the epitope binding site, and does not contain all or a portion of the Fc region. Epitope binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an epitope binding fragment comprises an F(ab')2 fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific epitope binding ability to the polypeptide.

(xv) Affinity Group

An "affinity group" is a molecule or molecular moiety which has a high affinity or preference for associating or binding with another specific or particular molecule or moiety. The association or binding with another specific or particular molecule or moiety can be via a non-covalent interaction, such as hydrogen bonding, ionic forces, and van der Waals interactions. An affinity group can, for example, be biotin, which has a high affinity or preference to associate or bind to the protein avidin or streptavidin. An affinity group, for example, can also refer to avidin or streptavidin which has an affinity to biotin. Other examples of an affinity group and specific or particular molecule or moiety to which it binds or associates with include, but are not limited to, antibodies or antibody fragments and their respective antigens, such as digoxigenin and anti-digoxigenin antibodies, lectin, and carbohydrates (e.g., a sugar, a monosaccharide, a disaccharide, or a polysaccharide), and receptors and receptor ligands.

Any pair of affinity group and its specific or particular molecule or moiety to which it binds or associates with can have their roles reversed, for example, such that between a first molecule and a second molecule, in a first instance the first molecule is characterized as an affinity group for the second molecule, and in a second instance the second molecule is characterized as an affinity group for the first molecule.

(xvi) Label, Detectable Label, and Optical Label

The terms "detectable label," "optical label," and "label" are used interchangeably herein to refer to a directly or indirectly detectable moiety that is associated with (e.g., conjugated to) a molecule to be detected. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. For example, detectably labeled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a detectable probe. For example, detectable labels can be incorporated during nucleic acid polymerization or amplification (e.g., Cy5®-labeled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAGTm CBQCA, ATTO-TAGTm FQ, Auramine O-Feulgen, BCECF (high pH), BFP (Blue Fluorescent Protein), BFP/GFP FRET, BOBO™1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, C1-NERF (low pH), CPM, 6-CR 6G, CTC Formazan, Cy2®, Cy3®, Cy3.5®, Cy50, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18(5)), DIDS, Dil (DilC18(3)), DiO (DiOC18 (3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJOTM4/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-CyS, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WeliRED D4 Dye, WeliRED D3 Dye, WeliRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

(xvii) Template Switching Oligonucleotide

A "template switching oligonucleotide" is an oligonucleotide that hybridizes to untemplated nucleotides added by a reverse transcriptase (e.g., enzyme with terminal transferase activity) during reverse transcription. In some embodiments, a template switching oligonucleotide hybridizes to untemplated poly(C) nucleotides added by a reverse transcriptase. In some embodiments, the template switching oligonucleotide adds a common 5' sequence to full-length cDNA that is used for cDNA amplification.

In some embodiments, the template switching oligonucleotide adds a common sequence onto the 5' end of the RNA being reverse transcribed. For example, a template switching oligonucleotide can hybridize to untemplated poly(C) nucleotides added onto the end of a cDNA molecule and provide a template for the reverse transcriptase to continue replication to the 5' end of the template switching oligonucleotide, thereby generating full-length cDNA ready for further amplification. In some embodiments, once a full-length cDNA molecule is generated, the template switching oligonucleotide can serve as a primer in a cDNA amplification reaction.

In some embodiments, a template switching oligonucleotide is added before, contemporaneously with, or after a reverse transcription, or other terminal transferase-based reaction. In certain embodiments, methods of sample analysis using template switching oligonucleotides can involve the generation of nucleic acid products from analytes of the tissue sample, followed by further processing of the nucleic acid products with the template switching oligonucleotide.

Template switching oligonucleotides can include a hybridization region and a template region. The hybridization region can include any sequence capable of hybridizing to the target. In some embodiments, the hybridization region can, e.g., include a series of G bases to complement the overhanging C bases at the 3' end of a cDNA molecule. The series of G bases can include 1 G base, 2 G bases, 3 G bases, 4 G bases, 5 G bases, or more than 5 G bases. The template sequence can include any sequence to be incorporated into the cDNA. In other embodiments, the hybridization region can include at least one base in addition to at least one G base. In other embodiments, the hybridization can include bases that are not a G base. In some embodiments, the template region includes at least 1 (e.g., at least 2, 3, 4, 5 or more) tag sequences and/or functional sequences. In some embodiments, the template region and hybridization region are separated by a spacer.

In some embodiments, the template regions include a barcode sequence. The barcode sequence can act as a spatial barcode and/or as a unique molecular identifier. Template switching oligonucleotides can include deoxyribonucleic acids; ribonucleic acids; modified nucleic acids including 2-aminopurine, 2,6-diaminopurine (2-amino-dA), inverted dT, 5-methyl dC, 2'-deoxylnosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' fluoro bases (e.g., Fluoro C, Fluoro U, Fluoro A, and Fluoro G), or any combination of the foregoing.

In some embodiments, the length of a template switching oligonucleotide can be at least about 1, 2, 10, 20, 50, 75, 100, 150, 200, or 250 nucleotides or longer. In some embodiments, the length of a template switching oligonucleotide can be at most about 2, 10, 20, 50, 100, 150, 200, or 250 nucleotides or longer.

EXAMPLES

The following examples are included for illustrative purposes only and are not intended to limit the scope of the present disclosure.

These examples illustrate methods for multiplexing samples and analyzing dissociated cells at a single-cell resolution using in situ detection (e.g., fluorescence microscopy) as a readout.

FIG. 1 is a schematic diagram depicting an exemplary workflow of a multiplexed assay on an in situ platform. In step 101, cells or nuclei from each of multiple biological samples can be labeled with a sample-specific labeling agent, wherein cells and/or nuclei from the same sample are labeled with the same labeling agent and cells and/or nuclei from different samples are labeled with different labeling agents. Different samples can receive different labeling agents and the reporter oligonucleotide of the labeling agent can be used to identify the sample from which a labeled cell or nucleus is derived. The labeled cells and/or nuclei from multiple biological samples are combined in 102, and deposited and/or immobilized in 103 on a substrate (e.g., glass slide). The immobilized cells and/or nuclei are contacted with a plurality of probes that hybridize to the labeling agents and with a plurality of probes that hybridize to analytes (e.g., nucleic acids) in the cells and/or nuclei in 104. After hybridization of the probes, extension, ligation, amplification and/or reverse transcription, may optionally occur in 105, and detectably labeled detection oligonucleotides, such as fluorescently labeled oligonucleotides, are allowed to hybridize with the plurality of probes or products thereof. The fluorescent signals of the hybridization products are then detected (e.g., using a microscope) in 106. An imaging step can be performed prior to, during, and/or after the detecting step, for example, to image a shape, a size, a morphological feature and/or a marker of one or more immobilized labeled cells and/or nuclei. Post imaging, the immobilized cells and/or nuclei can be optionally subjected to probe stripping steps to remove the detectably labeled probes for subsequent hybridization cycles. If a plurality of analytes are being analyzed, multiple cycles of hybridization can be performed and images are acquired in each cycle. Probe sets can sequentially or simultaneously be provided, processed, and detected for decoding and multiplex analysis, including de-multiplexing to identify different sample sources of the labeled cells and/or nuclei. Signals of a plurality of detectable probes detected in sequential cycles of probe hybridization can be used to generate signal code sequences, each analyte can be assigned a unique signal code sequence, and the temporal order and combination of signal codes (e.g., binary codes or color codes) can be used to combinatorially decode the plurality of analytes and detect the analytes at single cells and/or nuclei deposited at locations on the substrate.

Cells and/or nuclei in a sample can be simultaneously analyzed for two or more features and/or cellular analytes. For instance, a population of cells and/or nuclei in a suspension can be contacted, simultaneously or in any suitable order, with a plurality of labeling agents. The plurality of labeling agents may include labeling agents that target one or more cell surface proteins, and/or labeling agents that target one or more RNA species (e.g., using a labeling agent comprising a cell-penetrating moiety described in Section III-D-i). Biological samples (e.g., tissue samples) can be dissociated using various techniques into non-aggregated cells (e.g., single cells) prior to immobilization of the cells on a substrate for an in situ analysis. The biological samples can be contacted with labeling agents prior to or after cell dissociation. The dissociated cells and/or nuclei of the cells from each biological sample can be labeled with one or more labeling agents as shown in FIG. 2. Labeling agents can target cell surface proteins and/or mRNA. The labeling agents may comprise a functional moiety 201 (e.g., a binding moiety) and a reporter oligonucleotide 202 attached thereto. The binding moiety may be a protein or polypeptide (e.g., an antigen or prospective antigen) or an antibody (or an epitope binding fragment thereof). The reporter oligonucleotide can be covalently conjugated to the functional moiety or attached to the functional moiety via nucleic acid hybridization between adapter sequences 205 and 206. The reporter oligonucleotide comprises a sample-specific barcode sequence 203 and one or more optional sequences 204, such as an optional primer sequence, an optional target-specific barcode sequence, and an optional functional sequence. In some embodiments, the sample-specific barcode sequence is specific to the sample from which the cell or nucleus is derived.

Figure 3:
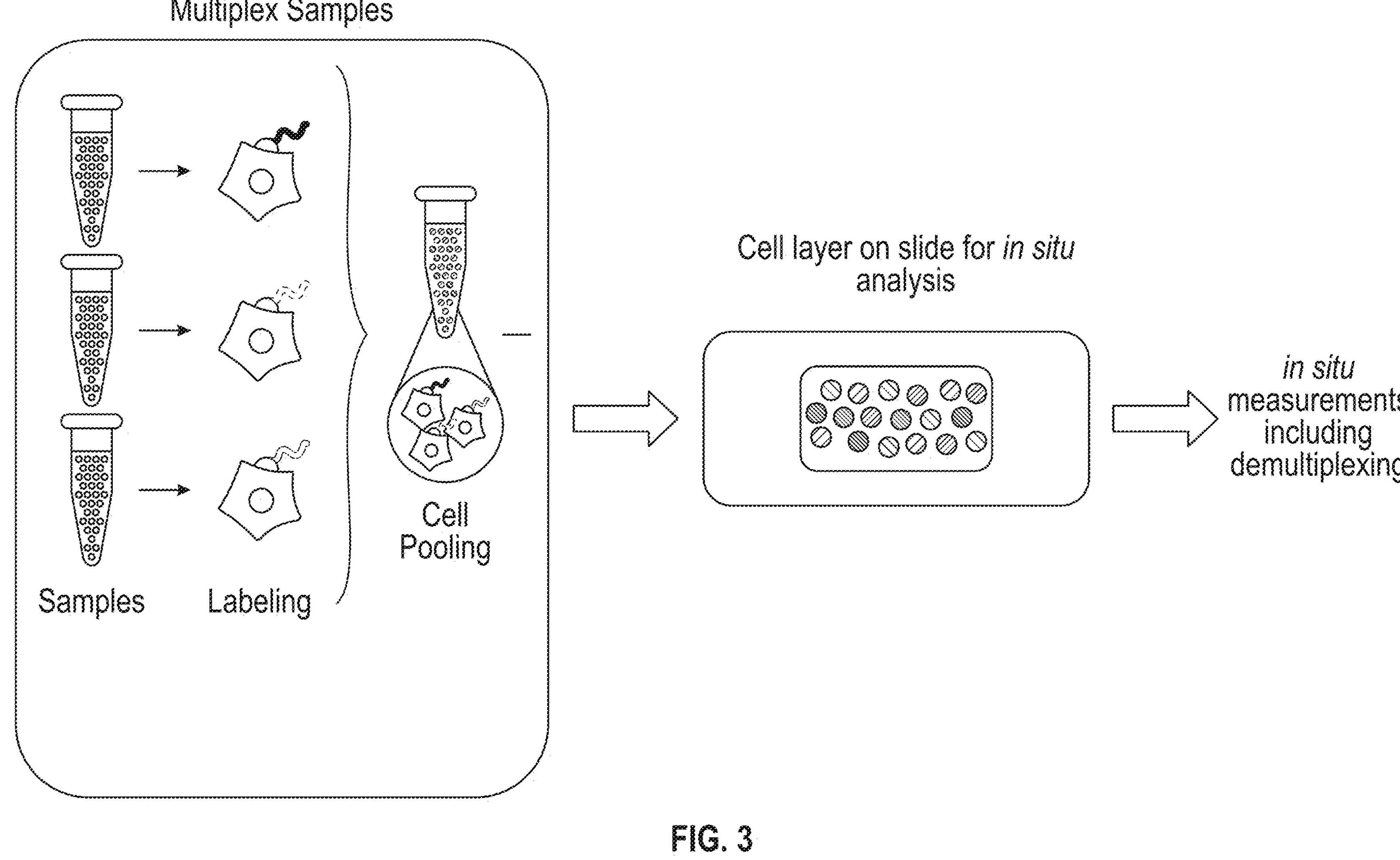
FIG. 3 schematically illustrates an exemplary method of analyzing dissociated single cells using an in situ assay platform. A plurality of biological samples comprising dissociated single cells are labeled with labeling agents comprising sample-specific barcode sequences, pooled and deposited and/or immobilized onto a substrate for analysis of analytes in the single cells in situ.

An exemplary workflow of the multiplexed single cell in situ assay is shown in FIG. 3. Dissociated cells and/or nuclei from multiple biological samples are labeled with sample-specific labeling agents. Optionally, cells may be dissociated after labeling with sample-specific labeling agents. The cells and/or nuclei from a plurality of samples are then pooled and immobilized on a substrate for the in situ analysis. This integrated in situ analysis provides the ability to pool labeled cells and/or nuclei from multiple samples and perform analysis at a single cell resolution. This multiplexed approach allows for a high-throughput analysis (e.g., about 100,000 cells and/or nuclei in a 1 $cm^2$ substrate area) with large cost benefits.

Post labeling, the biological samples (e.g., suspensions of cells) are pooled and immobilized on a substrate (e.g., a microscopy slide or thin substrate, such as a cover slip with sufficient strength). The pooled cell sample is then fixed. For example, the pooled sample may be fixed using paraformaldehyde (PFA, polymeric formaldehyde) and a reversible cross-linking agent. In some instances, nucleic acid molecules (e.g., RNAs) in the sample may be locked in place by embedding the sample in a hydrogel and crosslinking the nucleic acid molecules to the hydrogel. The pooled sample may be first permeabilized with pepsin and HCl, and subsequently fixed. The pooled may be fixed before and/or after the permeabilization step and/or treatment with the reversible crosslinker.

Upon sample fixation, the labeling agents and analytes are targeted by probes and analyzed in situ, following typical highly multiplexed in situ imaging approaches, e.g., probe hybridization, ligation, rolling circle amplification, followed by sequencing by ligation or sequencing by hybridization, with microscopy readouts. For example, as shown in FIG. 4(1) the binding moiety of the labeling agent binds to one or more target molecules on the surface of the cell or nucleus. The immobilized labeled cell or nucleus is then contacted with a first probe that hybridizes to the sample-specific barcode sequence on the reporter oligonucleotide, as shown in FIG. 4(2). The first probe may be detectably labeled or may be further hybridized to a detectably labeled probe. The immobilized cell or nucleus is then contacted with a second probe that binds to an analyte as shown in FIG. 4(3). The analyte may be a nucleic acid (e.g., DNA or RNA) or a non-nucleic acid analyte that is different from the target (e.g., cell surface protein) of the binding moiety. The second probe may be detectably labeled (FIG. 4(3)) or may comprise a region that hybridizes to an intermediate probe. Alternatively, a product of the second probe can comprise a region that hybridizes to an intermediate probe, which in turn may further comprise a sequence that allows hybridization to a detectably labeled probe (FIG. 5). The immobilized cells and/or nuclei are then imaged to visualize the fluorescent signals formed by the detectably labeled hybridization products. Detection of the labeling agents is followed by analysis to associate labeling agents with different sample sources when de-multiplexing.

The present disclosure is not intended to be limited in scope to the particular disclosed embodiments, which are provided, for example, to illustrate various aspects of the disclosure. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for sample analysis, comprising:

(a) contacting a first sample of dissociated cells with a first labeling agent and a second sample of dissociated cells with a second labeling agent, wherein the first labeling agent and the second labeling agent each comprises (i) a binding moiety that binds to cells of the first sample and cells of the second sample, respectively, and (ii) a reporter oligonucleotide comprising a first barcode region comprising a sample-specific barcode sequence that identifies the sample origin of the cells as the first sample and the second sample, respectively (b) combining cells from the first sample that are labeled with the first labeling agent and cells from the second sample that are labeled with the second labeling agent to provide combined labeled cells;

(c) immobilizing at least a portion of the combined labeled cells on a substrate to provide immobilized dissociated cells;

(d) contacting the immobilized dissociated cells with a probe that directly or indirectly binds to an analyte in one or more of the immobilized dissociated cells, wherein the probe comprises a second barcode region that identifies the analyte; and (e) analyzing (i) the sample-specific barcode sequence or a complement thereof and (ii) the second barcode region or a complement thereof in the immobilized dissociated cells on the substrate using nucleic acid sequencing or probe hybridization.

2. The method of claim 1, wherein the sample-specific barcode sequence and the second barcode region are analyzed by sequencing-by-synthesis.

3. The method of claim 1, wherein the binding moiety of the first labeling agent or the binding moiety of the second labeling agent covalently binds to one or more molecules in or on a cell of the first sample or the second sample, respectively.

4. The method of claim 1, wherein the binding moiety of the first labeling agent or the binding moiety of the second labeling agent noncovalently binds to one or more molecules in or on a cell of the first sample or the second sample, respectively.

5. The method of claim 1, wherein the binding moiety of the first labeling agent or the binding moiety of the second labeling agent binds to a surface of a cell of the first sample or the second sample, respectively.

6. The method of claim 1, wherein the binding moiety of the first labeling agent or the binding moiety of the second labeling agent is selected from the group consisting of: an antibody or an epitope binding fragment thereof; a lipophilic moiety; a receptor; a receptor ligand; a small molecule; an aptamer; a monobody; an affimer; a darpin; and a protein scaffold.

7. The method of claim 1, wherein the analyte is a nucleic acid analyte.

8. The method of claim 1, wherein the analyte is a polypeptide.

9. The method of claim 1, wherein the immobilized dissociated cells comprise at least 50,000 dissociated cells.

10. The method of claim 1, wherein the first labeling agent or the second labeling agent further comprises a target-specific barcode sequence that identifies the binding moiety in the first labeling agent or the second labeling agent, respectively.

11. The method of claim 1, wherein the binding moiety is an antibody.

12. The method of claim 1, wherein the analyte is a cellular RNA.

13. The method of claim 12, wherein the probe is a first circularizable probe that hybridizes to the cellular RNA.

14. The method of claim 13, further comprising generating, on the substrate, a first rolling circle amplification (RCA) product of a first circularized probe, wherein the first circularized probe is generated from the first circularizable probe hybridized to the cellular RNA.

15. The method of claim 14, further comprising analyzing the first RCA product on the substrate using (i) sequencing-by-synthesis or (ii) a plurality of detectable probes that hybridize to the first RCA product.

16. The method of claim 14, further comprising contacting the immobilized dissociated cells on the substrate with a second circularizable probe that hybridizes to the sample-specific barcode sequence.

17. The method of claim 16, further comprising generating, on the substrate, a second RCA product of a second circularized probe, wherein the second circularized probe is generated from the second circularizable probe hybridized to the sample-specific barcode sequence.

18. The method of claim 17, further comprising analyzing the second RCA product on the substrate using (i) sequencing-by-synthesis or (ii) a plurality of detectable probes that hybridize to the second RCA product.

19. The method of claim 1, wherein in (c), at least 100 cells are immobilized within an area of 1 $cm^2$ on the substrate.

20. The method of claim 1, wherein in (c), at least 100,000 cells are immobilized within an area of 1 $cm^2$ on the substrate.

* * * * *